US008800386B2

(12) United States Patent
Taylor

(10) Patent No.: US 8,800,386 B2
(45) Date of Patent: Aug. 12, 2014

(54) FORCE SENSING SHEET

(71) Applicant: Stryker Corporation, Kalamazoo, MI (US)

(72) Inventor: Geoffrey L. Taylor, Winnipeg (CA)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 13/724,889

(22) Filed: Dec. 21, 2012

(65) Prior Publication Data
US 2013/0113057 A1 May 9, 2013

Related U.S. Application Data

(63) Continuation of application No. 13/453,461, filed on Apr. 23, 2012, now Pat. No. 8,661,915, which is a continuation of application No. 12/380,845, filed on Mar. 5, 2009, now Pat. No. 8,161,826, application No. 13/724,889, which is a continuation-in-part of application No. 12/075,937, filed on Mar. 15, 2008.

(51) Int. Cl.
G01L 1/22 (2006.01)
G01L 3/00 (2006.01)
G01D 7/00 (2006.01)
G01L 1/20 (2006.01)
H01L 29/84 (2006.01)
G01N 3/08 (2006.01)
G01L 1/18 (2006.01)

(52) U.S. Cl.
CPC ............... H01L 29/84 (2013.01); G01L 1/205 (2013.01); G01N 2203/0623 (2013.01); G01N 3/08 (2013.01); G01L 1/18 (2013.01)
USPC ............ 73/862.044; 73/862.045; 73/862.041; 73/862.042; 73/862.043

(58) Field of Classification Search
USPC ...................... 73/862.041–862.046
See application file for complete search history.

(56) References Cited

U.S. PATENT DOCUMENTS 3,818,756 A 6/1974 Barron et al.
3,996,922 A 12/1976 Basham
(Continued)

FOREIGN PATENT DOCUMENTS

GB 2332063 6/1999
JP 2000000214 1/2000
(Continued)

OTHER PUBLICATIONS

International Preliminary Report on Patentability (including Written Opinion) for PCT/US2010/000645, which claims priority to U.S. Appl. No. 12/380,845, the grandparent of 13/724,889.

(Continued)

Primary Examiner — Lisa Caputo
Assistant Examiner — Jonathan Dunlap
(74) Attorney, Agent, or Firm — Warner Norcross & Judd LLP

(57) ABSTRACT

A force sensing array includes multiple layers of material that are arranged to define an elastically stretchable sensing sheet. The sensing sheet may be placed underneath a patient to detect interface forces or pressures between the patient and the support structure that the patient is positioned on. The force sensing array includes a plurality of force sensors. The force sensors are defined where a row conductor and a column conductor approach each other on opposite sides of a force sensing material, such as a piezoresistive material. In order to reduce electrical cross talk between the plurality of sensors, a semiconductive material is included adjacent the force sensing material to create a PN junction with the force sensing material. This PN junction acts as a diode, limiting current flow to essentially one direction, which, in turn, reduces cross talk between the multiple sensors.

19 Claims, 32 Drawing Sheets

(56) References Cited

U.S. PATENT DOCUMENTS

| | | |
|---|---|---|
| 4,033,332 A | 7/1977 | Hardway, Jr. et al. |
| 4,267,728 A | 5/1981 | Manley et al. |
| 4,308,872 A | 1/1982 | Watson et al. |
| 4,390,028 A | 6/1983 | Okano et al. |
| 4,438,771 A | 3/1984 | Friesen et al. |
| 4,509,527 A | 4/1985 | Fraden |
| RE32,180 E | 6/1986 | Lewiner et al. |
| 4,633,237 A | 12/1986 | Tucknott et al. |
| 4,657,026 A | 4/1987 | Tagg |
| 4,738,266 A | 4/1988 | Thatcher |
| 4,827,763 A | 5/1989 | Bourland et al. |
| 4,986,277 A | 1/1991 | Sackner |
| 5,002,060 A | 3/1991 | Nedivi |
| 5,010,772 A | 4/1991 | Bourland et al. |
| 5,025,795 A | 6/1991 | Kunig |
| 5,060,174 A | 10/1991 | Gross |
| 5,062,169 A | 11/1991 | Kennedy et al. |
| 5,079,949 A | 1/1992 | Tamori |
| 5,128,880 A | 7/1992 | White |
| 5,178,151 A | 1/1993 | Sackner |
| 5,184,112 A | 2/1993 | Gusakov |
| 5,209,126 A | 5/1993 | Grahn |
| 5,253,656 A | 10/1993 | Rincoe et al. |
| 5,276,432 A | 1/1994 | Travis |
| 5,448,996 A | 9/1995 | Bellin et al. |
| 5,471,198 A | 11/1995 | Newham |
| 5,479,932 A | 1/1996 | Higgins et al. |
| 5,515,738 A | 5/1996 | Tamori |
| 5,571,142 A | 11/1996 | Brown et al. |
| 5,571,973 A | 11/1996 | Taylot |
| 5,590,650 A | 1/1997 | Genova |
| 5,600,108 A | 2/1997 | Newham |
| 5,623,760 A | 4/1997 | Newham |
| 5,633,627 A | 5/1997 | Newham |
| 5,640,145 A | 6/1997 | Newham |
| 5,654,694 A | 8/1997 | Newham |
| 5,684,460 A | 11/1997 | Scanlon |
| 5,722,287 A | 3/1998 | Forstein |
| 5,800,360 A | 9/1998 | Kisner et al. |
| 5,800,480 A | 9/1998 | Augustine et al. |
| 5,865,755 A | 2/1999 | Golub |
| 5,964,720 A | 10/1999 | Pelz |
| 5,967,979 A | 10/1999 | Taylor et al. |
| 5,993,400 A | 11/1999 | Rincoe et al. |
| 6,011,477 A | 1/2000 | Teodorescu et al. |
| 6,025,782 A | 2/2000 | Newham |
| 6,033,432 A | 3/2000 | Augustine et al. |
| 6,047,203 A | 4/2000 | Sackner et al. |
| 6,147,592 A | 11/2000 | Ulrich et al. |
| 6,155,120 A | 12/2000 | Taylor |
| 6,180,893 B1 | 1/2001 | Salgo |
| 6,210,427 B1 | 4/2001 | Augustine et al. |
| 6,216,545 B1 | 4/2001 | Taylor |
| 6,279,183 B1 | 8/2001 | Kummer et al. |
| 6,280,392 B1 | 8/2001 | Yoshimi et al. |
| 6,297,738 B1 | 10/2001 | Newham |
| 6,307,168 B1 | 10/2001 | Newham |
| D451,604 S | 12/2001 | Kasabach et al. |
| 6,341,504 B1 | 1/2002 | Istook |
| 6,377,177 B1 | 4/2002 | Broussard et al. |
| 6,396,004 B2 | 5/2002 | Salgo |
| 6,413,225 B1 | 7/2002 | Sackner et al. |
| 6,447,457 B1 | 9/2002 | Forstner et al. |
| 6,450,957 B1 | 9/2002 | Yoshimi et al. |
| 6,468,234 B1 | 10/2002 | Van der Loos et al. |
| 6,478,744 B2 | 11/2002 | Mohler |
| 6,485,441 B2 | 11/2002 | Woodward |
| 6,491,647 B1 | 12/2002 | Bridger et al. |
| 6,493,568 B1 | 12/2002 | Bell et al. |
| 6,497,720 B1 | 12/2002 | Augustine et al. |
| 6,498,652 B1 | 12/2002 | Varshneya et al. |
| 6,524,239 B1 | 2/2003 | Reed et al. |
| 6,543,299 B2 | 4/2003 | Taylor |
| 6,546,813 B2 | 4/2003 | Hubbard, Jr. |
| 6,547,743 B2 | 4/2003 | Brydon |
| 6,551,251 B2 | 4/2003 | Zuckerwar et al. |
| 6,551,252 B2 | 4/2003 | Sackner et al. |
| 6,577,897 B1 | 6/2003 | Shurubura et al. |
| 6,585,328 B1 | 7/2003 | Oexman et al. |
| 6,647,289 B2 | 11/2003 | Prutchi |
| 6,684,418 B2 | 2/2004 | Choi |
| 6,685,635 B2 | 2/2004 | Shani et al. |
| 6,721,980 B1 | 4/2004 | Price et al. |
| 6,829,501 B2 | 12/2004 | Nielsen et al. |
| 6,840,117 B2 | 1/2005 | Hubbard, Jr. |
| 6,840,907 B1 | 1/2005 | Brydon |
| 6,921,365 B2 | 7/2005 | Lee |
| 6,932,774 B2 | 8/2005 | Nakatani et al. |
| 7,001,334 B2 | 2/2006 | Reed et al. |
| 7,030,764 B2 | 4/2006 | Smith et al. |
| 7,054,679 B2 | 5/2006 | Hirsh |
| 7,065,396 B2 | 6/2006 | Hampton |
| 7,076,371 B2 | 7/2006 | Fu |
| 7,125,383 B2 | 10/2006 | Hoctor et al. |
| 7,155,273 B2 | 12/2006 | Taylor |
| 7,155,281 B1 | 12/2006 | Fayram |
| 7,173,437 B2 | 2/2007 | Hervieux et al. |
| 7,201,063 B2 | 4/2007 | Taylor |
| 7,204,808 B1 | 4/2007 | Friedman et al. |
| 7,211,053 B2 | 5/2007 | Marmaropoulos et al. |
| 7,245,956 B2 | 7/2007 | Matthews et al. |
| 7,282,654 B2 | 10/2007 | Salgo et al. |
| 7,301,351 B2 * | 11/2007 | Deangelis et al. ............ 324/687 |
| 7,319,386 B2 | 1/2008 | Collins, Jr. et al. |
| 7,330,127 B2 | 2/2008 | Price et al. |
| 7,331,245 B2 * | 2/2008 | Nishimura et al. ...... 73/862.046 |
| 7,365,031 B2 | 4/2008 | Swallow et al. |
| 7,437,787 B2 | 10/2008 | Bhai |
| 7,459,645 B2 | 12/2008 | Skinner et al. |
| 7,480,953 B2 | 1/2009 | Romano et al. |
| 7,493,810 B2 * | 2/2009 | Walczyk et al. ................. 73/172 |
| 7,500,280 B2 | 3/2009 | Dixon et al. |
| 7,515,059 B2 | 4/2009 | Price et al. |
| 7,557,718 B2 | 7/2009 | Petrosenko et al. |
| 7,568,246 B2 | 8/2009 | Weismiller et al. |
| 7,631,557 B2 | 12/2009 | DeBeliso et al. |
| 7,646,294 B2 | 1/2010 | Kow et al. |
| 7,656,299 B2 | 2/2010 | Gentry et al. |
| 7,657,956 B2 | 2/2010 | Stacy et al. |
| 7,699,784 B2 | 4/2010 | Wan Fong et al. |
| 7,814,801 B2 * | 10/2010 | Inamori ........................... 73/849 |
| 7,984,544 B2 * | 7/2011 | Rosenberg ...................... 29/595 |
| 2001/0042412 A1 | 11/2001 | Serban et al. |
| 2002/0194934 A1 | 12/2002 | Taylor |
| 2003/0004423 A1 | 1/2003 | Lavie et al. |
| 2004/0087865 A1 | 5/2004 | Kelly |
| 2004/0167418 A1 | 8/2004 | Nguyen et al. |
| 2004/0186380 A1 | 9/2004 | Kristiansen |
| 2004/0210155 A1 | 10/2004 | Takemura et al. |
| 2005/0075542 A1 | 4/2005 | Goldreich |
| 2005/0101875 A1 | 5/2005 | Semler et al. |
| 2005/0124864 A1 | 6/2005 | Mack et al. |
| 2005/0171443 A1 | 8/2005 | Gorenberg et al. |
| 2005/0190068 A1 | 9/2005 | Gentry et al. |
| 2005/0241409 A1 | 11/2005 | Taylor |
| 2005/0245839 A1 | 11/2005 | Stivoric et al. |
| 2005/0268962 A1 | 12/2005 | Gaudiana et al. |
| 2005/0282009 A1 | 12/2005 | Nusko et al. |
| 2006/0028350 A1 | 2/2006 | Bhai |
| 2006/0065060 A1 | 3/2006 | Ito et al. |
| 2006/0066449 A1 | 3/2006 | Johnson |
| 2006/0100530 A1 | 5/2006 | Kliot et al. |
| 2006/0100534 A1 | 5/2006 | Colombo et al. |
| 2006/0129047 A1 | 6/2006 | Ruotoistenmaki |
| 2006/0173363 A1 | 8/2006 | Felder et al. |
| 2006/0195035 A1 | 8/2006 | Sun |
| 2006/0224072 A1 | 10/2006 | Shennib |
| 2006/0224076 A1 | 10/2006 | Lange et al. |
| 2006/0241510 A1 | 10/2006 | Halperin et al. |
| 2006/0258914 A1 | 11/2006 | Derchak et al. |
| 2006/0260417 A1 | 11/2006 | Son et al. |
| 2006/0264767 A1 | 11/2006 | Shennib |
| 2007/0083096 A1 | 4/2007 | Paradiso |
| 2007/0118054 A1 | 5/2007 | Pinhas et al. |

(56) References Cited

U.S. PATENT DOCUMENTS

| | | |
|---|---|---|
| 2007/0125181 A1 | 6/2007 | Ofek et al. |
| 2007/0149883 A1 | 6/2007 | Yesha |
| 2007/0156031 A1 | 7/2007 | Sullivan et al. |
| 2008/0200085 A1 | 8/2008 | Van Bruggen et al. |
| 2009/0056027 A1 | 3/2009 | Ball et al. |
| 2009/0093990 A1 | 4/2009 | McGuire et al. |
| 2009/0099480 A1 | 4/2009 | Salgo et al. |
| 2009/0183312 A1 | 7/2009 | Price et al. |
| 2010/0045454 A1 | 2/2010 | Knight et al. |

FOREIGN PATENT DOCUMENTS

| | | |
|---|---|---|
| JP | 2000175904 A | 6/2000 |
| JP | 20000316915 A | 11/2000 |
| JP | 2001000401 A | 1/2001 |
| JP | 2001037821 A | 2/2001 |
| JP | 2002298110 | 10/2002 |
| JP | 2003317905 | 11/2003 |
| JP | 2004132765 | 4/2004 |
| JP | 2004180804 | 7/2004 |
| JP | 2005013259 | 1/2005 |
| JP | 2005204930 | 8/2005 |
| JP | 2005218604 | 8/2005 |
| JP | 2007333412 | 12/2007 |
| JP | 2008049023 | 3/2008 |
| JP | 2008002927 | 10/2008 |
| WO | 2005000108 | 1/2005 |
| WO | 2007059971 | 5/2007 |
| WO | 2009013981 | 1/2009 |

OTHER PUBLICATIONS

English claims of JP2011-552938 (which claims priority to U.S. Appl. No. 12/380,845, the grandparent of 13/724,889) as of Apr. 2, 2013.

English translation of Apr. 2, 2013 Office Action for JP2011-552938.

J.C. Barbenal et al., "Monitoring the mobility of patients in bed", Medical and Biological Engineering and Computing, pp. 466-468, Sep. 1985.

Charles F. Babbs, et al., "A Pressure-Sensitive Mat for Measuring Contact Pressure Distributions . . . ", Biomedical Instrumentation and Technology, pp. 363-370, Sep./Oct. 1990.

Pending U.S. Appl. No. 12/075,937, filed Mar. 13, 2009, which is commonly assigned to the assignee of the present application.

PCT Search Report of the International Searching Authority regarding PCT/US2009/001620, the international counterpart to U.S. Appl. No. 12/075,937.

Laird Technologies. Nick/Copper Polyester Taffeta. Product Specification for 3035-213. <Accessed Online> Sep. 6, 2011. <http://www.stockwell.com/data_sheets/esd_emi/3035213_nickel_polyester_taffeta.pdf>.

Bergen Cable Technology. Cabel 101. <Accessed Online> Sep. 7, 2011. <http://www.bergencable.com/technology/technology_cable101.html>.

Makoto Shimojo, et al., "A Tactile Sensor Sheet Using Pressure Conductive Rubber With Electrical-Wires Stitched Method", IEEE Sensors Journal, vol. 4, No. 5, Oct. 2004.

Wesley E. Snyder, et al., "Conductive Elastomers as Sensor for Industrial Parts Handling Equipment", IEEE Transactions on Instrumentation and Measurement, vol. IM-27, No. 1, Mar. 1978.

Sep. 13, 2012, Office Action from Chinese Patent Office for application 201080018961.5, the Chinese counterpart to U.S. Appl. No. 12/380,845, the grandparent of 13/724,889.

English translation of claims of Chinese patent application 201080018961.5 as of Sep. 13, 2012.

Jun. 27, 2011, Office Action for commonly assigned U.S. Appl. No. 12/075,937, a parent of 13/724,889.

Sep. 27, 2011, Response to Jun. 27, 2011, Office Action for commonly assigned U.S. Appl. No. 12/075,937.

Mar. 8, 2012, Office Action for commonly assigned U.S. Appl. No. 12/075,937.

May 29, 2012, Response to Mar. 8, 2012, Office Action for commonly assigned U.S. Appl. No. 12/075,937.

Sep. 10, 2012, Office Action for commonly assigned U.S. Appl. No. 12/075,937.

Apr. 2, 2013, Office Action for commonly assigned U.S. Appl. No. 13/453,461, a parent of 13/724,889.

* cited by examiner

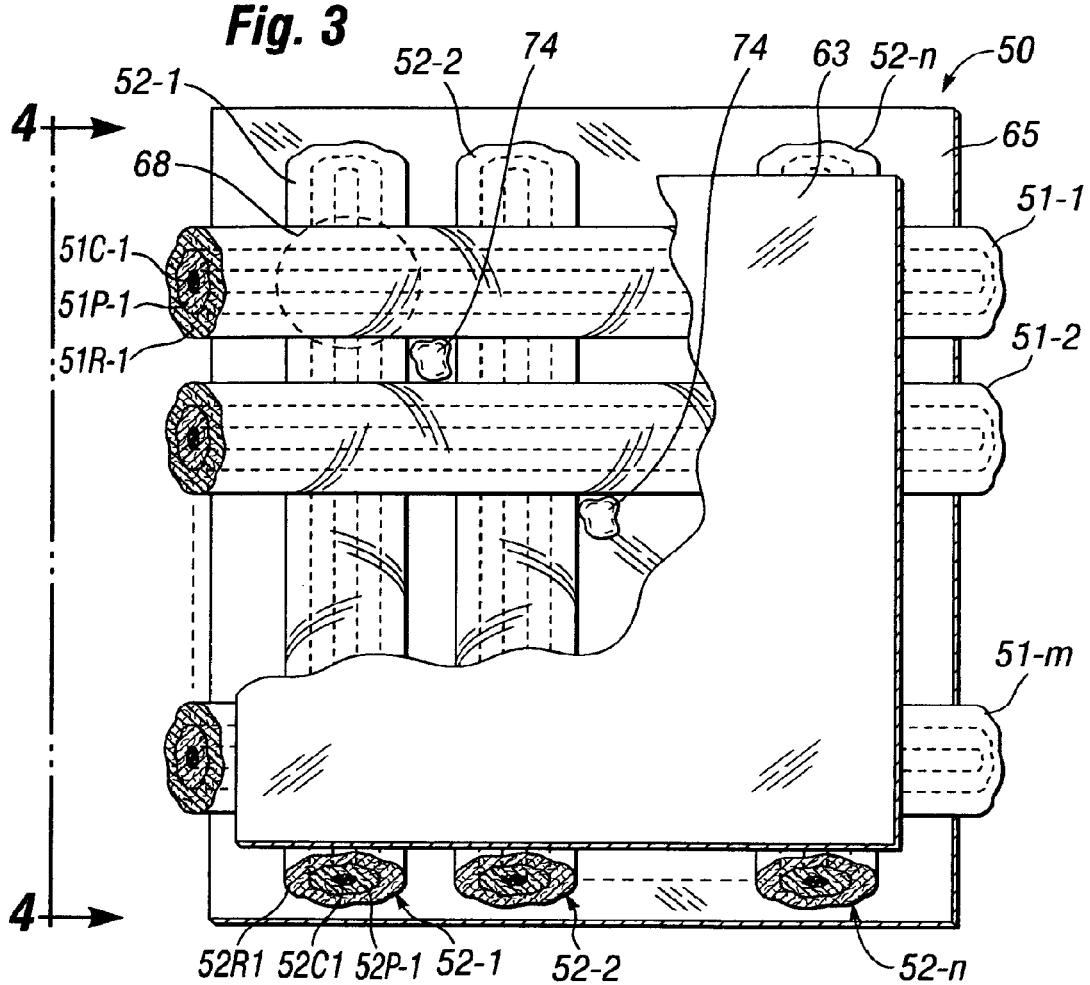
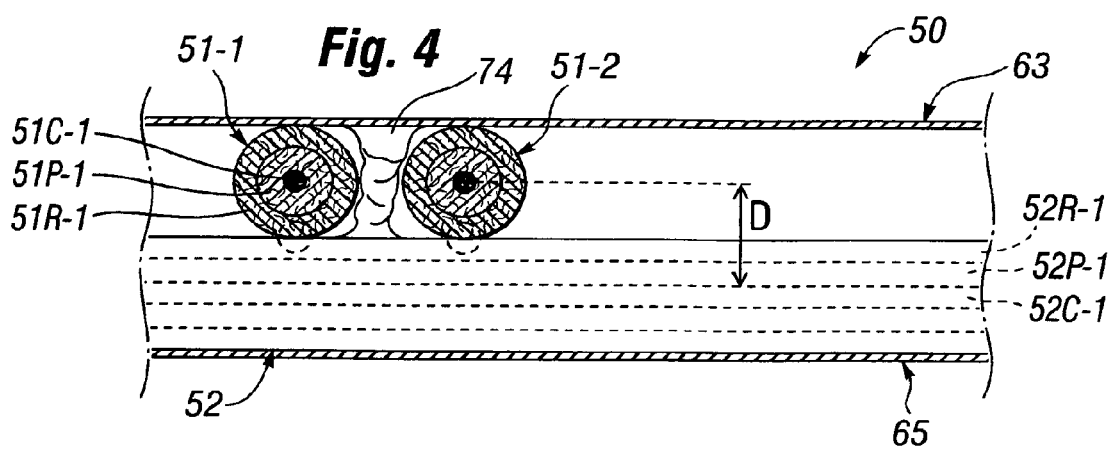

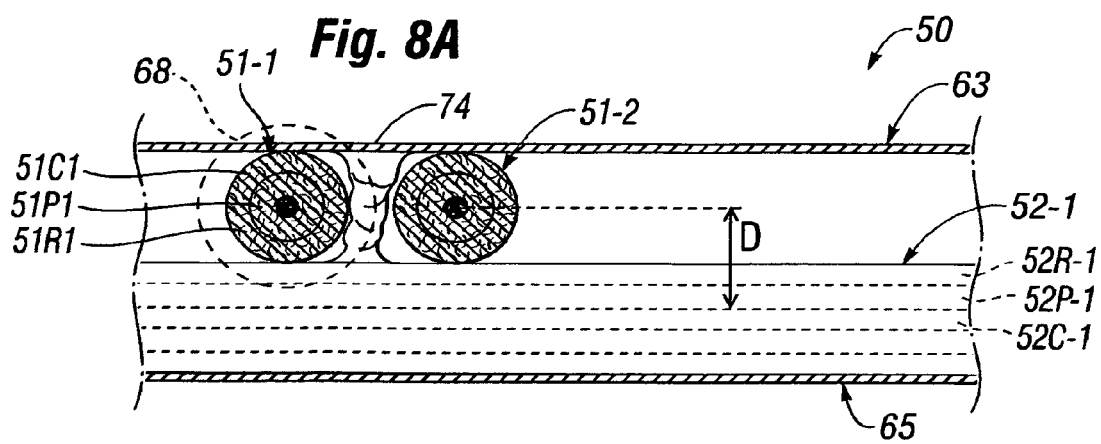
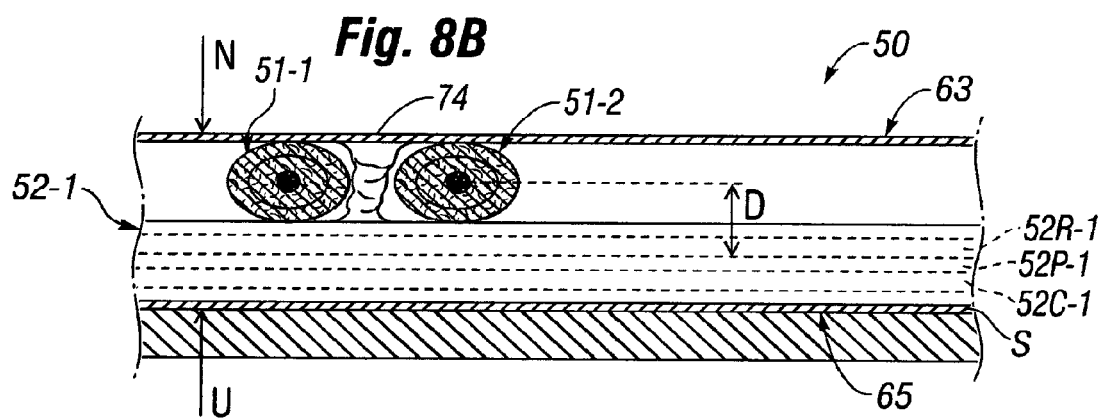
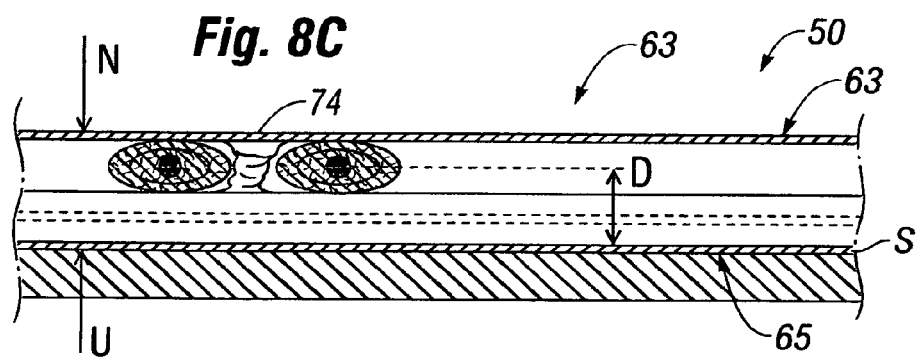

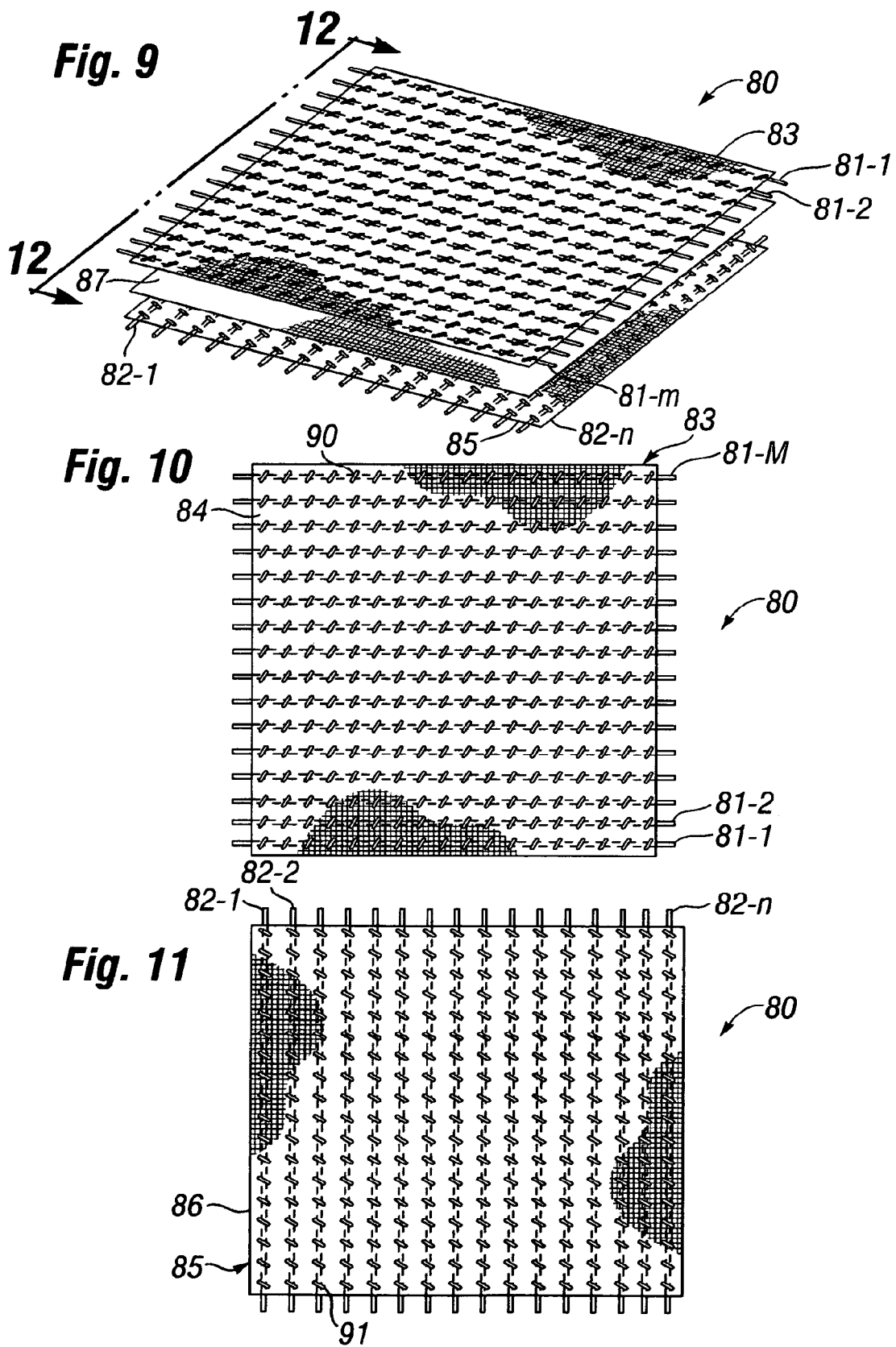

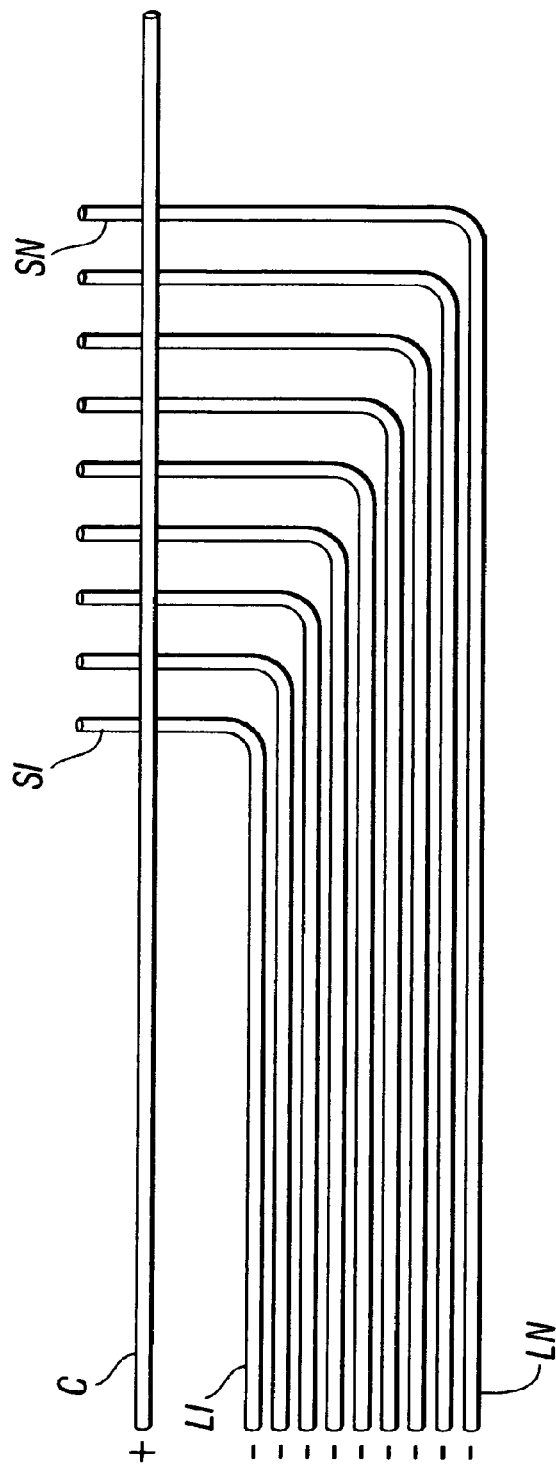
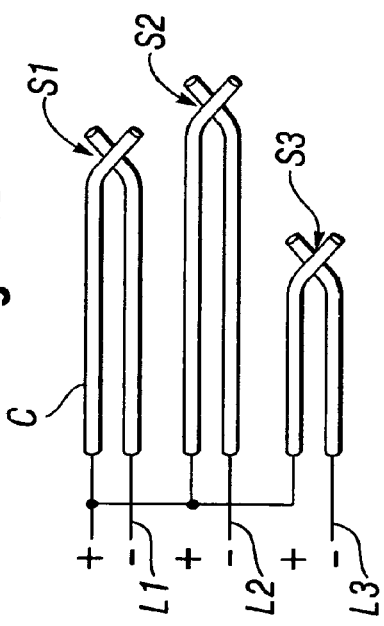
Fig. 22A
Fig. 22B

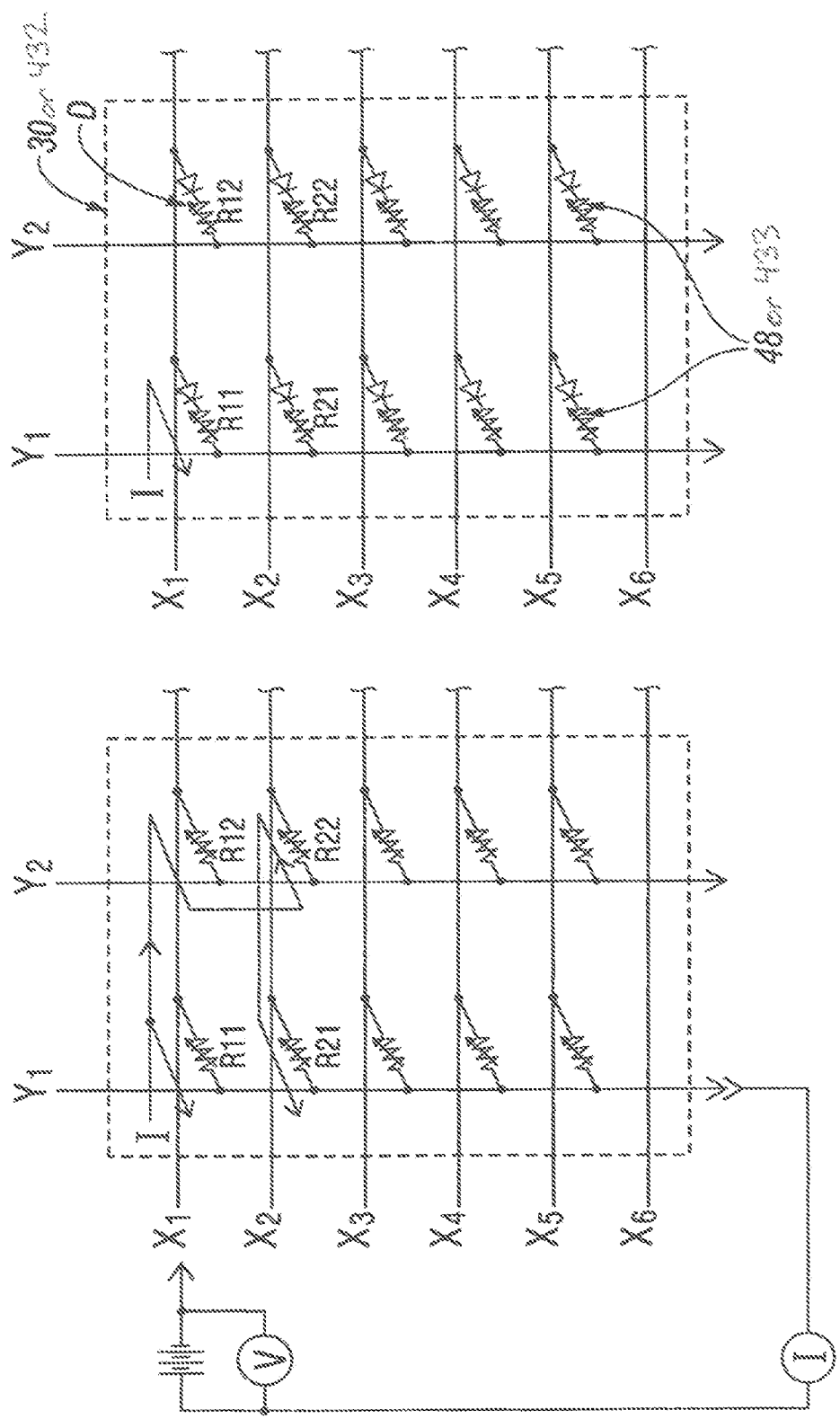

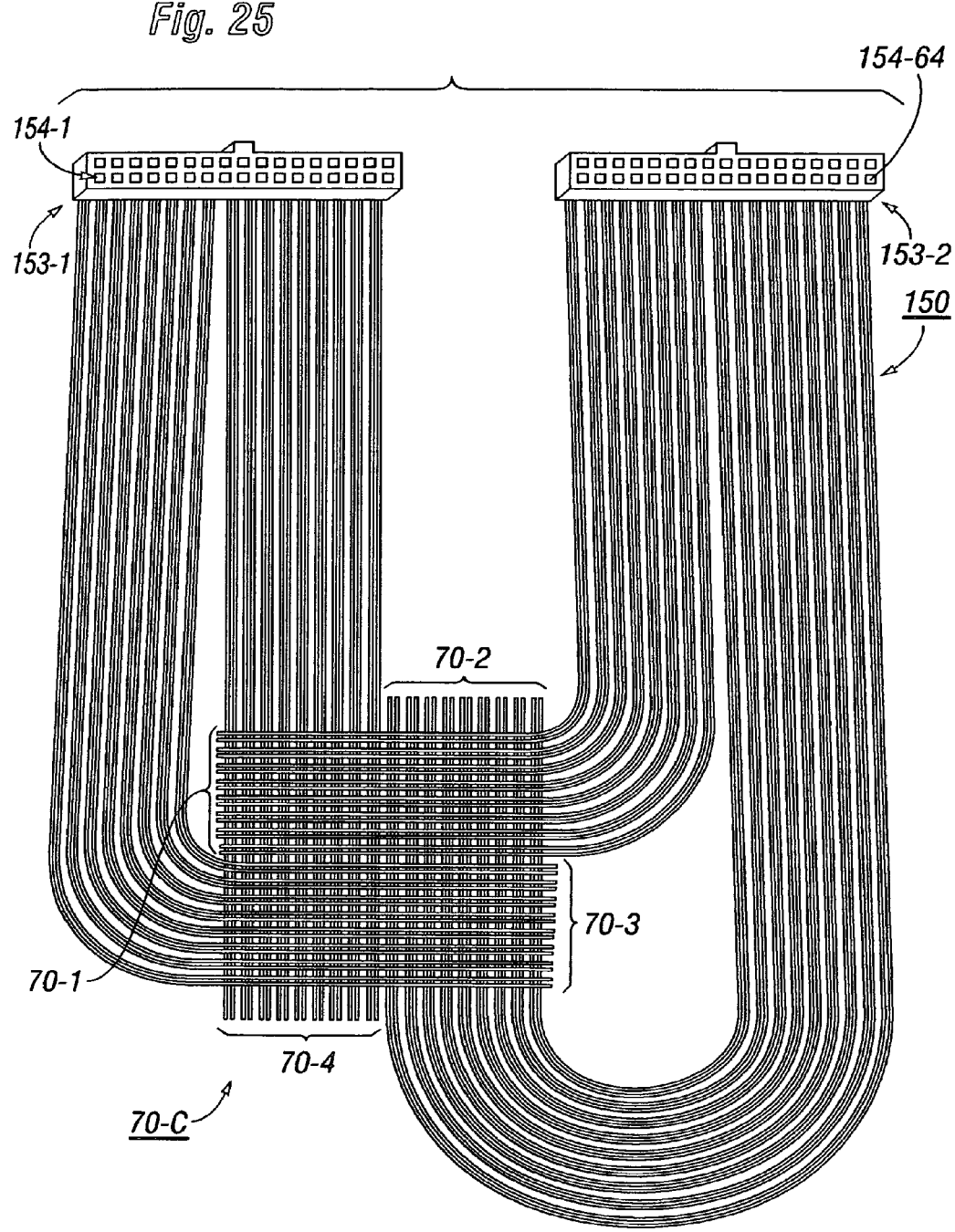

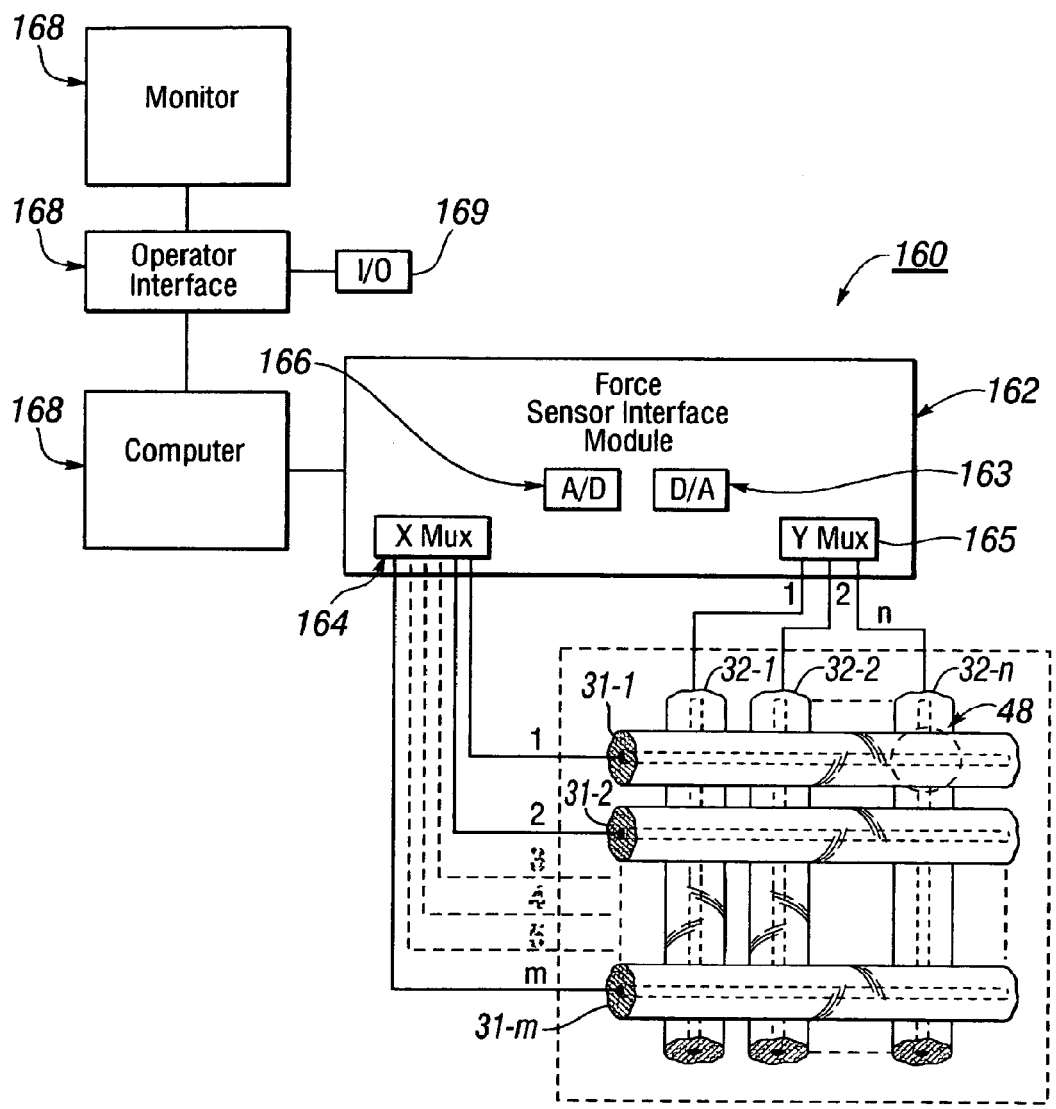

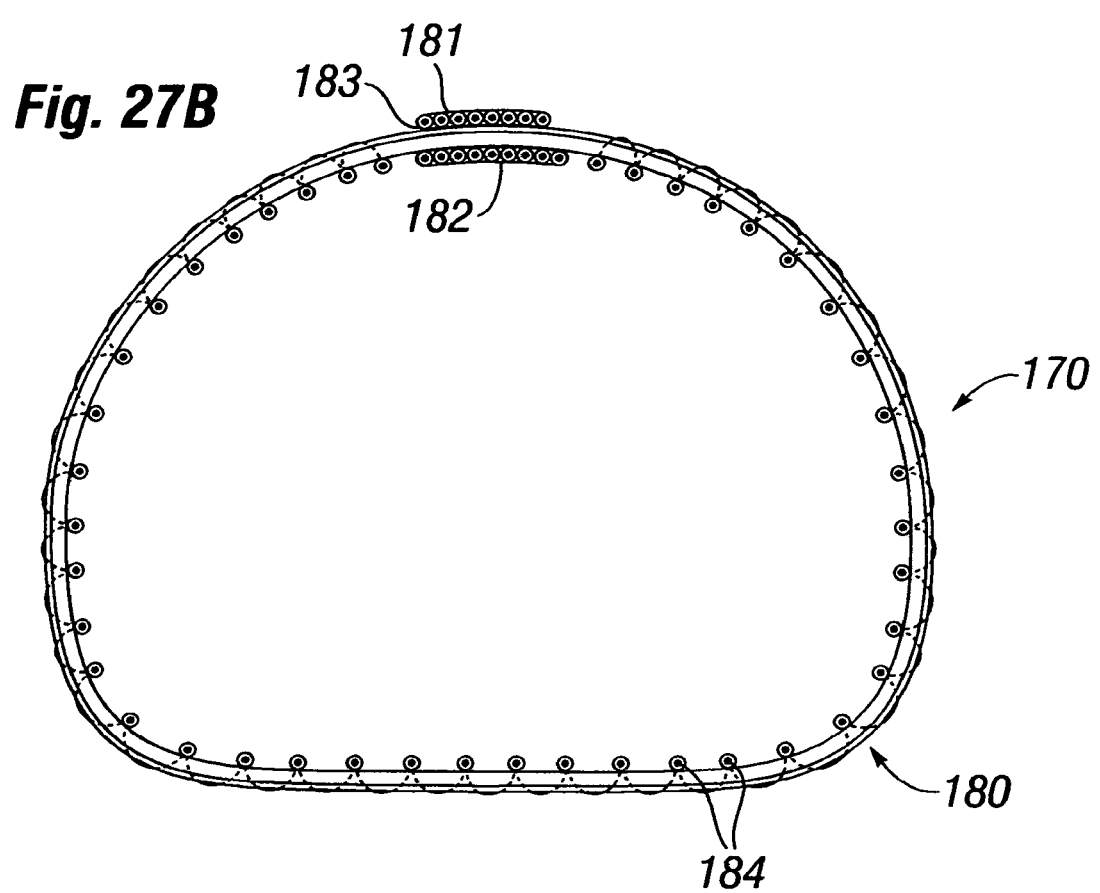

Resistance vs Load

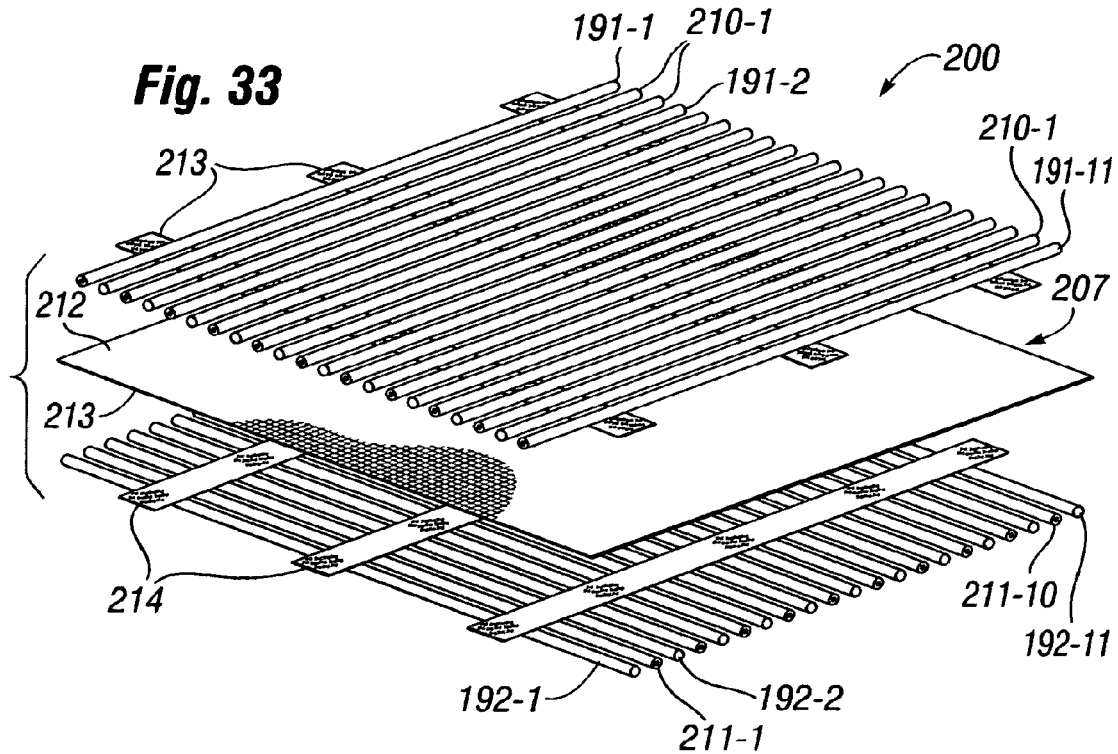
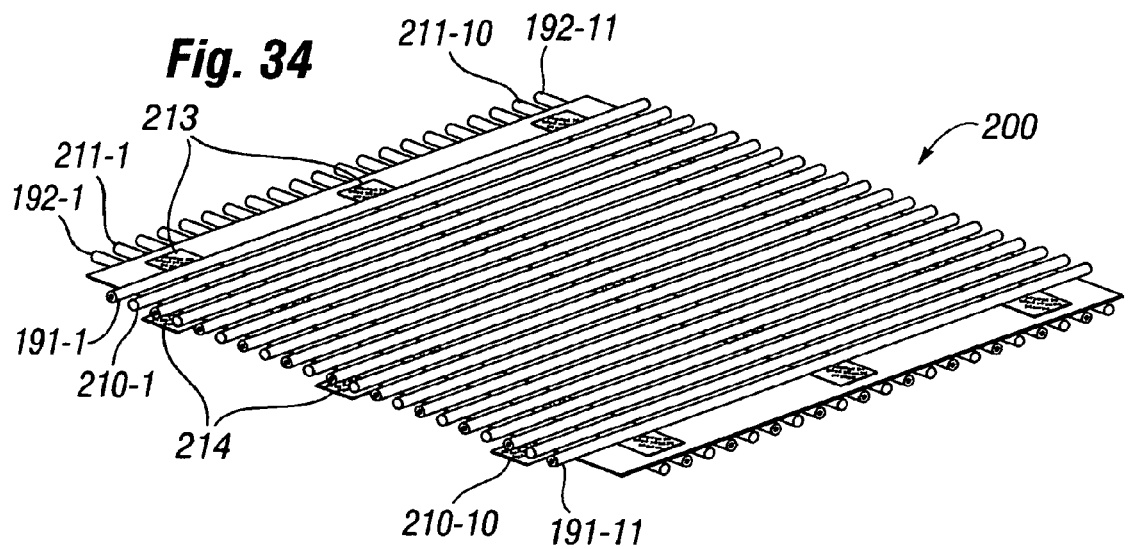

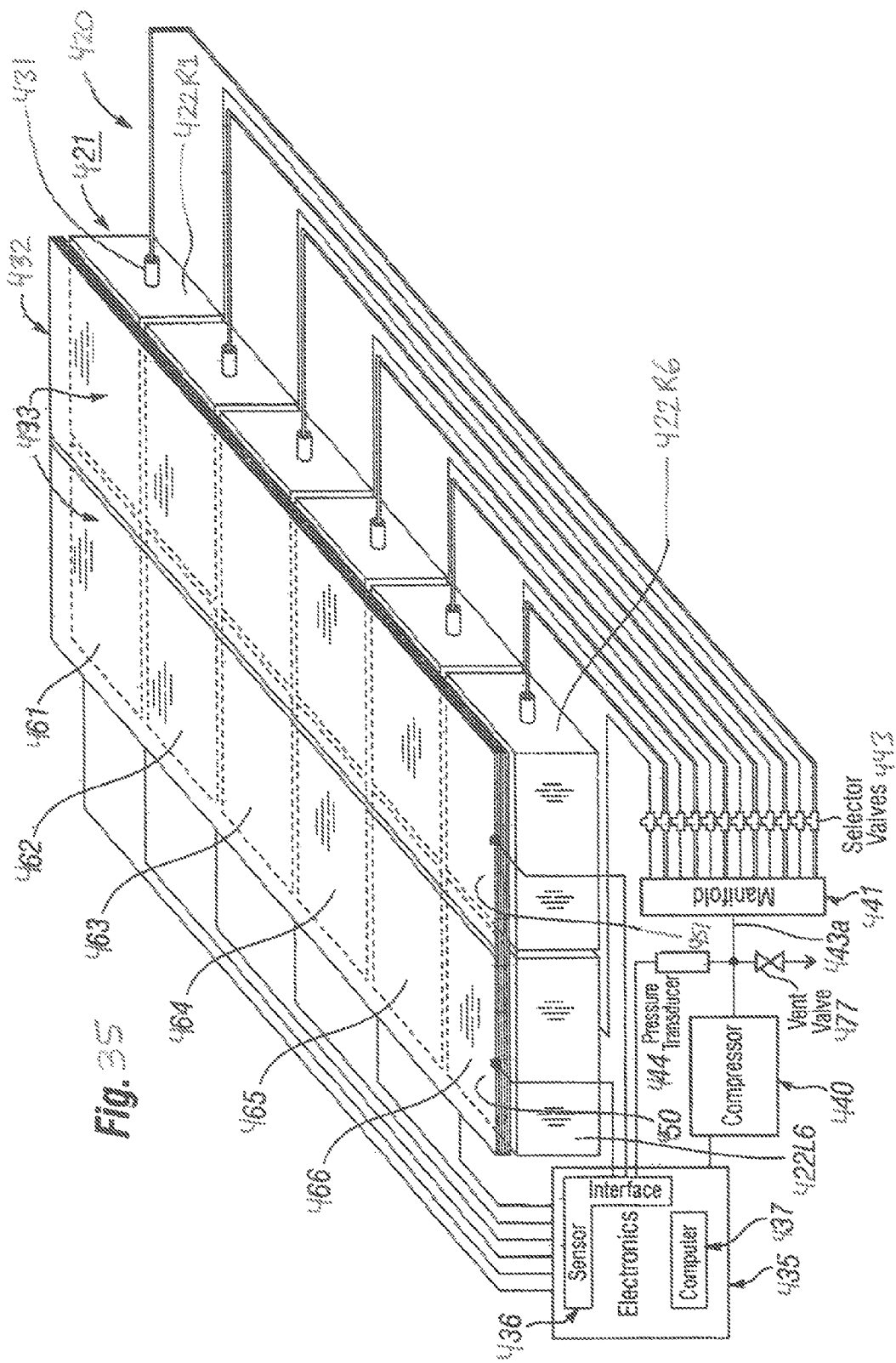

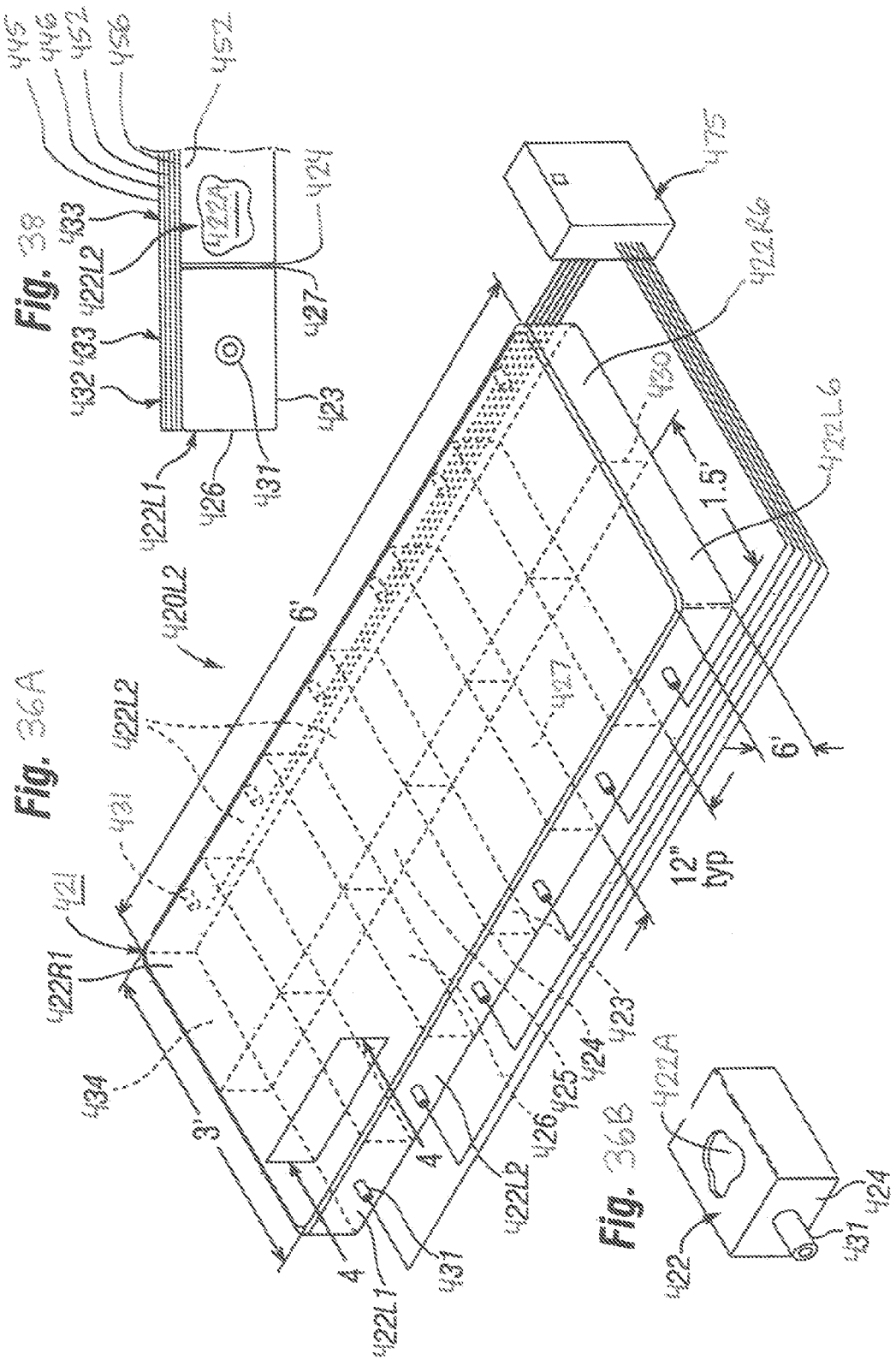

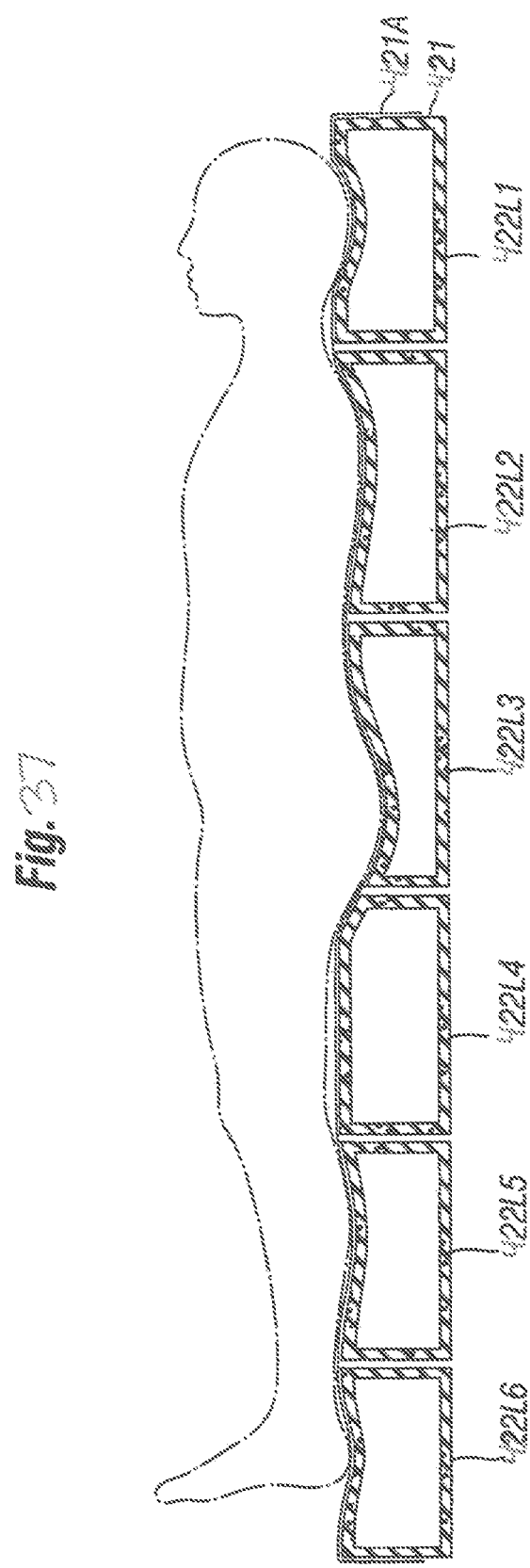

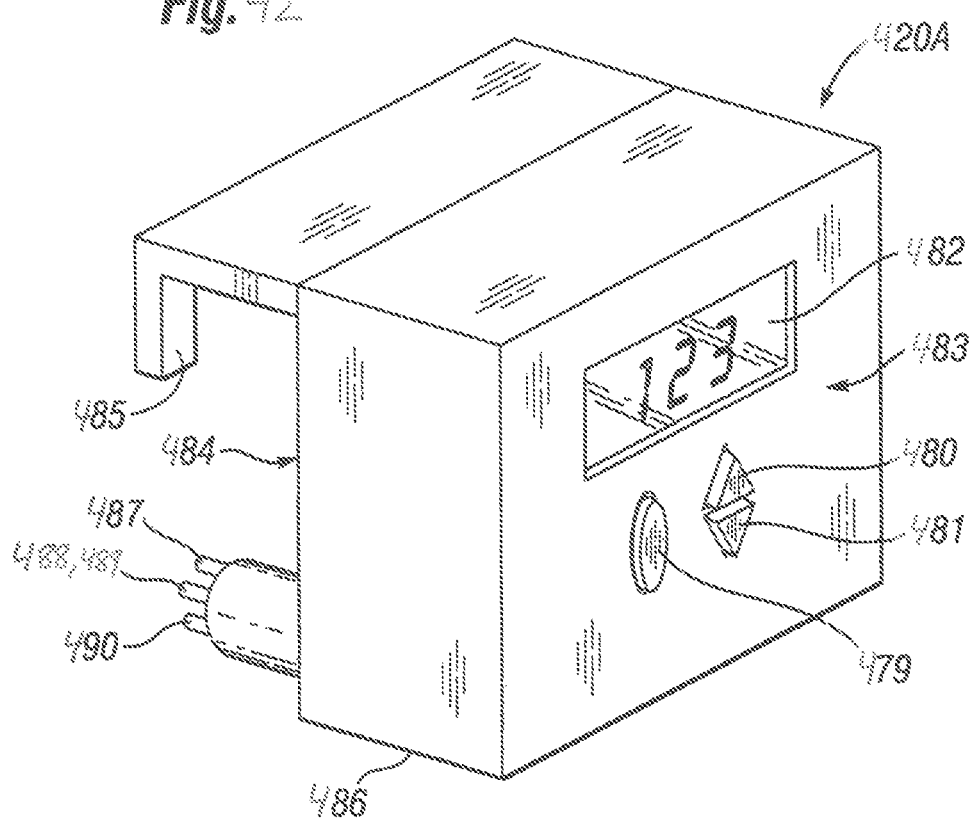

FORCE SENSING SHEET

CROSS-REFERENCE TO RELATED APPLICATIONS

This application is a continuation of, and claims priority to, U.S. patent application Ser. No. 13/453,461 filed Apr. 23, 2012 by Geoffrey Taylor and entitled ELASTICALLY STRETCHABLE FABRIC FORCE SENSOR ARRAYS AND METHODS OF MAKING; which in turn is a continuation of U.S. patent application Ser. No. 12/380,845 filed Mar. 5, 2009 by Geoffrey Taylor, and entitled ELASTICALLY STRETCHABLE FABRIC FORCE SENSOR ARRAYS AND METHOD OF MAKING. This application is also a continuation-in-part of, and claims priority to, U.S. patent application Ser. No. 12/075,937 filed Mar. 15, 2008 by Geoffrey Taylor and entitled ADAPTIVE CUSHION METHOD AND APPARATUS FOR MINIMIZING FORCE CONCENTRATIONS ON A HUMAN BODY.

BACKGROUND OF THE INVENTION

A. Field of the Invention

The present invention relates to transducers or sensors used to measure forces or pressures exerted on a surface.

B. Description of Background Art

Whenever a human body is supported by an object such as a chair or bed, normal and shear forces produced in reaction to the weight of the individual are transmitted from the supporting surface through the skin, adipose tissues, muscles, etc. to the skeleton. The forces exerted on body parts by support surfaces, which are equal and opposite to body weight forces, can in some cases cause damage to tissues. Forces on body parts can compress internal blood vessels and occlude nutrients from the tissue, the product of the magnitude and duration of these forces determining whether tissue damage or morbidity will occur. The areas of the human body which are most at risk of developing tissue damage such as a pressure sore are: heel, ischial tuberosities, greater trochanter, occiput and sacrum.

Some prior art sensor arrays for sensing patient pressure have suffered from disadvantages. For example, with some prior art sensors arrays, if the array is used to measure pressures exerted on a human body by a very form-fitting, conformal wheelchair seat cushion or extremely low pressure bed mattress or cushion, the array will often interfere with the function of the cushion or bed support surface, and give erroneous force measurements which are used to map the way the bed or chair supports a person. Such errors result from a "hammocking" effect, in which a flexible but not drapable sensor array deployed between fixed support positions cannot conform precisely to the shape of a patient. This effect can occur for example, using sensor arrays that use wire core sensing elements which make the arrays essentially non-stretchable. The lack of conformability of a sensor array alters the way a cushion or bed supports a patient, and also frequently results in forces or pressures exerted on individual sensors in the array being larger than a patient would actually encounter in the absence of the sensor array.

Another situation in which existing force sensor arrays for measuring and mapping forces exerted on human body parts are less than satisfactory occurs when attempting to make such measurements in a non-obtrusive, non-interfering manner on body parts which have complex shapes such as the feet.

Still further, in some prior art sensor arrays, it can be difficult to measure the resistance of sensor elements in an array using matrix addressing of the sensor elements. The difficulty results from the fact that the electrical resistances of all the non-addressed sensor elements in an array shunts the resistance of each addressed sensor element, resulting in cross-talk inaccuracies in measurements of individual sensor element resistances.

SUMMARY OF THE INVENTION

Briefly stated, the present invention comprehends novel pressure or force sensing transducers which include individual force sensing elements that are arranged in a planar array on or within a substrate consisting of a thin, flexible polymer sheet or a thin sheet of woven or non-woven fabric.

According to one embodiment of the invention, a flexible force sensing array is provided that includes an elastically stretchable sheet, a plurality of first conductive paths, a layer of sensing material, a layer of semiconductive material, and a plurality of second conductive paths. The first conductive paths are supported on the elastically stretchable sheet. The layer of sensing material is positioned in contact with the first conductive paths and the layer of sensing material has an electrical characteristic that varies in response to physical forces exerted on it. The layer of semiconductive material is positioned in contact with the layer of sensing material on a side of the layer of sensing material opposite the plurality of first conductive paths. The plurality of second conductive paths are positioned in contact with the layer of semiconductive material on a side of the layer of semiconductive material opposite the layer of sensing material.

According to another embodiment, a flexible force sensing array is provided that includes a first elastically stretchable sheet, a plurality of first conductive paths, an intermediate elastically stretchable sheet, a layer of semiconductive material, a second elastically stretchable sheet, and a plurality of second conductive paths. The plurality of first conductive paths are supported on the first elastically stretchable sheet and are parallel to each other. The intermediate elastically stretchable sheet is positioned in contact with the first elastically stretchable sheet and includes sensing material thereon that has an electrical characteristic that varies in response to applied physical forces. The layer of semiconductive material is positioned in contact with the intermediate elastically stretchable sheet to thereby form with the sensing material a PN junction. The plurality of second conductive paths are supported on the second elastically stretchable sheet and are in electrical contact with the semiconductive material. The second conductive paths are parallel to each other and transverse to the first conductive paths.

According to other embodiments, the sensing material is a piezoresistive material. The piezoresistive material may be supported by an elastically stretchable substrate. The elastically stretchable substrate may be made at least partially of nylon. The first and second elastically stretchable sheets may both be made from woven fabric. The woven fabric is nylon in one embodiment.

The semiconductive layer may be coated onto the layer of sensing material and include a metallic oxide. In some embodiments, the metallic oxide may include copper oxide.

A cover sheet may be included in some embodiments that is made from an elastically stretchable material. In some embodiments, the cover is a polyurethane or polyvinyl chloride.

BRIEF DESCRIPTION OF THE DRAWINGS

FIG. 3 is a partly broken-away, upper perspective view of a second, two-layer embodiment of a piezoresistive thread pressure sensor array, in which the central piezoresistive layer shown in the basic embodiment of FIGS. 1 and 2 is replaced by a piezoresistive coating on conductive threads of the sensor array.

FIG. 4 is a vertical transverse sectional or end view of the sensor array of FIG. 3, taken in the direction 4-4.

FIG. 8A is a fragmentary transverse sectional view of the sensor array of FIGS. 3 and 4 on a further enlarged scale, showing the disposition of row and column piezoresistive threads to form force sensing elements, with no external force applied to the array.

FIG. 8B is a view similar to that of FIG. 8A, but with a moderate normal force applied to the sensor elements.

FIG. 8C shows the sensor element with a larger external force applied thereto.

FIG. 9 is a partly broken-away perspective view of a three-layer embodiment of a piezoresistive threads pressure sensor array, which uses a pair of fabric outer substrates and a central piezoresistive layer.

FIG. 10 is a fragmentary view of the sensor array of FIG. 9 on an enlarged scale and showing a lower plan view of an upper horizontal row conductor part of the sensor array.

FIG. 11 is a fragmentary view of the sensor array of FIG. 9, on an enlarged scale and showing an upper plan view of a lower vertical column conductor part of the sensor array.

FIG. 22A is a schematic diagram showing the number of conductive lead-outs required to measure the resistance of individual sensor elements in a linear array.

FIG. 22B shows sensor elements which do not have to be in a linear arrangement.

FIG. 23 is a schematic diagram showing a reduced number of lead-outs for matrix addressing an array of sensor elements arranged in a matrix array, including, but not limited to, the sensor array of FIG. 39.

FIG. 24 is a schematic diagram showing sensor elements of the array of FIG. 23 modified to include a diode junction.

FIG. 25 is an upper perspective view of a force measuring sensor apparatus using two-layer sensor arrays of the type shown in FIG. 5.

FIG. 26 is a block diagram showing the sensor array of FIGS. 1 and 3 interconnected with signal processing and display circuitry to comprise a force measurement system.

FIG. 27B is a horizontal transverse sectional view of the sock of FIG. 27A.

FIG. 33 is an exploded perspective view of components of another embodiment of a force sensor array.

FIG. 34 is a perspective view of the sensor array of FIG. 33.

FIG. 35 is a partly diagrammatic perspective view of a body support cushion apparatus with adaptive body force concentration minimization according to the present intention.

FIG. 36A is a fragmentary upper perspective view of the apparatus of FIG. 35, showing a sensor array jacket of the apparatus removed from a mattress overlay cushion of the apparatus to thereby reveal individual air bladder cells of the mattress.

FIG. 36B is a fragmentary view of the mattress overlay of FIG. 36A, showing an individual air cell thereof.

FIG. 37 is a diagrammatic side elevation view of the apparatus of FIGS. 35 and 36, showing certain bladder cells thereof deflated to reduce support forces exerted on parts of a human body supported by the mattress overlay.

FIG. 38 is a vertical sectional view of the mattress of FIG. 36, taken in the direction of line 4-4.

FIG. 43 is a flow chart showing operation of the apparatus of FIG. 35.

DETAILED DESCRIPTION OF THE EMBODIMENTS

FIGS. 1-43 illustrate various aspects of elastically stretchable, conformable fabric force sensor arrays, and methods for making the arrays, according to the present invention.

Figure 1:
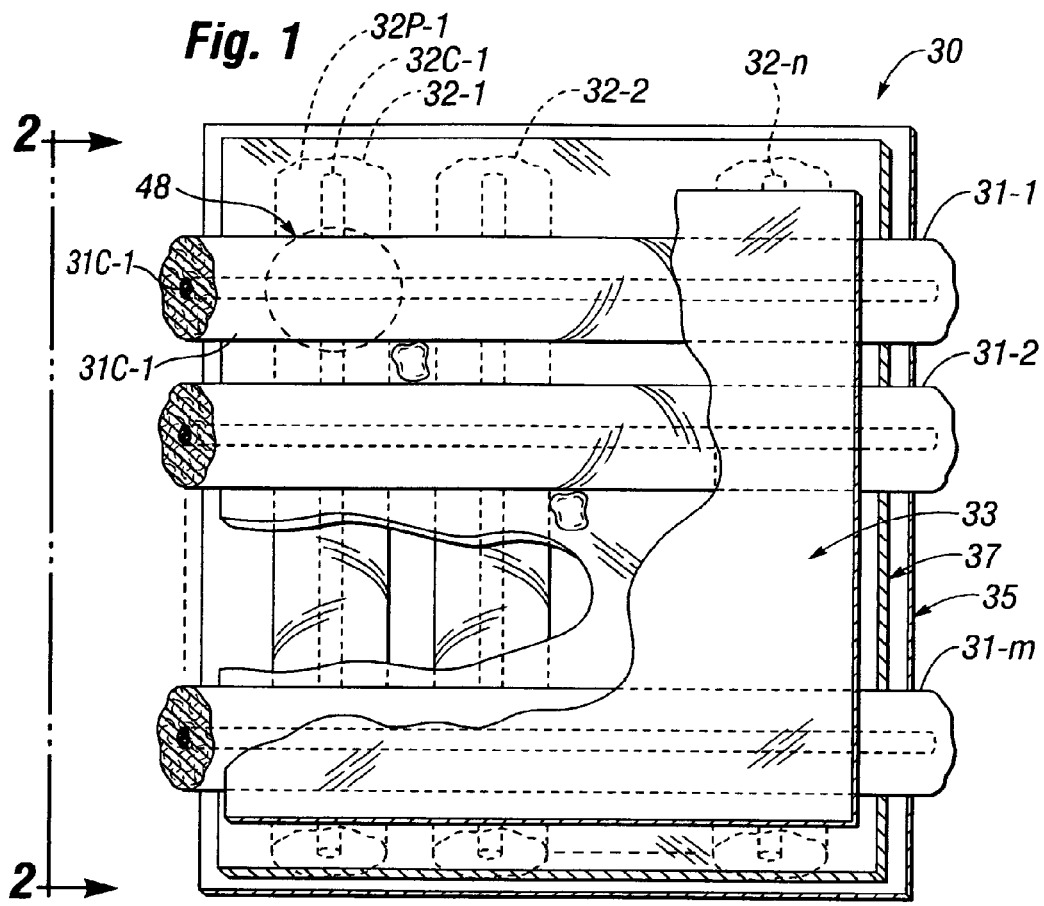
FIG. 1 is a partly broken away perspective view of a basic embodiment of a three-layer piezoresistive thread pressure sensor array according to one embodiment, which uses a pair of polymer film outer substrates and a central piezoresistive layer.
Figure 2:
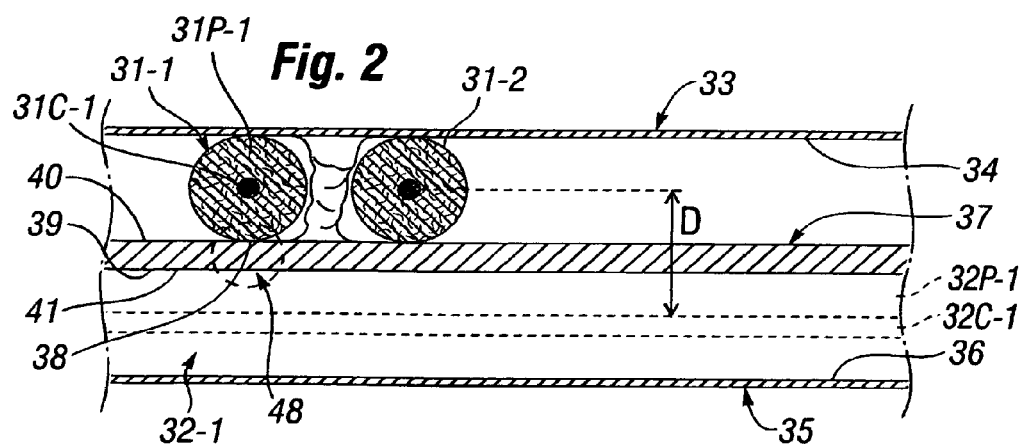
FIG. 2 is a vertical transverse sectional view or end view of the sensor array of FIG. 1 taken in the direction 2-2.

Referring first to FIGS. 1 and 2, a first, basic, three-layer embodiment of a force sensor array is shown.

As shown in FIGS. 1 and 2, a three-layer force sensor array 30 includes a plurality m of elongated, straight thin conductive row threads 31-1 through 31-m and a plurality n of elongated, straight thin, conductive column threads 32-1 through 32-n.

The electrically conductive row threads 31 and column threads 32 consist of an elastically stretchable monofilament or woven polymer core 31C, 32C, which has been treated to make the threads electrically conductive, as by silver plating the core to form coatings 31P, 32P on cores 31C, 32C, respectively.

One type of example embodiment of a sensor array 30 used row and column conductive threads 31, 32 made from silver plated nylon thread, 117/17 2 ply, catalog #A264, obtained from LESS EMF, 809 Madison Avenue, Albany, N.Y. 12208, USA. That conductive thread had a lineal resistivity of about 75 ohms per foot, and an elastic stretchability of about 1 percent, i.e., at least 10 times greater than that of a stainless steel wire of a similar diameter.

A second type of example embodiment of a sensor array uses row and column conductive threads made from silver plated stretchy nylon yarn, that plated yarn having the designation Shieldex, ®Lycra dtex 20, obtained from W. Zimmerman, GmbH & Co. K6, Riederstrasse 7, D-88171, Weiter-Simmerberg, Germany. That conductive thread had a lineal resistivity of about 500 ohms per foot. The elastic stretchability of that conductive yarn is greater than 30 percent, i.e., at least 300 times greater than that of a stainless steel wire of a similar diameter.

As shown in FIGS. 1 and 2, a row threads 31 and column threads 32 lie in parallel planes but are inclined with respect to one another, such as at an angle of ninety-degrees. In the example embodiment 30, row conductive threads 31 are fastened to the lower surface 34 on an upper substrate sheet 33, and column conductive threads 32 are fastened to the upper surface 36 of a lower substrate sheet 35.

As may be seen best by referring to FIG. 2, sensor array 30 includes a thin central lamination or sheet 37 made of a piezoresistive material. As shown in FIG. 2, opposed inner facing outer surfaces 38, 39 of row and column conductive threads tangentially contact upper and lower surfaces 40, 41, respectively, of central piezoresistive sheet 37. Thus, as shown in FIGS. 1 and 2, each crossing point or intersection of a row conductive thread 31 and a column conductive thread 32 forms a piezoresistive sensor element 48 which consists of a small portion of central piezoresistive sheet 37 that is electrically conductively contacted by a row conductive thread and a column conductive thread.

In example embodiments of sensor array 32, piezoresistive sheet 37 was fabricated by coating a stretchy, i.e., elastically stretchable thin Lycra-like fabric sheet with a piezoresistive material. A suitable fabric sheet, which forms a matrix for supporting the piezoresistive material, was a fabric known by the trade name Platinum, Milliken, Style #247579, obtained from the manufacturer, Milliken & Company, Spartenburg, S.C., USA. That fabric had a fiber content of 69 percent nylon and 31 percent Spandex, a thread count of about 88 threads per inch, and a thickness of 0.010 inch.

The piezoresistive material used to coat the fabric matrix is made as follows:

A solution of graphite, carbon powder, nickel powder and acrylic binder are mixed in proportions as required to obtain the desired resistance and piezoresistive properties. Silver coated nickel flake is used to achieve force response in the low force range of 0 to 1 psi, graphite is used for the mid range of 1 to 5 psi and Charcoal Lamp Black is used for high force range of 5 to 1000 psi. Following is a description of the substances which are constituents of the piezoresistive material:

Silver Coated Nickel Flake:
Platelets approximately one micron thick and 5 microns in diameter.
Screen Analysis (−325 Mesh) 95%.
Apparent Density 2.8.
Microtrac d50/microns 12-17.
Available from: Novamet Specialty Products Corporation, 681 Lawlins Road, Wyckoff, N.J. 07481
Graphite Powder:
Synthetic graphite, AC-4722T
Available from: Anachemia Science
4-214 De Baets Street
Winnipeg, MB R2J 3W6
Charcoal Lamp Black Powder:
Anachemia Part number AC-2155
Available from: Anachemia Science
4-214 De Baets Street
Winnipeg, MB R2J 3W6
Acrylic Binder:
Staticide Acrylic High Performance Floor Finish
P/N 4000-1 Ph 8.4 to 9.0
Available from: Static Specialties Co. Ltd.
1371-4 Church Street
Bohemia, N.Y. 11716

Following are examples of mixtures used to make piezoresistive materials having different sensitivities:

Example I for forces in the range of 0 to 30 psi:
200 ml of acrylic binder
10 ml of nickel flake powder
10 ml of graphite powder
20 ml of carbon black
Example II for forces in the range of 0-100 psi:
200 ml of acrylic binder
5 ml of nickel flake powder
5 ml of graphite powder
30 ml of carbon black Example III for forces in the range of 0-1000 psi
200 ml of acrylic binder
1 ml of nickel flake powder
1 ml of graphite powder
40 ml of carbon black The fabric matrix for piezoresistive sheet 37 is submerged in the piezoresistive coating mixture. Excess material is rolled off and the sheet is hung and allowed to air dry.

Upper and lower substrate sheets 33, 34 are made of a thin, flexible insulating material, such as 0.002 inch thick polyurethane or polyvinyl chloride (PVC). In one embodimenty, the substrate sheets 33, 34 are made of an elastomeric material which has a relatively high degree of elastic stretchability, so that sensor array 30 is readily stretchable and conformable to the surface of an irregularly-shaped object. It can be appreciated, however, that conductive threads 31, 32 should also be elastically stretchable to facilitate stretchability of sensor array 30. This is because conductive threads 31, 32 are affixed to substrate sheet 33, 34, respectively, by, for example, blobs of adhesive 42, as shown in FIG. 2. Piezoresistive sheet 37 is also fixed to upper and lower substrate sheets 33, 34 by blobs of glue 42.

FIGS. 6A-6C illustrate how the arrangement of row and column conductive threads 31, 32, in combination with central piezoresistive layer 37 of sensor array 30 shown in FIGS. 1 and 2, form individual force sensing elements 48. Each force sensor element 48 is located at the cross-over or intersection point 49 of a row conductive thread, e.g., 31-1, 31-2, ... 31-*m*, with a column conductive thread, e.g., 32-1, 32-2, ... 32-*n*, for a MXN matrix of sensor elements. Thus, individual sensor elements may be identified by the nomenclature 48-XXX-YYY, where XXX denotes row number and YYY denotes column number.

As shown in FIGS. 2 and 6A, with no external force applied to sensor array 30, at each cross-over point 49 of a row conductive thread 31 and a column conductive thread 32 of sensor array 30, there is an upper electrically conductive tangential contact region 43 between central piezoresistive layer 37 and the upper conductive row thread, and a lower electrically conductive tangential contact region 44 between the piezoresistive layer and the lower, column conductive thread.

With no external force applied to sensor array 30, the electrical resistance between a row conductive thread 31 and column conductive thread 32, which consists of the series resistance of upper contact region 43, lower contact region 44, and the effective resistance of piezoresistive material 45 of piezoresistive layer 37 between the upper and lower contact regions is relatively high. The relatively high resistance results from the fact that in this case, tangential contact regions 43 and 44 are relatively small, and the thickness of uncompressed piezoresistive volume 45 is at its maximum value. However, as shown in FIGS. 6B and 6C, when sensor array 30 is placed on a supporting surface S and a normal force N of increasing magnitude is applied to upper surface 47 of the sensor array 30, the electrical resistance between a row conductive thread 31 and a column conductive thread 32 decreases, as will now be described.

Referring still to FIGS. 2 and 6A, it may be seen that with no external force applied to sensor array 30, tangential contact regions 43, 44 between row and column conductive threads 31, 32 and central piezoresistive layer 37 are relatively small, since the threads have a circular outer cross-sectional shape, which tangentially contacts flat planar surfaces of the piezoresistive layer. Under these circumstances, the small sizes of contact regions 43, 44 results in relatively high electrical resistance between central piezoresistive layer 37 and row and column conductive threads 31, 32. Moreover, with central piezoresistive layer 37 uncompressed, its thickness and hence resistance are at a maximum value.

FIGS. 6B and 6C illustrate the effects of increasing external normal forces or pressures exerted on sensor array 30. As shown in FIGS. 6B and 6C, sensor array 30 is placed with its lower surface 46 supported on a surface S and a force N is exerted perpendicularly downwards on upper surface 47 of the array, resulting in a reaction force U being exerted upwardly by supporting surface S on lower surface 46 of the array. Since central piezoresistive layer 37 is resiliently deformable, the compressive force on it decreases the thickness T of the part of the layer between a row conductive thread 31 and a column conductive thread 32. This reduction in path length through piezoresistive layer 37 between a row conductive thread 31 and a column conductive thread 32 causes the electrical resistance R between the threads to decrease in value.

Figure 7:
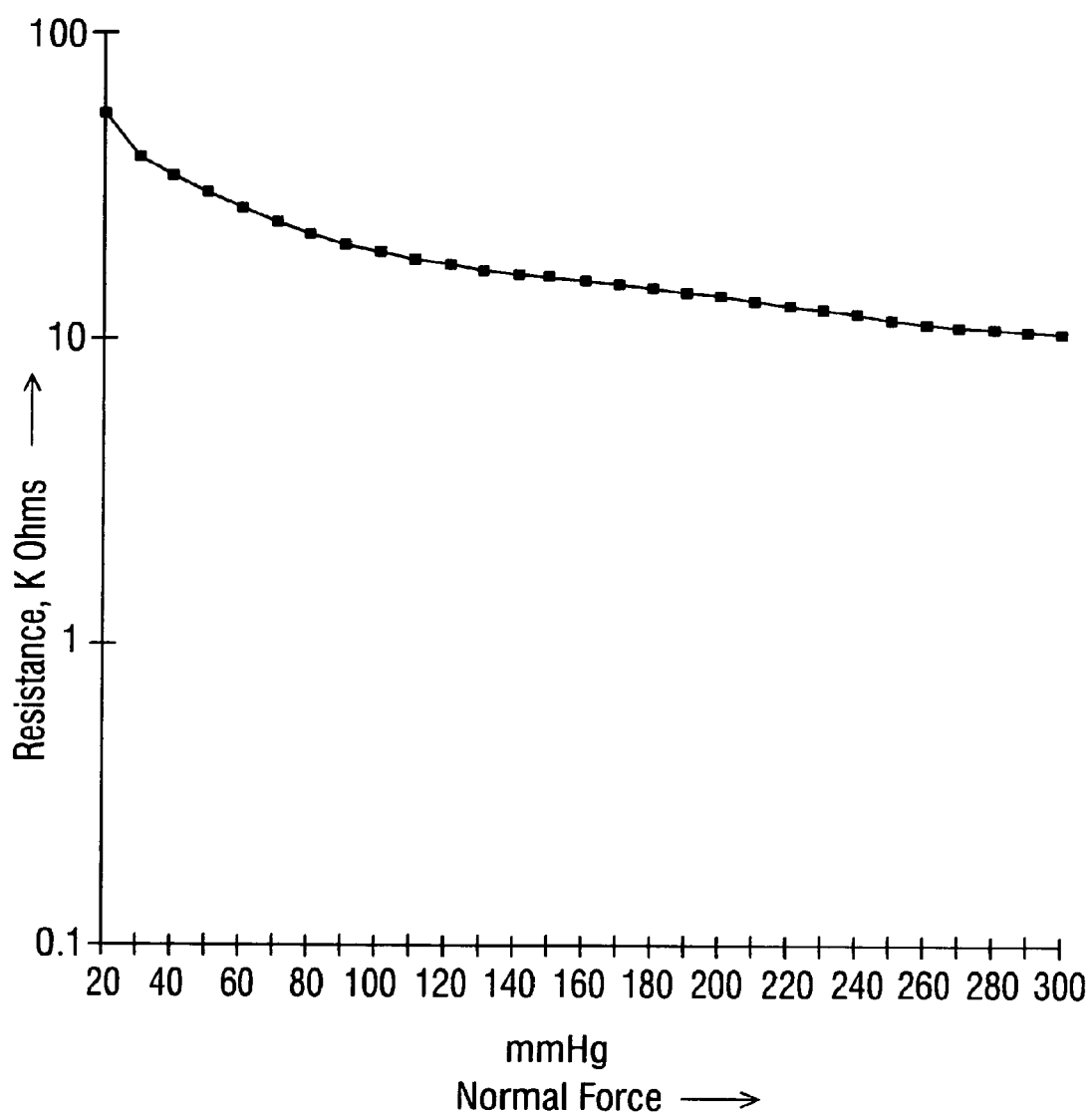
FIG. 7 is a graph showing electrical resistance plotted as a function of force or pressure exerted on sensor elements of the sensor arrays shown in FIGS. 1 and 3.

For moderate values of normal force N, as shown in FIG. 6B, resilient deformation of central piezoresistive layer 37 is relatively small, resulting in a relative small reduction in electrical resistance R between the threads. Larger forces N exerted on sensor array 30 cause a larger deformation of the central piezoresistive layer, as shown in FIG. 6C, resulting in a larger percentage reduction in resistance R. FIG. 7 illustrates in a general way the reduction in electrical resistance measurable between a row conductive thread 31 and a column conductive thread 32, as a function of normal force or pressure exerted on array 30 at these points.

FIGS. 3 and 4 illustrate another embodiment 50 of a piezoresistive thread pressure sensor array in which the central piezoresistive layer shown in FIGS. 1 and 2 and described above is replaced by a piezoresistive coating on either, or both, row conductive threads 51 and column conductive threads 52.

Sensor array 50 is facially similar to sensor array 20 disclosed and shown in FIGS. 1 and 2 of U.S. Pat. No. 6,543,299, but differs from that sensor array in important ways. Thus, row and column piezoresistive threads 51, 52 of sensor array 50 are made of elastically stretchable polymer cores 51C, 52C which have been treated by silver plating the cores to form on the threads electrically conductive coatings 51P, 52P, respectively. The coatings on either or both cores 51C, 52C are clad with a layer 51R, 52R, respectively, of a material which has a piezoresistive characteristic. The piezoresistive material used to form cladding layers 51R, 52R on plated surfaces 51P, 52P of cores 51C, 52C, of piezoresistive conductive threads 51, 52 may have a composition similar to that described above for making piezoresistive sheet layer 37.

A method for making piezoresistive sensor threads by cladding conductive threads with a layer of a piezoresistive material includes preparing a slurry of piezoresistive material having a composition described in examples 1, 2 and 3 above. A highly conductive polymer thread, such as silver plated nylon thread 117/17 2 ply, Cat#124 available from LESS EMF Inc., 804 Madison Avenue, Albany, N.Y. 12208, is then immersed in a container holding the slurry, for a period of about 10 seconds. The end of a thread which has been immersed is withdrawn from the container, and while it is still wet, drawn through a circular aperture through a scraper plate.

In an example embodiment, a conductive thread having a core diameter of 0.25 mm and wet-coated diameter in the range of about 0.4 mm to 0.5 mm was drawn through a #360 scraper having a diameter of 0.45 mm, thus resulting in a wet scraped diameter of about 0.45 mm. The scraped thread was then fed through a stream of air heated to a temperature of 70 degrees C. at a linear travel speed of 100 mm/minute for a period of 5 minutes, to thus form a solidified coating having a diameter of about 0.4 mm.

As shown in FIGS. 3 and 4, piezoresistive row and column threads 51, 52 are fastened to upper and lower substrate sheets 63, 65, by suitable means such as adhesive blobs 74. Substrate sheets 63, 64 are made of a thin, flexible material such as 0.003 inch thick elastomeric polyurethane or polyvinyl chloride (PVC) that has a relatively high degree of elasticity.

FIGS. 3 and 8A-8C illustrate how the arrangement of row and column piezoresistive threads 51, 52 of sensor array 50 form individual force sensing elements 69. In response to progressively larger compressive normal forces, piezoresistive cladding layers 51R, 52R on row and column conductive core threads 51C, 52C are progressively compressed into oval cross-sectional shapes of smaller diameter. Thus, as shown in FIGS. 8A-8C, the electrical resistance of each sensor element 70 decreases in inverse proportion to applied pressure, as shown in FIG. 7.

Figure 5:
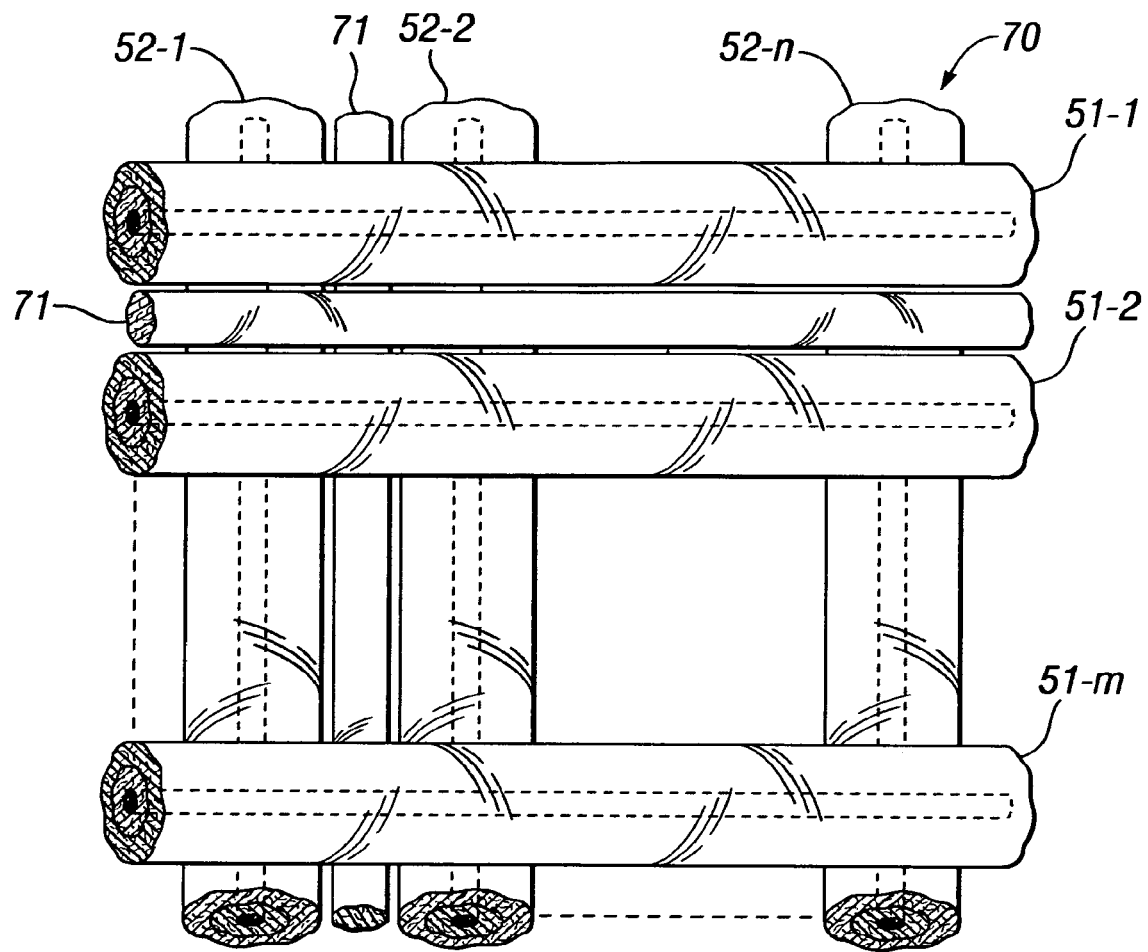
FIG. 5 is a fragmentary perspective view of a modification of the sensor array of FIGS. 1 and 3 in which adjacent pairs of more closely packed row and column conductor threads are spatially and electrically isolated from each other by non-conductive threads.
Figure 6:
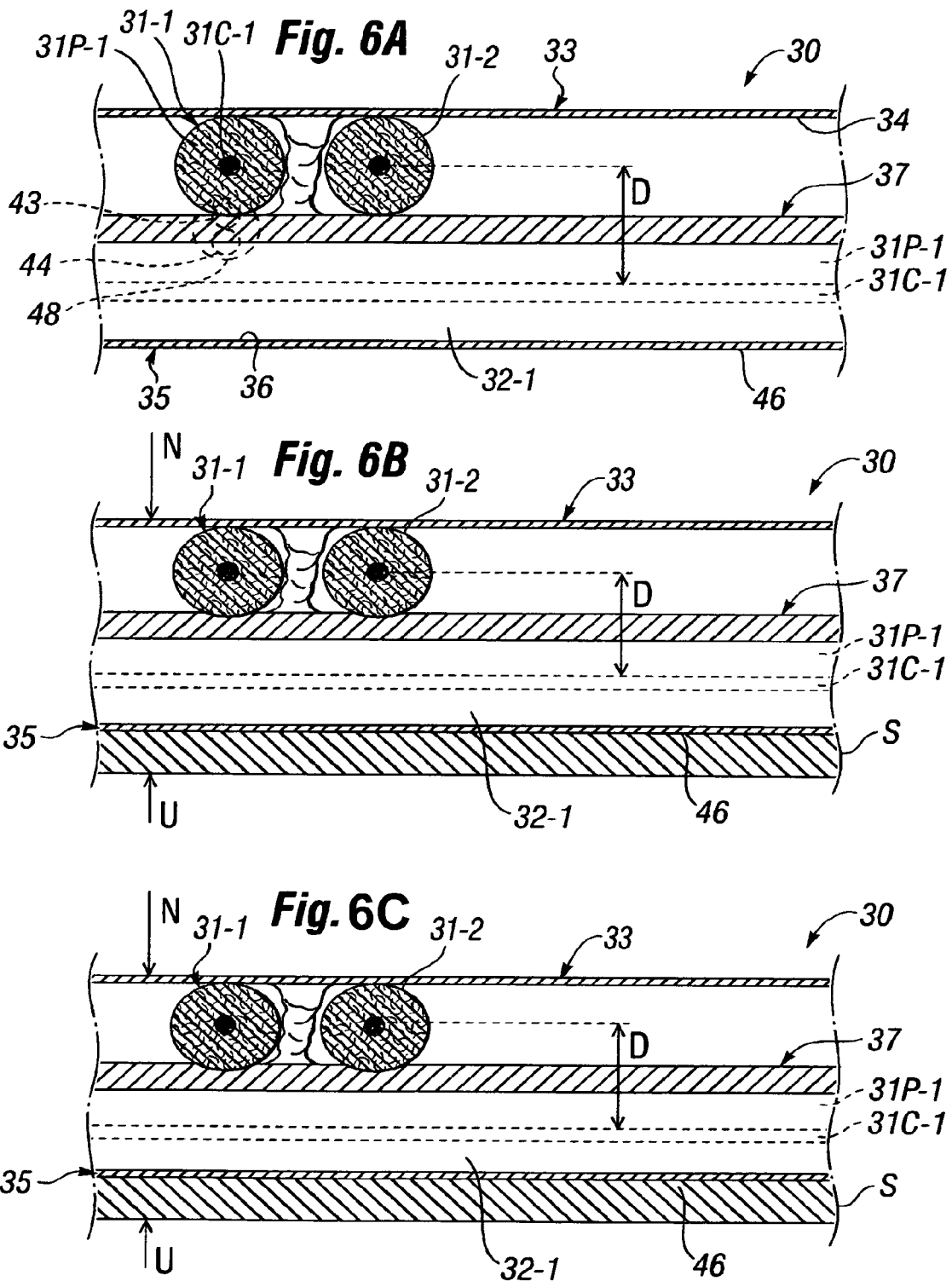
FIG. 6A is a fragmentary transverse sectional view of the sensor array of FIGS. 1 and 2, on a further enlarged scale, showing the disposition of crossed row and column conductive threads contacting a central piezoresistive layer to form force sensing elements, with no external force applied to the elements.
FIG. 6B is a view similar to that of FIG. 6A, but with a moderate normal force applied to the sensor elements.
FIG. 6C shows the sensor elements with a larger external force applied thereto.

FIG. 5 illustrates a modification 70 of the sensor arrays shown in FIGS. 1 and 3 and described above. Modified sensor array 70 may alternatively employ the three-layer construction of sensor array 30 shown in FIG. 1, or the two-layer construction of sensor array 50 shown in FIG. 3. The modification consists of fabricating sensor array 70 with electrically insulating material between adjacent rows and/or columns of conductive threads. Thus, for example, the modification 70 of two-layer sensor 50 shown in FIG. 3 includes elongated insulating threads 71, made for example of 0.012 inch diameter polyester disposed between each pair of adjacent row conductive threads 51 and each pair of adjacent column conductive threads 52.

The insulating threads 71 are secured in place by any suitable means, such as adhesively bonding the threads to substrate sheets 63, 65 (see FIGS. 2 and 4). This constructing enables sensor array 70 to be substantially wrinkled or otherwise deformed to conform to an irregularly shaped surface, without the possibility of pairs adjacent row or column conductive threads 51 or 52 contacting one another to thus cause an electrical short circuit which would result in erroneous sensor element resistance measurements and force determinations. Optionally, insulation between adjacent pairs of row and column conductive threads could be applied by lightly spraying an aerosol insulation acrylic paint to hold the conductive threads in place.

FIGS. 9-12 illustrate a three-layer embodiment 80 of a piezoresistive thread force sensor array. Sensor array 80 is similar to the basic embodiment 30 of sensor array shown in FIGS. 1-2 and described above. However, sensor array 80 uses upper and lower substrate sheets 83, 85 which are made of woven fabric rather than polymer films. This construction, in conjunction with the use of stretchy conductive row and column threads 81, 82 made of plated nylon or Lycra cores, results in a sensor array that is even more flexible, elastically stretchable and drapable than sensor array 30.

As may be seen best by referring to FIG. 10, sensor array 80 includes a plurality of parallel, laterally spaced apart conductive row threads 81 which are fastened to the lower surface 84 of upper fabric substrate sheet 83. The row conductive threads 81 are fastened to lower surface 84 of upper substrate sheet 83 by any suitable means. In one embodiment, as shown in FIG. 10, each row conductive thread 81 is fastened to a substrate sheet by sewing the thread to fabric substrate sheet 83 by a smaller diameter, non-conductive thread 90 arranged in an elongated zig-zag stitching pattern. In an example embodiment, threads 90 consisted of 0.005-0.010 inch diameter, 100% polyester woven thread. For greater strength required for sensor arrays used to measure larger forces, threads 90 may optionally be monofilaments.

In an example embodiment of a sensor array 80, upper and lower substrate sheets 83, 85 were made from a light-weight, elastically stretchable fabric, both of the two following fabrics were tested and found suitable for substrate sheets 83, 85. (1) Milliken "Mil/glass" brand, Style #247579, composed of 69% nylon, 31% spandex, and having a weight of 1.8 oz./sq. yd. (2) Milliken "Interlude" brand, product #247211, composed of 82% nylon, 18% Lycra, and having a weight of 3.2-3.4 oz. Per sq. yd. Both of the foregoing fabrics are available from Milliken & Company, 23 Fiddler's Way, Lafayette, N.J. 07848.

As shown in FIG. 11, lower column conductive threads 82 are fastened to the upper surface 86 of lower fabric substrate sheet 85 by non-conductive threads 91 of the same type as non-conductive threads 90 and in the same zig-zag stitching manner.

Figure 12:
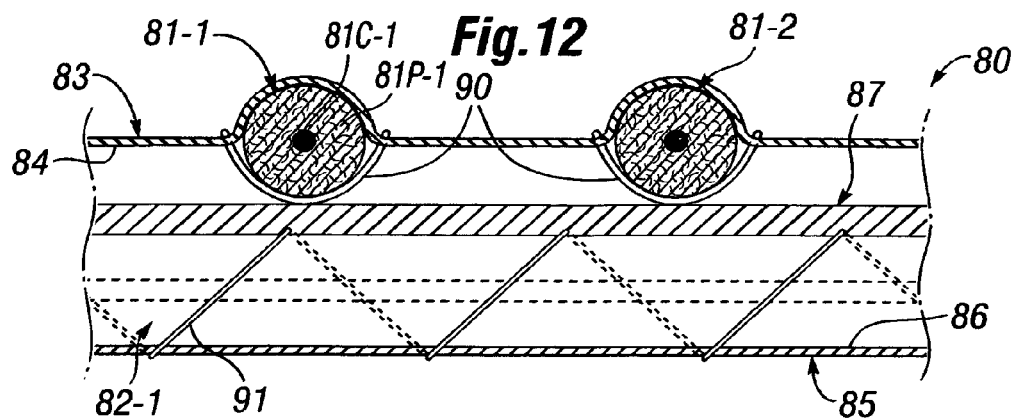
FIG. 12 is a vertical transverse sectional view, of the sensor array of FIG. 9, taken in the direction 12-12.

As shown in FIGS. 9 and 12, three-layer fabric substrate sensor array 80 includes a central piezoresistive sheet 87, which may have a composition and construction similar to that of central piezoresistive sheet 37 of sensor array 30 described above.

Figure 13A:
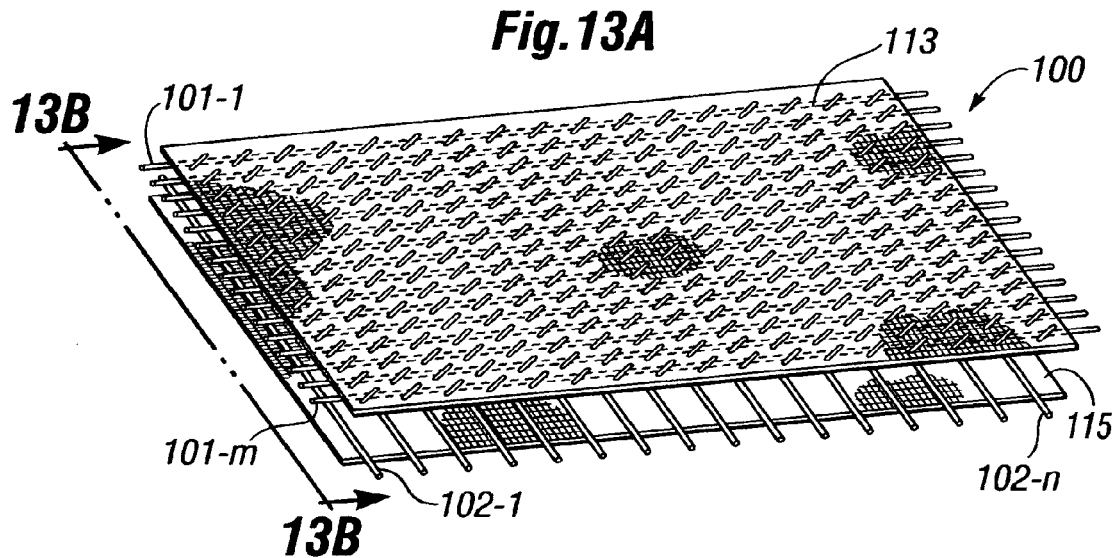
FIG. 13A is a partly broken-away, exploded upper perspective view of a fourth, two-layer piezoresistive thread pressure sensor array using fabric substrates in which the central piezoresistive layer of the embodiment shown in FIG. 9 is replaced by a piezoresistive coating on conductive threads of the sensor array.
Figure 13B:
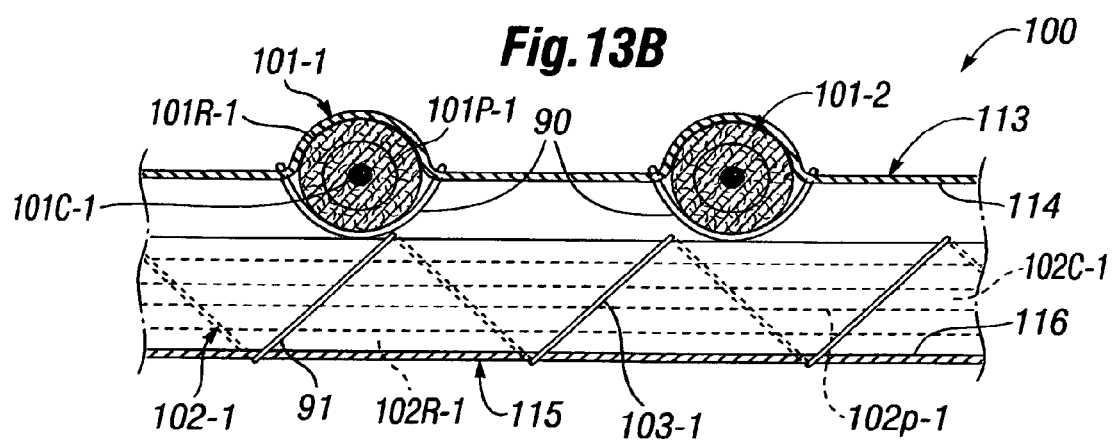
FIG. 13B is a vertical transverse sectional view of the sensor array of FIG. 13A, taken in the direction 13B-13B.

As may be seen best by referring to FIG. 13B, upper, row piezoresistive threads 101 are attached to lower surface 114 of upper fabric substrate sheet 113 by insulating sewn threads 90 arranged in zig-zag stitches. Similarly, lower, column piezoresistive threads 102 are attached to the upper surface 116 of lower substrate sheet 115 by sewn threads 91 arranged in zig-zag stitches.

FIGS. 13A and 13B illustrate another two-layer embodiment 100 of a piezoresistive thread force sensor array. Sensor array 100 is similar to sensor array 80. However, in sensor array 100, conductive row and column threads 81, 82 are replaced by piezoresistive threads 101, 102 which have the same characteristics as piezoresistive threads 51, 52 of the two-layer polymer film substrate sensor array 50 shown in FIGS. 3 and 4 and described above. This construction eliminates the requirement for the central piezoresistive sheet 87 of three-layer fabric sensor array 80 described above.

Figure 14:
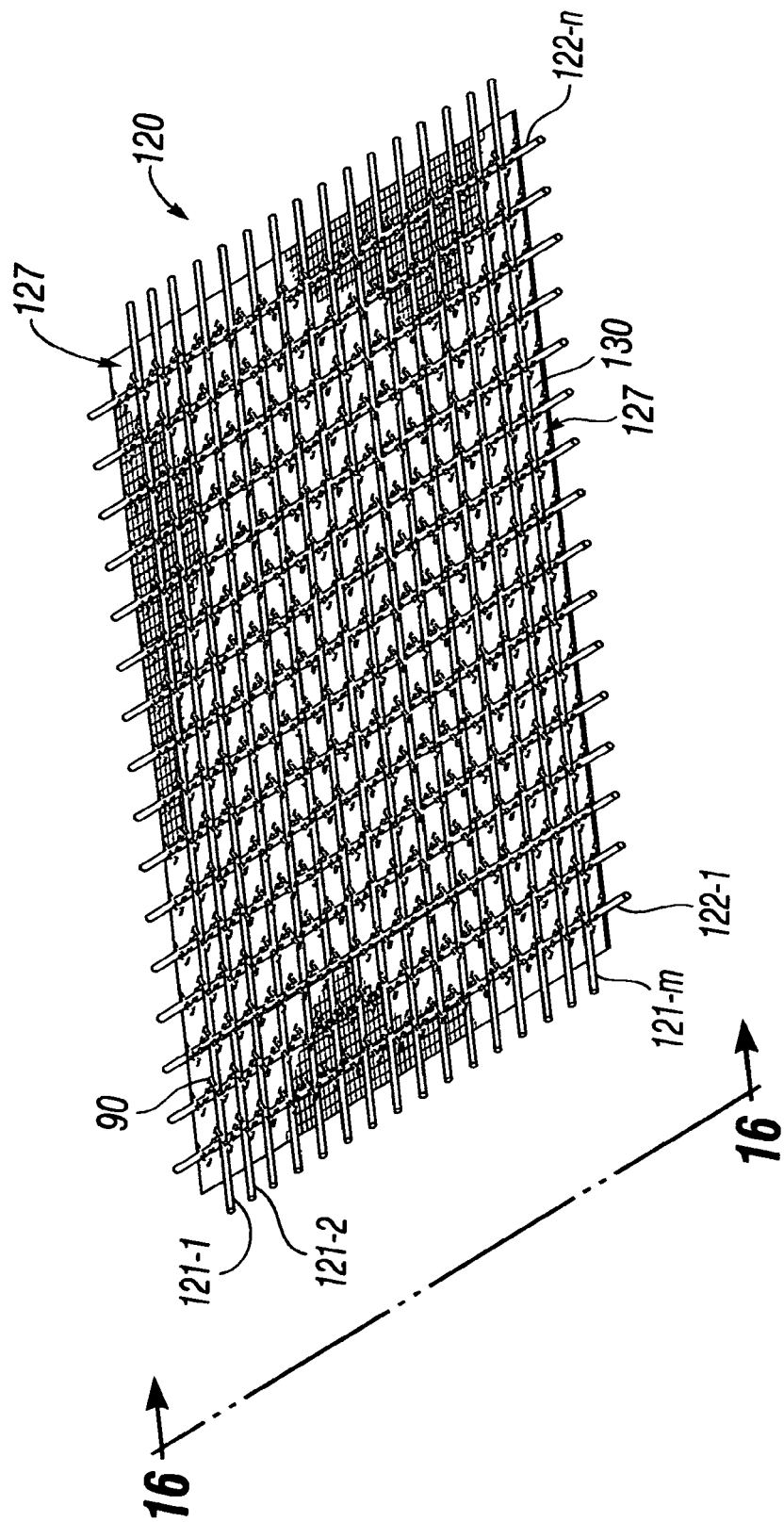
FIG. 14 is a partly broken-away upper perspective view of a fifth, single layer embodiment of a piezoresistive thread pressure sensor array which has a single fabric substrate, in which both row and column piezoresistive threads are fastened to the same side of a single insulating substrate sheet.
Figure 15:
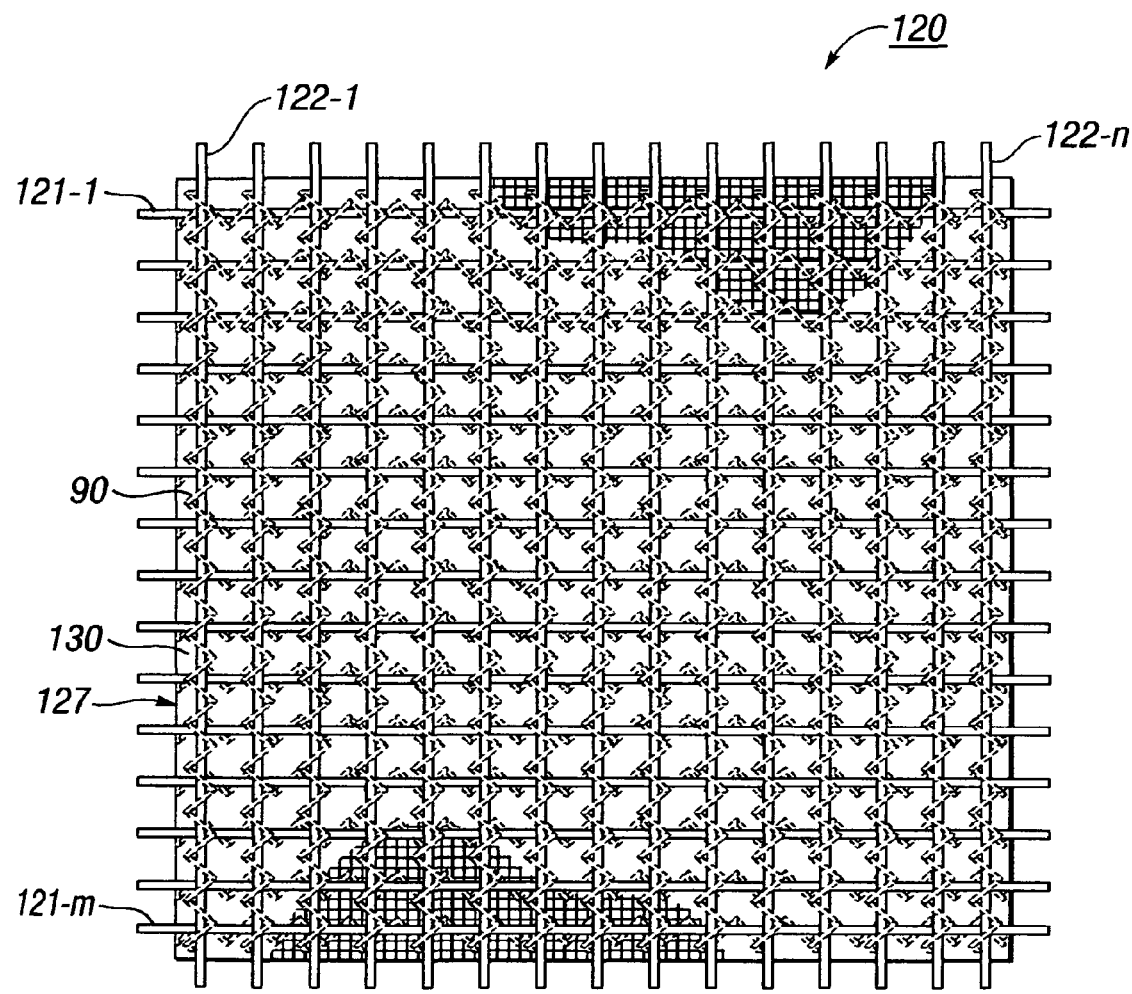
FIG. 15 is an upper plan view of the sensor array of FIG. 14.
Figure 16:
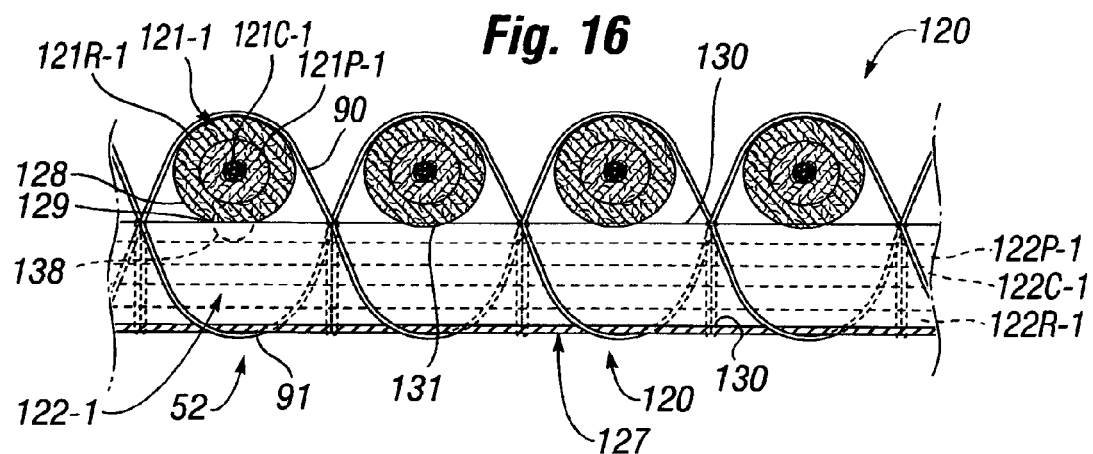
FIG. 16 is a vertical transverse sectional view of the sensor array of FIG. 14, taken in the direction 16-16.

FIGS. 14-16 illustrate a fifth, single layer embodiment 120 of a force sensor array in which row and column piezoresistive threads are attached to a single side of a single insulating fabric substrate sheet 127.

As shown in FIGS. 14-16, single layer fabric force sensor array 120 has a single substrate sheet 127 which is made from a light-weight, elastically stretchable fabric. Both of the two following fabric were listed and found suitable for making substrate sheet 127. (1) Milliken "Millglass" brand, Style #247579, composed of 69% nylon, 31% spandex, and having a weight of 1.8 oz./sq. yd., and (2) Milliken "Interlude" brand, product #247211, composed of 82% nylon, 18% Lycra, and having a weight of 3.2-3.4 oz. Per sq. yd. Both of the foregoing fabrics are available from Milliken & Company.

A plurality of parallel, laterally spaced apart column piezoresistive threads 122 are fastened to the upper surface 130 of the substrate sheet. The column piezoresistive threads are made from silver-plated nylon thread, Catalog #A-264 obtained from LESS EMF, or from silver-plated stretchy nylon yarn, both of which are described in detail above in conjunction with the description of sensor array 30.

In one embodiment of single fabric substrate sheet sensor array 120, each column piezoresistive thread 122 is fastened to substrate sheet 127 by a smaller diameter, non-conductive thread 91 arranged in an elongated zig-zag stitching pattern. In an example embodiment, threads 91 consisted of 0.005-0.010 diameter, 100% polyester.

As shown in FIGS. 14, 15 and 16, sensor array 120 includes a plurality of parallel, laterally spaced apart piezoresistive row threads 121 which are also fastened to the upper surface 130 of substrate sheet 127. As shown in FIG. 16, m row piezoresistive threads 121 are fastened to substrate sheet 127 by non-conductive threads 90 of the same type as threads 91 and in the same zig-zag stitching manner.

As shown in FIG. 16, opposed inner facing outer surface 128, 129 of row and column piezoresistive threads 121, 122 tangentially contact each other. Thus, as shown in FIGS. 14-16, each crossing of a row piezoresistive thread 121 with a column piezoresistive thread 122 forms a piezoresistive sensor element 138 which consists of a small portion of piezoresistive coatings of a row and column piezoresistive thread tangentially contacting one another.

Figure 17:
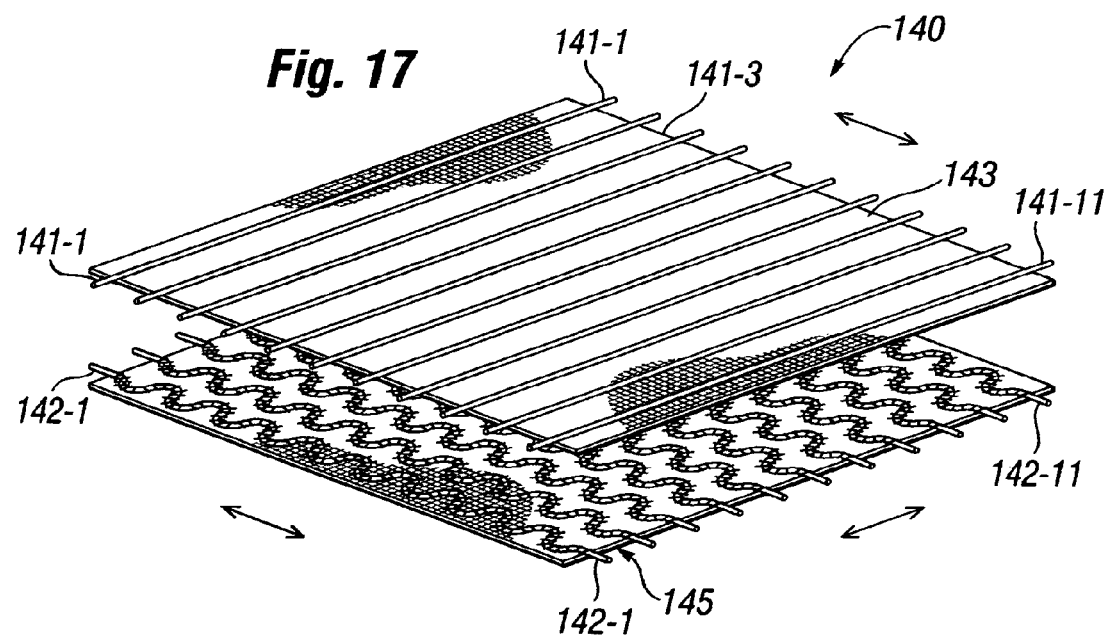
FIG. 17 is partly broken-away, exploded upper perspective view of a modification of the fabric substrate sensor arrays of FIG. 9, 13 or 14 in which lower column conductive threads of the sensor array are disposed in a sinuous arrangement on the fabric lower substrate panel.
Figure 18:
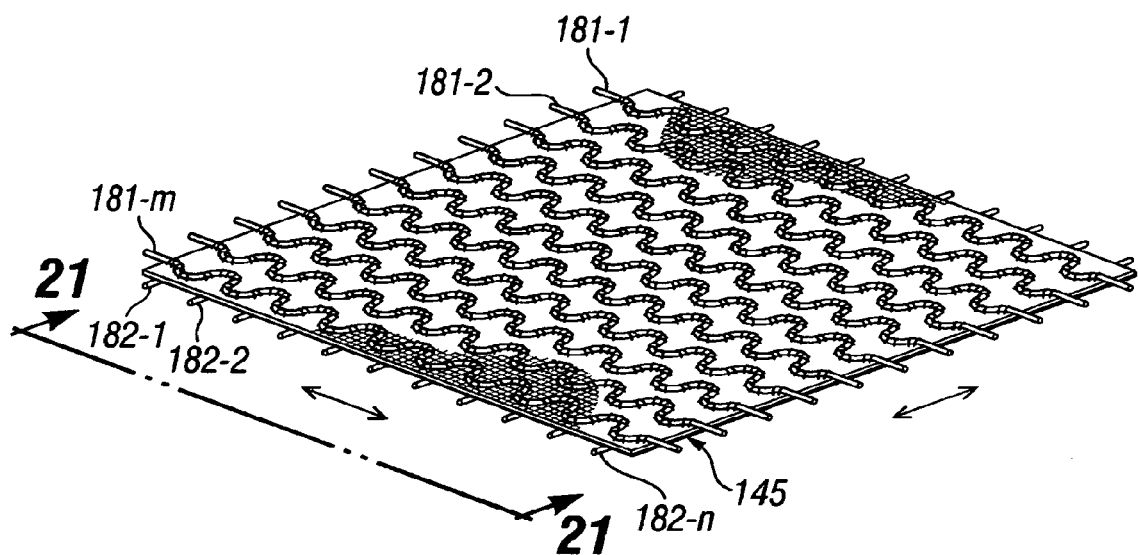
FIG. 18 is an upper perspective view of another modification of the single layer fabric substrate sensor array of FIG. 14 in which both the row and column conductive threads are sinuously arranged and located on opposite sides of a piezoresistive substrate sheet.
Figure 19:
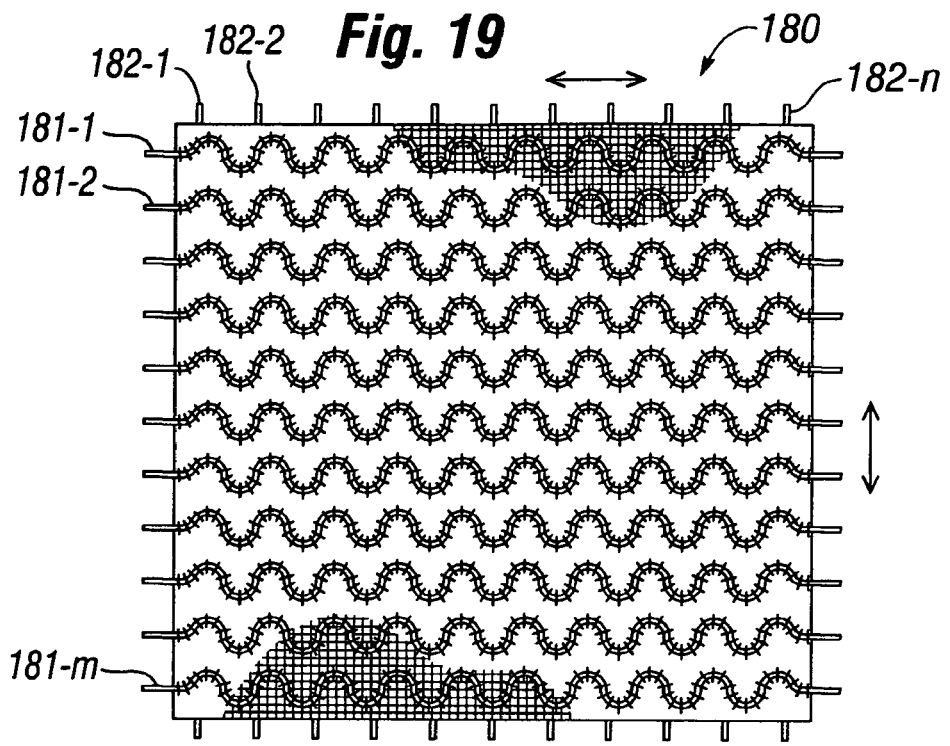
FIG. 19 is an upper plan view of the sensor array of FIG. 18.
Figure 20:
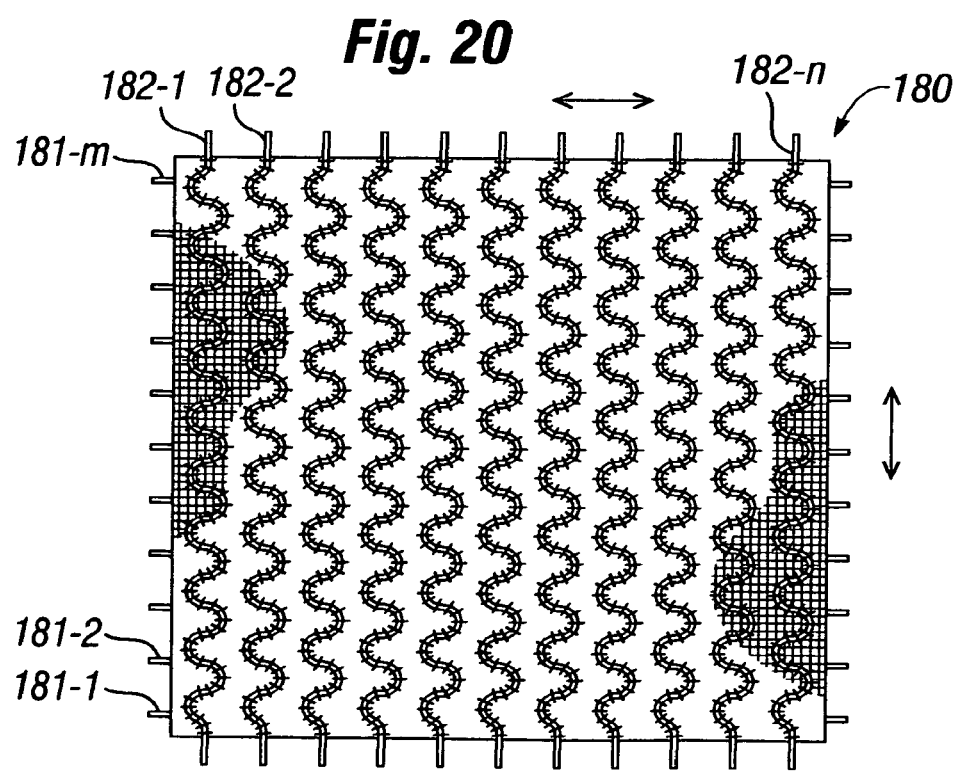
FIG. 20 is a lower plan view of the sensor array of FIG. 18.

FIG. 17 illustrates a modification of the force sensor arrays using fabric substrate sheets shown in FIG. 9, 13 or 14 and described above. As shown in FIG. 17, a lower fabric substrate sheet 145 of modified force sensor array 140 has attached thereto lower, column conductive piezoresistive threads 142 which are sinuously curved with respect to parallel straight base lines between opposite ends of each thread, rather than lying directly on the base lines, as are the column conductive threads 82 of sensor array 80 shown in FIG. 11. With this arrangement, lower fabric substrate sheet 145 is even more readily elastically stretchable in directions parallel to the column thread base lines because longitudinally spaced apart points on the fabric substrate sheet are not constrained to be at maximum lengths by the less elastically stretchable conductive threads. Thus, the stretchability of the column substrate sheet 145 is limited only by its intrinsic stretchability since the arrangement of column conductive threads 142 allows them to conform readily to size of the substrate sheet by changing spacing between peaks and valleys of the sinuously curved conductive threads, i.e., altering the spatial wavelengths of the sinuous curves formed by threads.

Optionally, upper row piezoresistive threads 141 may also be sinuously arranged in the same manner as lower column piezoresistive threads shown in FIG. 17, to thus enhance elastic compliance, or stretchability, of sensor array 140 is in directions parallel to the row conductive threads as well as in directions parallel to the column piezoresistive threads. Also, either or both row and column conductive threads of three-layer sensor arrays such as those of the type shown in FIG. 1 may be sinuously arranged to provide enhanced uniaxial or biaxial stretchability.

FIGS. 18-21 illustrate another modification 180 of the single fabric substrate sheet sensor array 120 of FIG. 14. Sensor array 180 has upper, row conductive threads 181 and lower, column conductive threads 182 which are both sinuously arranged on opposite sides of a fabric piezoresistive central substrate sheet 187. This construction gives array 180 greater elasticity in directions parallel to the column conductive threads 182 as well as in directions parallel to row conductive threads 181.

Figure 21:
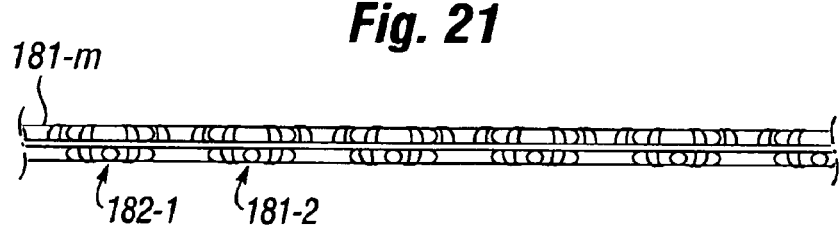
FIG. 21 is a vertical transverse sectional view of the sensor array of FIG. 19.
Figure 21A:
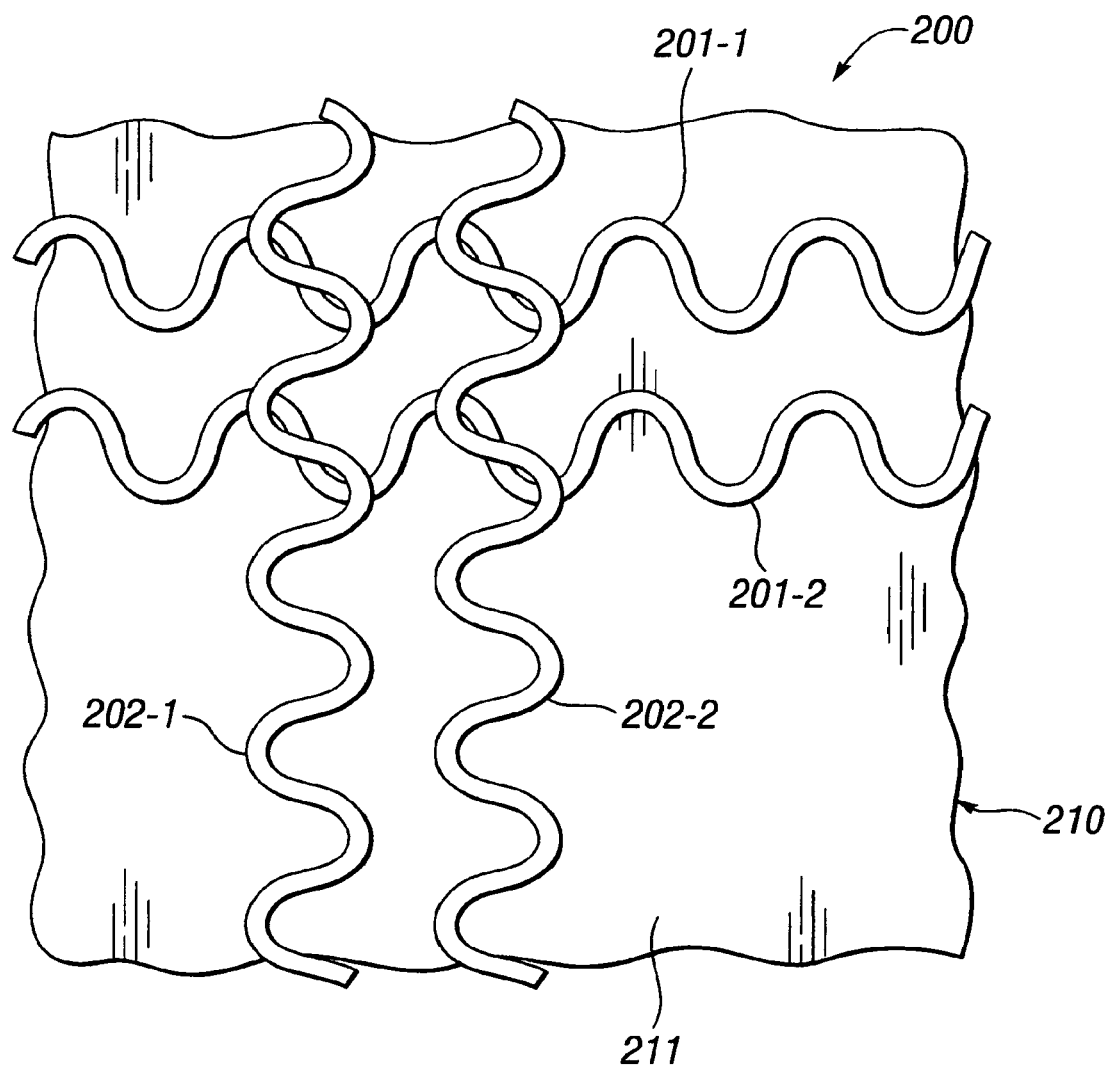
FIG. 21A is a fragmentary upper perspective view of a single layer fabric substrate sensor array in which both upper row and lower column piezoresistive threads are sinuously arranged and fastened to the same side of a single insulating substrate sheet.

FIG. 21A illustrates another modification 200, which row and column piezoresistive threads 201, 202 are both sinuously arranged and attached to the upper surface 211 of an insulating substrate sheet 210, in the manner shown in FIG. 16.

FIG. 22A illustrates the number of conductive leads required to measure the resistance of individual elements of a linear array of sensor elements, to thus determine numerical values of force or pressure exerted on each sensor element. As shown in FIG. 22A a single common lead-out conductor C is connected to a linear array of intersecting lead-out conductors $L_i$ through $L_n$ to form a plurality of sensor elements $S_I$ through $S_n$, by piezoresistive material at each intersection point. Thus, for a total of n sensors S, there are required a total R equal to n+1 lead-out conductors to measure the individual resistance of each sensor element $S_I$ through $S_n$ and hence determine the forces $F_1$ through $F_n$ exerted on each individual sensor element.

FIG. 22B shows a plurality of sensor elements $S_{n+1}$, $S_{n+2}$, $S_{n+3}$ which are not necessarily arranged in a linear array, being located, for example, on individual finger tips. As shown in FIG. 22B, n+1 lead-out conductors are also required for this configuration.

FIG. 7 illustrates the electrical resistance of a one-inch square piezoresistive force sensor element 48 using a piezoresistive sheet 37 having the formulation listed for an example sensor array 30 shown in FIGS. 1 and 2, and fabricated as described above, as a function of normal force or pressure exerted on the upper surface 47 of upper substrate sheet 33 of sensor array 30. As shown in FIG. 7, the resistance varies inversely as a function of normal force.

As shown in FIG. 1, row conductive threads 31-1 through 31-$m$, in vertical alignment with column conductive threads 32-1 through 32-$n$ form with piezoresistive layer sheet 37 between the column and row conductive threads a m×n rectangular matrix array of m×n force elements 48.

If upper and lower electrical connections to each sensor element 48 were electrically isolated from connections to each other sensor element, a separate pair of lead-out conductors for each of the sensors, would be required, i.e., a total of 2Q lead-out conductors for Q sensor elements or, if a single common electrode lead-out were employed as shown in FIG. 22, a total of Q+1 lead-outs would be required.

As shown in FIG. 1, sensor array 30 is arranged into a matrix of m rows and n columns, thus requiring only R=m×n lead-out conductors. However, as shown in FIG. 23, if matrix addressing of sensor array 30 is used to measure the resistance of individual sensors 48 to thereby determine normal forces exerted on the sensors, there is a substantial cross-talk between the resistance on an addressed sensor 48 and non-selected sensors because of parallel current paths to non-addressed sensors. To overcome this cross-talk problem, the present inventor has developed a method for modifying sensors 48 to give them a diode-like characteristic. As may be confirmed by referring to FIG. 24, the cross-talk between sensor elements 40 which have a non-bilateral, polarity-sensitive transfer function, mitigates the cross-talk problem present in the matrix of symmetrically conductive sensors 48 shown in FIG. 23.

Sensor elements 48 are modified to have a diode-like characteristic by modifying the preparation of piezoresistive layer sheet 37, as follows: First, a piezoresistive layer sheet 37 is prepared by the process described above. Then, either the upper surface 40 or the lower surface 41 of the piezoresistive coating 37A of piezoresistive sheet 37 is modified to form thereon a P-N, semiconductor-type junction.

Modification of piezoresistive coating 37A to form a P-N junction is performed by first preparing a slurry which has the composition of one of the three example mixtures described above, but modified by the addition of 5 ml each of copper oxide (CuO) in the form of a fine powder of 50-micron size particles, and 5 ml of cuprous oxide ($Cu_2O$) in the form of a fine powder of 50-micron size particles and thoroughly stir-mixing the foregoing ingredients. The resultant solution is then reduced using about 30 mg of solution of sodium borohydride, also known as sodium tetrahydroborate ($NaBH_4$) or ammonium phosphate, to form a solution having a pH of about 5.5. The solution is then coated onto the upper surface 40 or lower surface 41 of piezoresistive coating 37B on piezoresistive sheet 37. This coating process is performed using a roller coating process which results in about 0.5 ml of solution per square centimeters being applied. The surface coating is then allowed to air-dry at room temperature and a relative humidity of less than 20%, for 4 hours. After the coated surface has dried, it functions as a P-type semiconductor, while the uncoated side of coating 37B functions as an N-type semiconductor of P-N junction diode.

Figure 29:
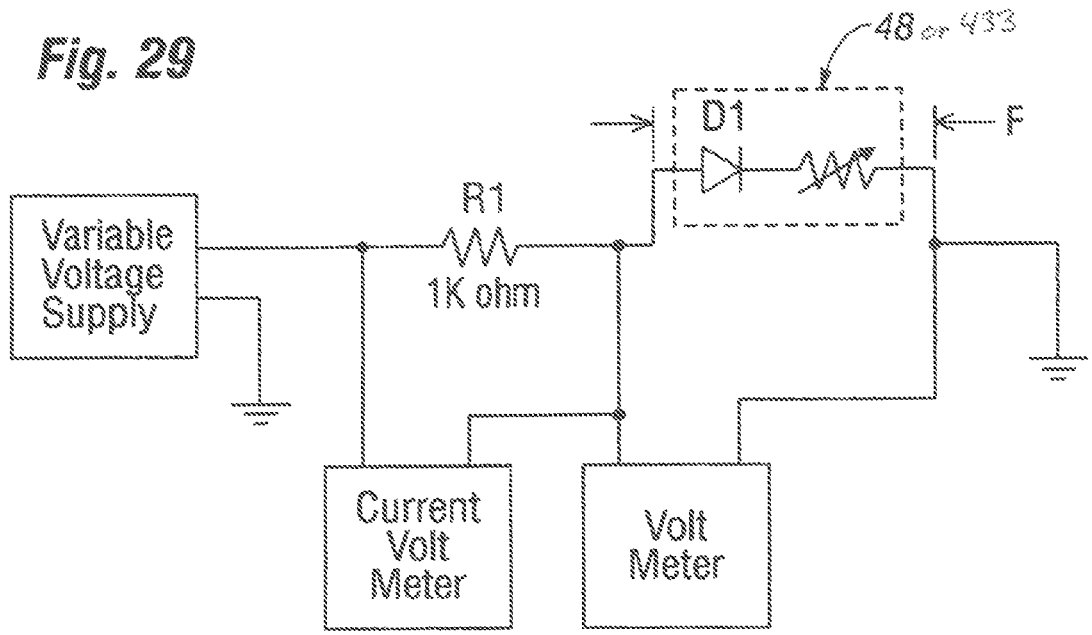
FIG. 29 is a partly schematic view of modifications of sensor elements of the arrays of FIG. 1 and FIG. 35, in which sensor elements of the array have been modified to provide them with P-N, diode-type junctions.
Figure 30:
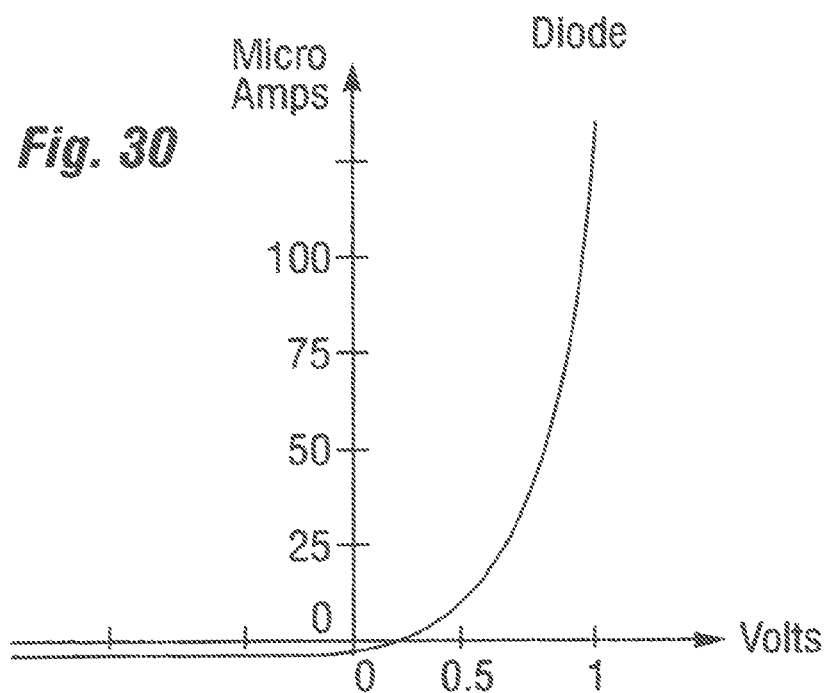
FIG. 30 is a current-versus-voltage diagram for the sensor elements of FIG. 27A.
Figure 31:
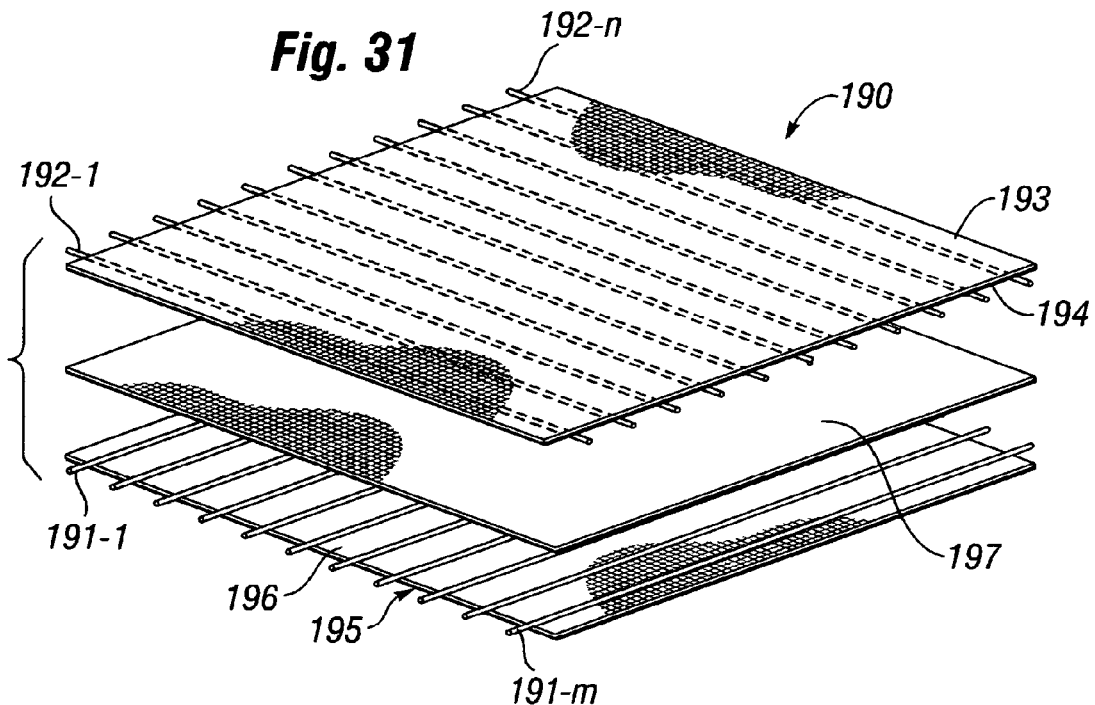
FIG. 31 is an exploded perspective view of another embodiment of a force sensor array.
Figure 32:
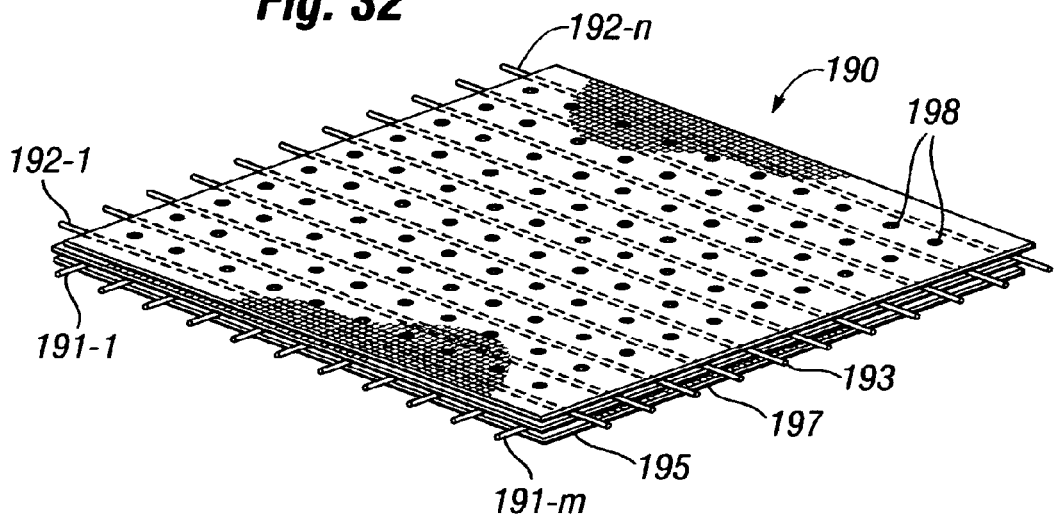
FIG. 32 is a perspective view of the sensor array of FIG. 31.

FIG. 29 illustrates a sensor element 48 which has been prepared as described above to give the sensor a diode-like characteristic, and a circuit for obtaining the I-V (current versus voltage) transfer function of the sensor. FIG. 30 shows a typical I-V curve for sensor elements 48 of FIG. 29.

As stated above, the advantage of modifying sensor elements 48 of sensor array 30 by adding a semi-conductive layer that acts like a diode is that it reduces cross talk between sensors. As is shown in FIG. 23, this cross-talk occurs because of the so-called "completing the square" phenomenon, in which three connections are made in a square matrix array of three non-addressed resistors that form the three corners of a square. Thus, any two connections in a vertical column and a third one in the same row function as either connection in an X-Y array of conductors. The resistor at the fourth corner of the square shows up as a phantom in parallel with an addressed resistor because the current can travel backwards through that resistor, and forward through the other resistors. Care and additional expense must be taken in the electronics to eliminate the contribution of this phantom. For example, if, as is shown in FIG. 23, a potential V is applied between row and column conductors $X_1Y_1$, to thereby determine the resistance of piezoresistive sensor resistance $R_{11}$, reverse current flow through "phantom" resistor $R_{22}$ would cause the sum of resistances $R_{12}+R_{22}+R_{22}$ to shunt $R_{11}$, resulting in the parallel current flow paths indicated by arrows in FIG. 23, which in turn would result in the following incorrect value of resistance:

$R_{x1}y_1=R_{11}//(R_{12}+[R_{22}]+R_{21})$, $R_{x1}Y_1=R_{11}(R_{12}+[R_{22}]+R_{21})/(R_{11}+R_{12}+[R_{22}]+R_{21})$, where brackets around a resistance value indicate current flow in a counterclockwise direction through that resistor, rather than clockwise, i.e., diagonally downwards towards the left. Thus, for example, if each of the four resistances listed above had a value of 10 ohms, the measured value of $R_{11}$ would be:

$R_{11}=10(10+10+10)/(10+10+10+10)=300/40=7.5$ ohms, i.e., 25% below the actual value, 10 ohms, of $R_{11}$. If the resistance values of $R_{12}$, $R_{22}$ and $R_{21}$ of the three non-addressed piezoresistive sensor element 48 were each lower, e.g., 1 ohm, because of greater forces concentrated on those sensor elements 48, the measured value of $R_{11}$ would be:

$R_{11}=10(1+1+1)/(10+1+1+1)=30/13=2.31$ ohms, i.e., a value of about 77 percent below the actual value of $R_{11}$.

On the other hand, by placing a diode in series with each piezoresistive sensor element 48, as shown in FIG. 24, the electrical resistance of an element measured in a reverse, counterclockwise direction a test current flow through the sensor element, e.g., $R_{22}$, would be for practical purposes arbitrarily large, or infinity compared to the clockwise forward paths of current through the other resistances shown in FIGS. 23 and 24. In this case, the measured resistance value for a 2×2 matrix of four resistances each having a value of 10 ohms would be:

$R_{X1}Y_1=10(1+\infty+1)/(10+1+\infty+1)=10$ ohms, the correct value. Thus, modifying each sensor element 48 to include a p-n junction thereby give the sensor element a diode-like characteristic electrically isolates, i.e., prevents backward current flow, through each sensor element 48. This enables the correct value of electrical resistance of each sensor element 48 and hence forces exerted thereon to be measured accurately $R_{x1}y_1$ using row and column matrix addressing rather than requiring a separate pair of conductors for each sensor element.

FIG. 25 illustrates a force measuring apparatus 150. The apparatus 150 may use any of the types of sensor arrays described above, but in a particular example shown in FIG. 25 uses a sensor array 70 of the type shown in FIG. 5.

As shown in FIG. 25, force measuring apparatus 150 used four sensor arrays 70-1, 70-2, 70-3 and 70-4, each having a matrix of 16 row conductive threads by 16 column conductive threads. The four arrays are arranged in a square matrix, to thus form a composite sensor array 70-C consisting of 32 rows×32 columns of conductive threads having formed at their intersection 32×32=1,024 sensor elements 88. As shown in FIG. 25, each of the 32 row conductive thread lead-out wires and each of the 32 column conductive thread lead-outs is connected to a separate electrically conductive connector pin of a plurality of connector pins 154-1 through 154-64 of a pair of electrical interface connectors 153-1, 153-2.

FIG. 26 illustrates a force measurement system 160 which utilizes the force sensor apparatus 150 described above.

As shown in FIG. 26, force measurement system 160 includes a computer 161 which is bidirectionally coupled to force sensor array 70 of force sensor apparatus 160 through a force sensor interface module 162. The sensor interface module 162 includes a Digital-to analog Converter (DAC) 163 for generating in response to control signals from computer 161 test voltages or currents which are directed to matrix-addressed individual force sensors 88.

As shown in FIG. 26, individual force sensor elements 88 are addressed by connecting one terminal of a current or voltage source controlled by DAC 163 to a selected one of X-row conductors 51-1-51-$m$ by an X multiplexer 164, and connecting the other terminal of the source to a selected one of Y-column conductors 52-1-52-$m$ by a Y multiplexer 165. Sensor interface module 162 also included an Analog-to-Digital Converter (ADC) 166 which measures the voltage drop or current through a sensor element 88 resulting from application of a test current or voltage, and inputs the measured value to computer 161. Using predetermined scale factors, computer 161 calculates the instantaneous value of electrical resistance of a selected addressed sensor element 88, and from that resistance value, a corresponding normal force instantaneously exerted on the addressed sensor.

In response to control signals cyclically issued by computer 161, X multiplexer 164 and Y multiplexer 165 are used to cyclically measure the resistance of each force sensor element 88, at a relatively rapid rate of, for example, 3,000 samples per second, enabling computer 161 to calculate the force exerted on each force sensor element 88 at that sampling rate.

Measurement system 160 includes an operator interface block 167 which enables values of force or pressures measured by sensor elements 88 to be displayed as numerical values and/or a graph or pressure/force map on the display screen of a computer monitor 168, or outputted to a peripheral device such as a printer, or a network such as the internet, through an I/O block 169.

Figure 27A:
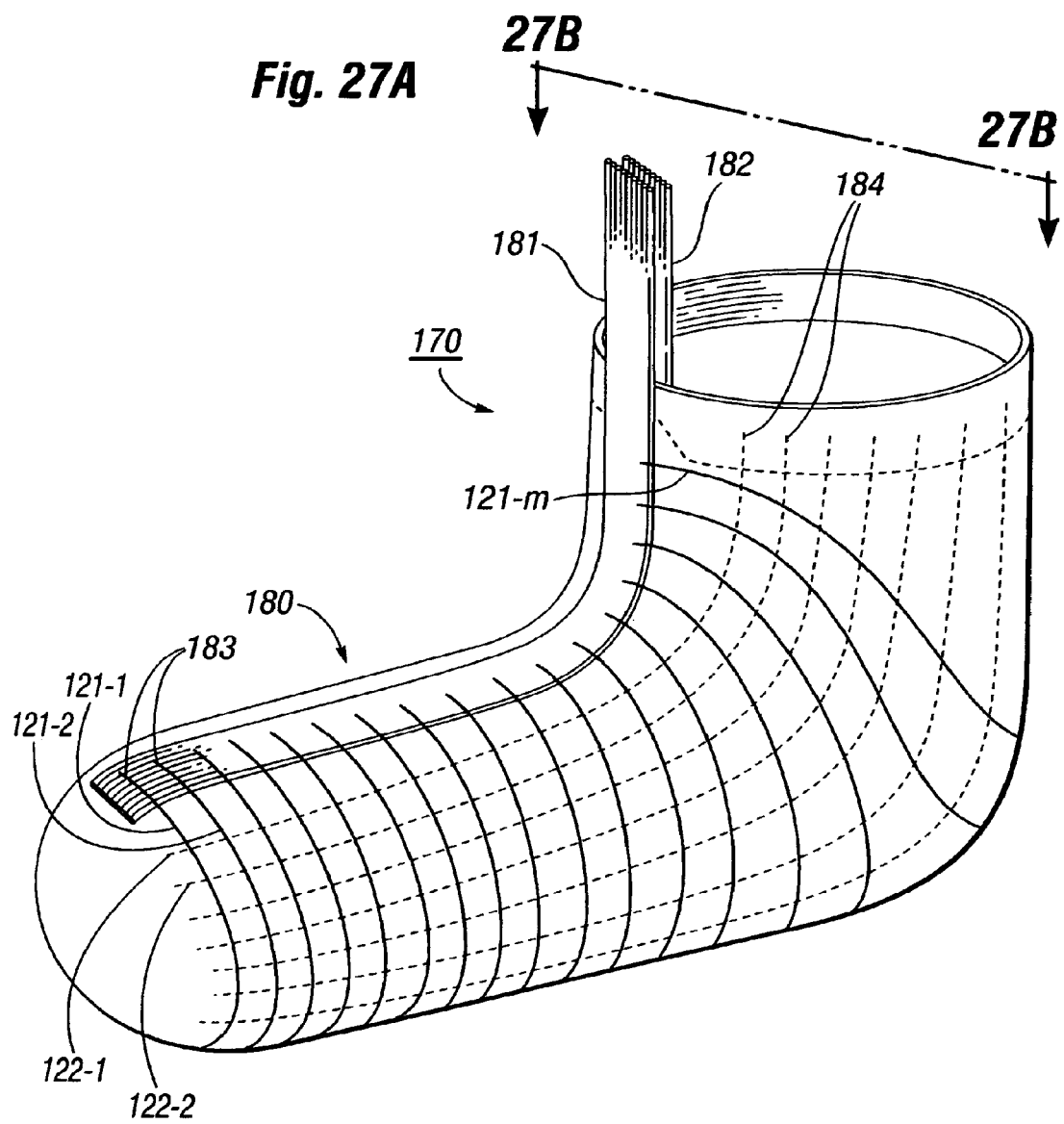
FIG. 27A is a perspective view of a sock incorporating the sensory array of FIG. 14-16 or 17-20.

FIGS. 27A and 27B illustrate a sock 170 which includes one of the novel sensor arrays employing conductive threads which were described above, such as the single layer, fabric substrate piezoresistive thread sensor array shown in FIG. 14-16 or 17-20.

As shown in FIG. 17, sock 170 which includes a single layer fabric force sensor array 180 that is a modification of the planar force sensor array 120 shown in FIGS. 14-16 and described above. The modification of force sensor array 120 to form force sensor array 180 may be best visualized by considering that the left and right side edges of the array 120 are brought upwards from the plane of the page to meet and form a hollow cylindrical tube.

Row conductor threads protruding 121 from the aligned edges of the array are then electrically conductively fastened to a first, row conductor ribbon cable 181. Column conductive threads protruding from one edge of the rolled-up array are electrically conductively fastened to a second, column conductor ribbon cable 182. Outer ends 183, 184 who protrude from an edge of array 120 are electrically connected to a resistance measuring circuit as shown in FIG. 26 and described above.

FIGS. 31-34 illustrate modifications of fabric substrate force sensor arrays using conductive threads, in which the conductive threads are fixed to a fabric substrate sheet without the use of sewn stitching by adhesive applied directly to a conductive thread. Thus, a first, three-layer fabric sensor array 190 includes a plurality of parallel, spaced apart row conductive elastic threads 191 which are adhesively bonded to the lower surface 194 of an upper stretchable fabric substrate sheet 193 made of 3 mil thick polyester or either of the two Milliken fabrics described above. Sensor array 190 also includes a plurality of parallel spaced apart column conductive elastic threads 192 which are adhesively bonded to an upper surface 196 of a lower stretchable fabric substrate sheet 195. A thin sheet of stretchable fabric prepared to give it a piezoresistive property in the manner described above comprises a central piezoresistive layer 197 which is positioned between row and column conductive threads 191, 192. The foregoing three layers are then stacked on top of one another and dots of glue injected through the mesh openings of the fabric substrate of all three layers to adhere them together and thus form a completed sensor array 190.

Sensor array 200, shown in FIG. 33, utilizes a single substrate sheet 207. Conductive row and column threads 191, 192, separated by insulating threads 210, 211, are adhered to upper surface 212 and lower surface 213 of sheet 207 by double-stick tape strips 213, 214.

FIGS. 35-43 illustrate various aspects of a method and apparatus for minimizing body force concentrations on a human body using an adaptive cushion. The example embodiment depicted in FIGS. 35 and 37 includes an adaptive cushion which is of an appropriate size and shape for use on a standard single or hospital bed. However, as will be clear from the ensuing description of that example embodiment, the size and shape of the adaptive cushion can be varied to suit different applications, such as for use on a fixed chair or wheel chair.

Referring first to FIGS. 35 and 36A, an adaptive cushion apparatus 420 for minimum body force concentrations on a body of a person lying on a bed may be seen to include a longitudinally elongated, rectangular cushion overlay 421. Cushion 421 has an appropriate size and shape to fit conformally on top of a standard size hospital bed. Thus, an example embodiment of cushion 421 had a laterally elongated, rectangular shape with a length of about 6 feet, a width of about 3 feet, and a thickness of about 4 inches.

The six panels of each air bladder cell 423 are sealingly joined at edges thereof to form a hermetically sealed body which has a hollow interior space 422A.

As shown in FIG. 36A, mattress overlay cushion 421 is constructed as a rectangular, two-column by six-row array of 12 individual inflatable air bladder cells 422. Each air bladder cell 422 has a laterally elongated, rectangular shape, having a length of about 18 inches, a depth of about 17 inches, and a thickness of about 4 inches. As shown in FIGS. 35 and 36, bladders 422 are arranged in left and right columns, each having 6 longitudinally spaced apart, laterally disposed, laterally elongated bladders. As shown in FIGS. 36 and 38, each air bladder cell has a flat base panel 423, left and right end panels 424, 425, head and toe or front and rear panels 426, 427, and an upper panel 428. The bladders 422 are made of a thin sheet of a flexible, elastomeric material such as neoprene rubber or polyurethane, having a thickness of about 0.014 inch. The six panels of each air bladder cell 422 are sealingly joined at edges thereof to form a hermetically sealed body which has a hollow interior space 422A. Optionally, each air bladder cell 422 may be fabricated from a tubular preform in which each end panel is sealingly joined to opposite transverse ends of the tubular preform. In either embodiment, adjacent panels of an individual air bladder cell are sealingly joined by a suitable method such as ultrasonic bonding, RF-welding or adhesive bonding.

The number, size, shape, relative positioning and spacing of air bladder cells 422 of mattress cushion overlay 421 are not believed to be critical. However, it is believed preferable to arrange mattress overlay 421 into symmetrically-shaped left and right columns each having at least five and preferably six longitudinal zones corresponding to major curvature of a longitudinally disposed medial section of a typical human body. Thus, as shown in FIGS. 35, 36A and 37, mattress overlay cushion 421 has a left-hand column of six air bladder cells 422L1-422L6, and a right-hand column of six cells 421R1-421R6.

Figure 40:
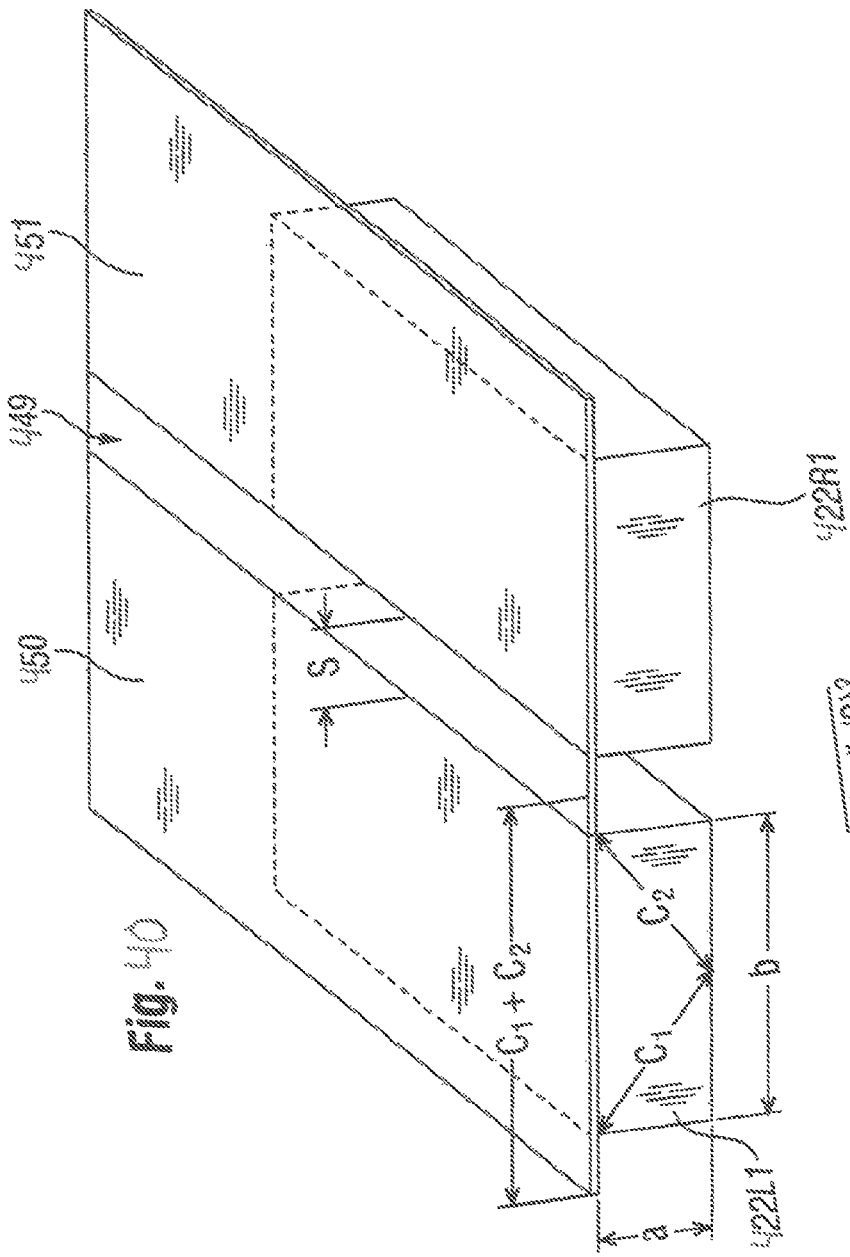
FIG. 40 is a diagrammatic view showing an exemplary relationship between the dimensions of adjacent air bladder cells and the width of an insulating strip between conductors of sensors on the cells.

As shown in FIGS. 38 and 40, the bladders are stacked closely together in both front and rear and side by side directions, with minimum longitudinal and lateral spacings 429, 430, respectively, that are vanishingly small so that adjacent bladder cells physically contact each other.

As indicated in FIGS. 35 and 36, each bladder cell 422 is provided with a tubular air inlet port 431 which protrudes through a side wall, e.g., a left or right side wall 424 or 425, and communicates with a hollow interior space 422A within the bladder. Air admitted into or exhausted from hollow interior space 422A through port 431 of an air bladder cell 422 enables the cell to be inflated or deflated to a selected pressure.

Although the shape of each air bladder cell 422 of cushion 421 shown in FIGS. 35 and 36 is that of a rectangular block, or parallelepiped, the air bladder cells may optionally have different shapes, such as convex hemispheres protruding upwards from the base of the cushion. Also, the array of air bladder cells 422 of cushion 421 may be parts of a unitary structure with a common base panel 423 which has individual rectangular-block shaped, hemispherical or hollow inflatable bodies of other shapes protruding upwardly from the common unitary base panel.

Whether individual air bladder cells 422 are separate bodies or upper inflatable shell-like portions protruding upwardly from a common base, air inlet/exhaust port tubes 431 of each air bladder cell 422, or selected air bladder cells 422, may be located in the base panel 423 of the cell and protrude downwardly from the cell, rather than being located in a side wall and protruding laterally outwards, as shown in FIGS. 35 and 36A.

Figure 39:
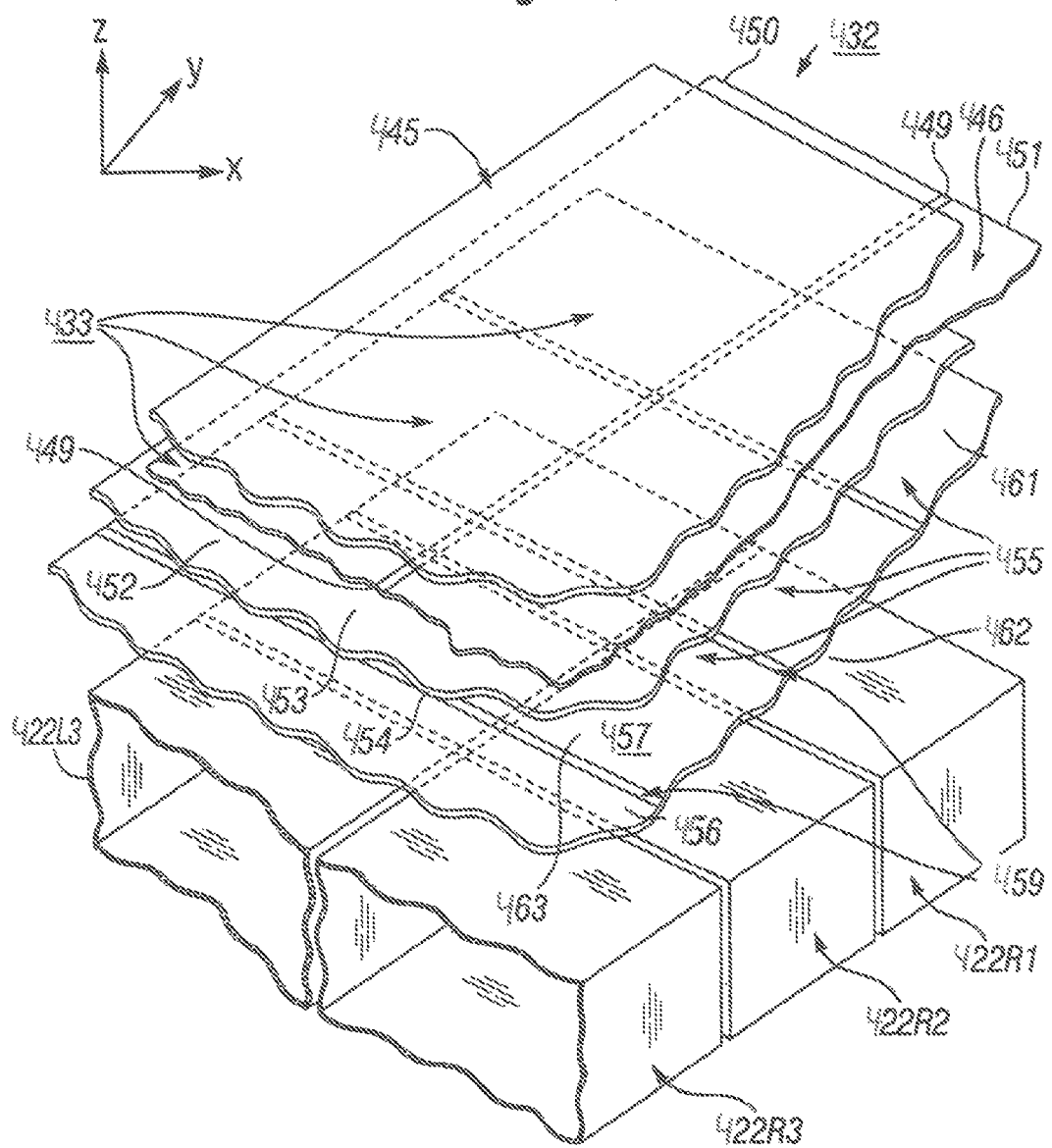
FIG. 39 is a fragmentary exploded perspective view of the mattress of FIG. 35, showing elements of a force sensor arrangement thereof.

As shown in FIGS. 35, 36 and 39, body force minimization apparatus 420 includes a force sensor array 432 which has a matrix of individual force sensors 433, with at least one sensor positioned on the upper surface 428 of each air bladder cell 422. As will be explained in detail below, each force sensor 433 comprises a force sensitive transducer which has an electrical resistance that varies inversely with the magnitude of a normal, i.e., perpendicular force exerted on the sensor by an object such as the body of a person supported by overlay cushion 421. In one embodiment, force sensor array 432 is maintained in position on the upper surfaces of air bladder cells 422 by a water-proof, form-fitting contour fabric sheet 421A which fits tightly and removably over cushion 421, as shown in FIG. 37.

Referring to FIG. 35, it may be seen that body force minimization apparatus 420 includes an electronic control module 435. As will be explained in detail below, electronic control module 435 includes sensor interface circuitry 436 for electrical interconnection to sensors 433. Electronic control module 435 also includes a computer 437 which is interconnected with sensor interface circuitry 436. Computer 437 is programmed to receive input signals from sensor interface circuitry 436, measure the resistance of individual sensors 433 and calculate therefrom the magnitude of forces exerted on each sensor, make calculations based on the force measurements, and issue command signals to control the pressure in individual air bladder cells 422 which are calculated using an algorithm to minimize force concentrations on the cells.

In one embodiment of apparatus 420, measurement of the resistance of each sensor 433 is facilitated by arranging the sensors into a matrix array of rows and columns. With this arrangement, individual resistances of a 6×2 array 432 of sensors 433 may be measured using 6 row interface conductors and 2 column interface conductors 450, 451, as shown in FIG. 35.

To avoid cross talk between measurements of individual sensors 433, the aforementioned row-column addressing arrangement requires that each sensor have a non-bilateral, asymmetric current versus voltage characteristics, e.g., a diode-like impedance characteristic. As will be described in detail below, the present invention includes a novel sensor having the required diode-like characteristic. Alternatively, using force sensors 433 which do not have a diode-like characteristic, the force sensor array 432 can be partitioned into 12 separate rectangular sensors 433 each electrically isolated from one another, with a separate pair of interface conductors connected to upper and lower electrodes of each sensor.

As shown in FIG. 35, body force minimization apparatus 420 includes an air pump or compressor 440 for providing pressurized air to the input port 442 of a selector valve manifold 441. Selector valve manifold 441 has 12 outlet ports 443A, each connected through a valve 443 to a separate air bladder cell inlet port 431. As will be explained in detail below, the compressor 440, selector valve manifold 441 and valves 443 are operably interconnected to computer 437 and an air pressure measurement transducer 444. Pressure transducer 444 outputs an electrical signal proportional to pressure, which is input to computer 437. This arrangement enables the inflation pressure of each air bladder cell 422 to be individually measured and varied under control of the computer 437.

FIGS. 36A, 38 and 39 illustrate details of the construction of force sensor array 432. As shown in those figures, sensor array 432 includes an upper cover sheet 445 made of a thin flexible, elastically stretchable material. In an example embodiment of sensor array 432 fabricated by the present inventor, cover sheet 445 was made of "two-way stretch" Lycra-like material which had a thickness of about 0.010 inch and a thread count of about 88 threads per inch. That material had the trade name Millglass Platinum, Style No. (24)7579, obtained from the Milliken & Company, P.O. Box 1926, Spartanburg, S.C. 29304.

Referring to FIG. 39, sensor array 432 includes an upper, column conductor sheet 446 which is fixed to the lower surface of upper flexible cover sheet 445, by flexible adhesive strips made of 3M transfer tape 950, or a flexible adhesive such as Lepage's latex contact adhesive. Column conductor sheet 446 is made of a woven fabric matrix sheet composed of 92% nylon and 8% Dorlastan fibers, which give the sheet a flexible, two-way stretch elasticity. The fabric matrix sheet of conductor sheet 446 is electroless plated with a base coating of copper, followed by an outer coating of nickel. The metallic coatings completely impregnate the surfaces of fibers adjacent to interstices of the mesh fabric, as well as the upper and lower surfaces 447, 448 of the conductor sheet 446, thus forming electrically conductive paths between the upper and lower surfaces 447 and 448. The present inventor has found that a suitable conductive fabric for conductor sheet is a Woven Silver brand, Catalog #A251 available from Lessemb Company, 809 Madison Avenue, Albany, N.Y. 12208, USA.

In an example embodiment of sensor array 432, upper conductive sheet 446 was fabricated from the Woven Silver, Catalog #A151 material described above. The surface resistivity of upper and lower surfaces 447, 448 of that material was about 1 ohm per square or less, and the inter-layer resistance between upper and lower surfaces 447, 448 was about 50 ohms per square.

In one embodiment of sensor array 432, individual conductive pads, or rows or columns of conductors, are formed by etching metal-free channels vertically through conductor sheet 446, from the top of upper conductive surface 447, all the way to the bottom of lower conductive surface 448. Thus, as shown in FIG. 39, narrow longitudinally disposed straight channels 449 are etched through upper column conductor sheet 446. This construction results in the formation of two adjacent, relatively wide, longitudinally elongated left and right planar column electrodes 450, 451. The adjacent left and right column electrodes are separated by a relatively thin channel 449, thus electrically isolating the adjacent column electrodes from each other.

Insulating channels 449 are etched through upper conductor sheet 446 to form column electrodes 450 and 451 by the following novel process.

First, to prevent capillary wicking and resultant wetting of a subsequently applied etchant solution to fabric conductor sheet 446, the sheet is pre-processed by treating it with a hydrophobic substance such as PTFE. The treatment can be made by spraying the conductor fabric sheet 446 with an aerosol containing a hydrophobic material such as PTFE. A suitable aerosol spray is marketed under the trade name Scotch Guard by the 3M Company, St. Paul, Minn. Areas of fabric conductor sheet 446 which are to have insulating channels 449 formed therein are masked from the hydrophobic treatment by adhering strips of masking tape which have the shape of the channels to the sheet before applying the hydrophobic material to the sheet.

Following the pre-processing of conductor sheet 446 to make it hydrophobic, sheets of masking tape are adhered tightly to both upper and lower surfaces 447, 448 of the conductor sheet, using a roller or press to insure that there are no voids between the masking tape and surfaces, which could allow etchant solution to contact the conductive surfaces. Next, strips of masking tape having the shape of insulating channels 449 are removed from the conductor sheet. Optionally, the strips of masking tape to be removed are preformed by die-cutting partially through larger sheets of masking tape.

After strips of masking tape corresponding to channels 449 have been stripped from conductor sheet 446, the conductive metal coatings of the fabric sheet aligned with the channels is chemically etched away. One method of performing the chemical etching uses a concentrated solution of 10 mg ammonium phosphate in 30 ml of water. The ammonium phosphate solution is mixed with methyl cellulose solid powder, at a concentration of 10 percent methyl cellulose powder until a gel consistency is obtained. The etchant gel thus formed is then rollered onto the areas of upper and lower surfaces 447, 448 of conductor sheet 446, over channels 449. The etchant gel is allowed to reside on channels 449 for approximately 1 hour, at room temperature, during which time the nickel and copper plating of the fabric matrix of conductor sheet 446, in vertical alignment with channels 449, is completely removed, thus making the channels electrically insulating. This process separates the conductor sheet into left and right column electrodes 450, 451, respectively.

The etching process which forms insulating channel 449 is completed by rinsing the etchant gel from upper and lower surfaces 447, 448 of conductor sheet 446, followed by removal of the masking tape from the upper and lower surfaces.

Referring still to FIG. 39, it may be seen that sensor array 432 includes a thin piezoresistive sheet 452 which has on an upper surface 453, that is in intimate contact with lower surfaces of left and right column electrodes 450, 451. Piezoresistive sheet 452 also has a lower surface 454 which is in intimate electrical contact with the upper surfaces of row electrodes on a lower row conductor sheet 456. Lower, row conductor sheet 456 has a construction exactly similar to that of upper, column conductor sheet 446. Thus, lower row conductor sheet 456 has upper and lower conductive surfaces 457, 458, and narrow, laterally disposed insulating channels 459 which are positioned between and define row electrodes 461, 462, 463, 464, 465, 466.

The function of piezoresistive sheet 452 of sensor array 432 is to form a conductive path between column and row electrodes, e.g., left-hand column electrode 450 and rear row electrode 461, the resistance of which path varies in a predetermined fashion as a function of normal force exerted on the sensor array.

In example embodiments of sensor array 432, piezoresistive sheet 452 was fabricated by coating a stretchy, thin Lycra-like fabric sheet with a piezoresistive material. A suitable fabric sheet, which forms a matrix for supporting the piezoresistive material, was a fabric known by the trade name Platinum, Milliken, Style #247579, obtained from the manufacturer, Milliken & Company, Spartanburg, S.C., USA. That fabric had a fiber content of 69 percent nylon and 31 percent Spandex, a thread count of about 88 threads per inch, and a thickness of 0.010 inch. The piezoresistive material used to coat the fabric matrix is made as follows:

A solution of graphite, carbon powder, nickel powder and acrylic binder are mixed in proportions as required to obtain the desired resistance and piezoresistive properties. Silver coated nickel flake is used to achieve force response in the low force range of 0 to 1 psi, graphite is used for the mid range of 1 to 5 psi and Charcoal Lamp Black is used for high force range of 5 to 1000 psi. Following is a description of the substances which are constituents of the piezoresistive material:

Silver Coated Nickel Flake:
  Platelets approximately one micron thick and 5 microns in diameter.
  Screen Analysis (−325 Mesh) 95%.
  Apparent Density 2.8.
  Microtrac d50/microns 12-17.
  Available from: Novamet Specialty Products Corporation, 681 Lawlins Road, Wyckoff, N.J. 07481
Graphite Powder:
  Synthetic graphite, AC-4722T
  Available from: Anachemia Science
  4-214 DeBaets Street
  Winnipeg, MB R2J 3W6
Charcoal Lamp Black Powder:
  Anachemia Part number AC-2155
  Available from: Anachemia Science
  4-214 DeBaets Street
  Winnipeg, MB R2J 3W6
Acrylic Binder:
  Staticide Acrylic High Performance Floor Finish
  P/N 4000-1 Ph 8.4 to 9.0
  Available from: Static Specialties Co. ltd.
  1371-4 Church Street
  Bohemia, N.Y. 11716

Following are examples of mixtures used to make piezoresistive materials having different sensitivities:

Example I for forces in the range of 0 to 30 psi:
  200 ml of acrylic binder
  10 ml of nickel flake powder
  10 ml of graphite powder
  20 ml of carbon black
Example II for forces in the range of 0-100 psi
  200 ml of acrylic binder
  5 ml of nickel flake powder
  5 ml of graphite powder
  30 ml of carbon black
Example III for forces in the range of 0-1000 psi
  200 ml of acrylic binder
  1 ml of nickel flake powder
  1 ml of graphite powder
  40 ml of carbon black The fabric matrix for piezoresistive sheet 452 is submerged in the piezoresistive coating mixture. Excess material is rolled off and the sheet is hung and allowed to air dry.

FIG. 40 illustrates calculation of a minimum spacing S between adjacent air bladder cells 422, and a minimum width of non-conductive strip 449 between adjacent conductors of sensor array 432.

Referring to FIG. 40, as a patient sinks into a deflating bladder 422, the upper force sensor layer 433 is drawn down and away from the bladder over which it was initially positioned. If the non-conductive strip 449 is too narrow, there is a possibility that a conductor such as column conductor 450 overlying the deflating bladder will contact adjacent conductor 451 and, thus register forces that are not representative of the force over the bladder in which it was originally positioned. It is therefore necessary to make the non-conductive strip 449 wide enough to prevent this from happening. If we assume a simple situation wherein an air bladder cell is deflated until the center of the cell, then the force sensing layer is drawn down a distance equal to the diagonals (C1 and C2) as shown in FIG. 40, the width S of non-conductive strip 449 should be made equal to or greater than (C1+C2−the width of the bladder) to prevent forces being misread as coming from a neighboring cell.

Figure 28:
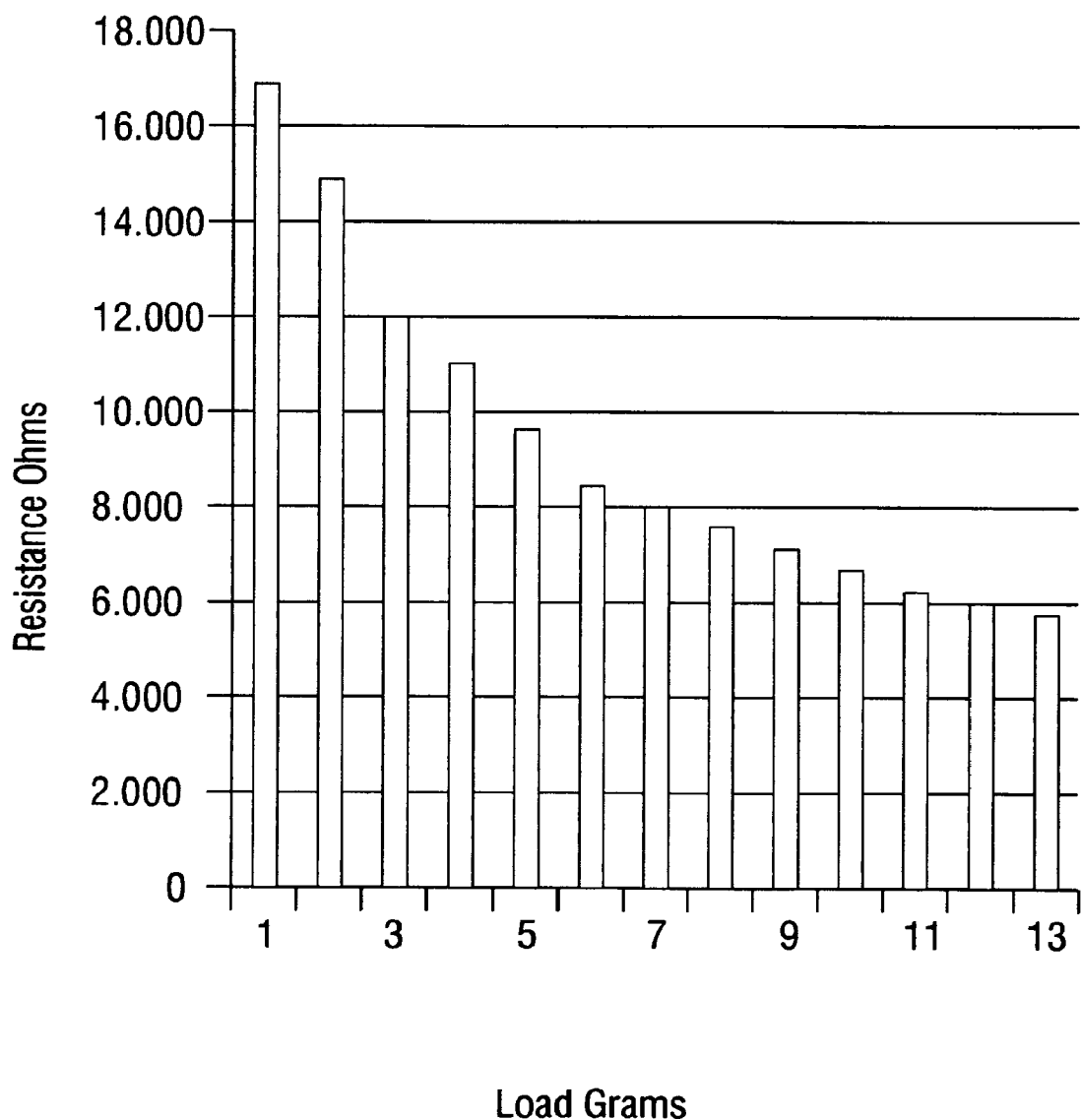
FIG. 28 is a typical electrical resistance-versus-normal force diagram of the sensors disclosed herein.

FIG. 28 illustrates the electrical resistance of a one-inch square piezoresistive force sensor element 448 using a piezoresistive sheet 437 having the formulation listed for an example sensor array 432 shown in FIGS. 35 and 36, and fabricated as described above, as a function of normal force or pressure exerted on the upper surface 447 of upper substrate sheet 433 of sensor array 432. As shown in FIG. 28, the resistance varies inversely as a function of normal force.

As shown in FIGS. 35 and 39, left and right column electrodes 450 and 451, in vertical alignment with row electrodes 461, 462, 463, 464, 465, 466, of 12 form with piezoresistive layer sheet 452 between the column and row electrodes a 2×6 rectangular matrix array of 12 force sensors 433.

Optionally, the upper and lower electrodes for each sensor 433 could be segmented into electrically isolated rectangular pads by etching channels 449, 459 through both upper conductive sheet 446 and lower conductive sheet 456. This arrangement would require a separate pair of lead-out conductors for each of the 12 sensors, i.e., a total of 24 leads.

As shown in FIGS. 35 and 39, sensor array is arranged into rows and columns, thus requiring only 8 lead-out conductors. However, as shown in FIG. 23, if matrix addressing of sensor array 432 is used to measure the resistance of individual sensors 433 to thereby determine normal forces exerted on the sensors, there is a substantial cross-talk between the resistance on an addressed sensor 433 and nonselected sensors because of parallel current paths to non-addressed sensors. To overcome this cross-talk problem, the present inventor has developed a method for modifying sensors 433 to give them a diode-like characteristic. As may be confirmed by referring to FIG. 24, the cross-talk between sensors 433 which have a non-bilateral, polarity-sensitive transfer function, mitigates the cross-talk problem present in the matrix of symmetrically conductive sensors 433 shown in FIG. 23.

Sensors 433 are modified to have a diode-like characteristic by modifying the preparation of piezoresistive layer sheet 452, as follows: First, a piezoresistive layer sheet 452 is prepared by the process described above. Then, either the upper surface 469 or the lower surface 470 of the piezoresistive coating 467 of piezoresistive sheet 452 is modified to form thereon a P-N, semiconductor-type junction.

Modification of piezoresistive coating 467 to form a P-N junction is performed by first preparing a slurry which has the composition of one of the three example mixtures described above, but modified by the addition of 5 ml each of copper oxide (CuO) in the form of a fine powder of 50-micron size particles, and 5 ml of cuprous oxide ($Cu_2O$) in the form of a fine powder of 50-micron size particles and thoroughly stir-mixing the foregoing ingredients. The resultant solution is then reduced using about 30 mg of solution of sodium borohydride, also known as sodium tetrahydroborate (NaBH4) or ammonium phosphate, to form a solution having a pH of about 5.5. The solution is then coated onto the upper surface 469 or lower surface 470 of piezoresistive coating 468 on piezoresistive sheet 452. This coating process is performed using a roller coating process which results in about 0.5 ml of solution per square centimeters being applied. The surface coating is then allowed to air-dry at room temperature and a relative humidity of less than 20%, for 4 hours. After the coated surface has dried, it functions as a P-type semiconductor, while the uncoated side of coating 468 functions as an N-type semiconductor of P-N junction diode.

FIG. 29 illustrates a sensor 433 which has been prepared as described above to give the sensor a diode-like characteristic, and a circuit for obtaining the 1-V (current versus voltage) transfer function of the sensor. FIG. 30 shows a typical 1-V curve for sensor 433 of FIG. 29.

As stated above, the advantage of modifying sensors 433 by adding a semi-conductive layer that acts like a diode is that it reduces cross talk between sensors. As is shown in FIG. 23, this cross-talk occurs because of the so-called "completing the square" phenomenon, in which three connections are made in a square matrix array of three non-addressed resistors that form the three corners of a square. Thus, any two connections in a vertical column and a third one in the same row function as either connection in an X-Y array of conductors. The resistor at the fourth corner of the square shows up as a phantom in parallel with an addressed resistor because the current can travel backwards through that resistor, and forward through the other resistors. Care and additional expense must be taken in the electronics to eliminate the contribution of this phantom. For example, if, as is shown in FIG. 23, a potential V is applied between row and column conductors $X_1Y_1$, to thereby determine the resistance of piezoresistive sensor resistance $R_{11}$, reverse current flow through "phantom" resistor $R_{22}$ would cause the sum of resistances $R_{12}+R_{22}+R_{22}$ to shunt $R_{11}$, resulting in the parallel current flow paths indicated by arrows in FIG. 23, which in turn would result in the following incorrect value of resistance:

$R_{x1}y_1=R_{11}//(R_{12}+[R_{22}]+R_{21})$, $R_{x1}Y_1=R_{11}(R_{12}+[R_{22}]+R_{21})/(R_{11}+R_{12}+[R_{22}]+R_{21})$, where brackets around a resistance value indicate current flow in a counterclockwise direction through that resistor, rather than clockwise, i.e., diagonally downwards towards the left. Thus, for example, if each of the four resistances listed above had a value of 10 ohms, the measured value of $R_{11}$ would be:

$R_{11}=10(10+10+10)/(10+10+10+10)=300/40=7.5$ ohms, i.e., 25% below the actual value, 10 ohms, of $R_{11}$. If the resistance values of $R_{12}$, $R_{22}$ and $R_{21}$ of the three non-addressed piezoresistive sensors 433 were each lower, e.g., 1 ohm, because of greater forces concentrated on those sensors 433, the measured value of $R_{11}$ would be:

$R_{11}=10(1+1+1)/(10+1+1+1)=30/13=2.31$ ohms, i.e., a value of about 77 percent below the actual value of $R_{11}$.

On the other hand, by placing a diode in series with each piezoresistive sensor element 433, as shown in FIG. 24, the electrical resistance of an element measured in a reverse, counterclockwise direction a test current flow through the sensor element, e.g., $R_{22}$, would be for practical purposes arbitrarily large, or infinity compared to the clockwise forward paths of current through the other resistances shown in FIGS. 23 and 24. In this case, the measured resistance value for a 2×2 matrix of four resistances each having a value of 10 ohms would be:

$R_{x1}y_1=10(1+\infty+1)/(10+1+\infty+1)=10$ ohms, the correct value.

Thus, modifying each sensor 433 element to include a p-n junction thereby gives the sensor element a diode-like characteristic that electrically isolates, i.e., prevents backward current flow, through each sensor element 433. This enables the correct value of electrical resistance $R_{x1}y_1$ of each sensor element 433 and hence forces exerted thereon to be measured accurately using row and column matrix addressing rather than requiring a separate pair of conductors for each sensor element.

The above-described components of force minimization apparatus 420 are interconnected to form a closed-loop servo control system. That system is effective in reducing body force concentrations using an algorithm according to the method described herein. An understanding of this method and apparatus may be facilitated by referring to FIG. 41, which is a block diagram of an electro-pneumatic controller system component 420A of apparatus 420, in conjunction with the diagrammatic view of the apparatus shown in FIG. 35, and the perspective view shown in FIG. 39.

Figure 41:
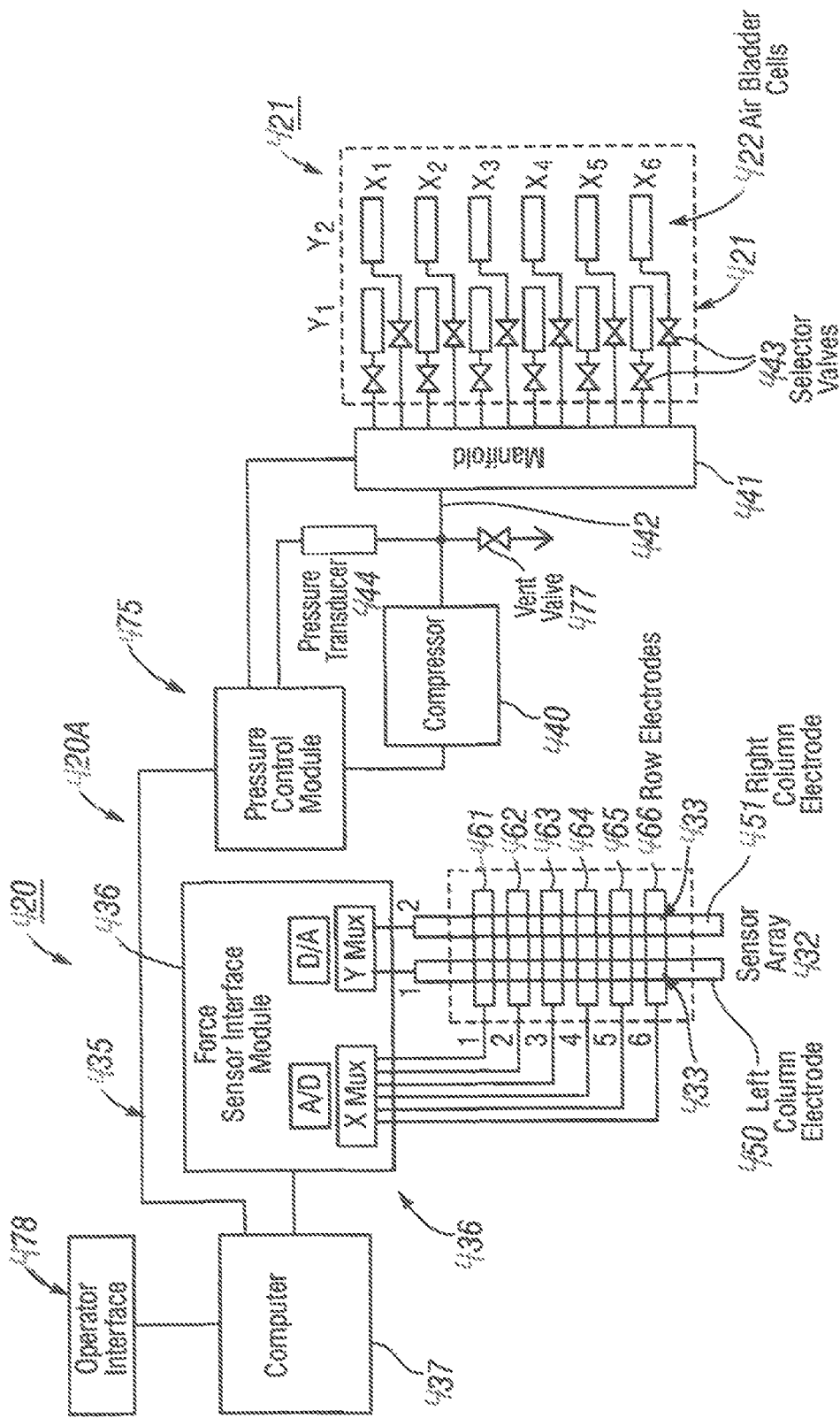
FIG. 41 is a block diagram of electro-pneumatic controller elements of the apparatus of FIG. 35.

Referring to FIG. 41, it may be seen that electro-pneumatic controller apparatus 420A includes a computer 37 which is bidirectionally coupled to force sensor array 432 through force sensor interface module 436. The sensor interface module 436 includes a Digital-to-Analog Converter (DAC) 471 for generating in response to control signals from computer 437 test voltages or currents which are directed to matrix addressed individual force sensors 433.

Individual force sensors 433 are addressed by connecting one terminal of a current or voltage source controlled by DAC 471 to a selected one of X-row conductors 1-6 by an X multiplexer 472, and connecting the other terminal of the source to a selected one of Y-column conductors 1 or 2 by a Y multiplexer 473. Sensor interface module 437 also included an Analog-to-Digital Converter (ADC) 474 which measures the voltage drop or current through a sensor 433 resulting from application of a test current or voltage, and inputs the measured value to computer 437. Using predetermined scale factors, computer 437 calculates the instantaneous value of electrical resistance of a selected addressed sensor 433, and from that resistance value, a corresponding normal force instantaneously exerted on the addressed sensor.

In response to control signals cyclically issued by computer 437, X multiplexer 472 and Y multiplexer 473 are used to cyclically measure the resistance of each force sensor element 433, at a relatively rapid rate of, for example, 3,000 samples per second, enabling computer 437 to calculate the force exerted on each force sensor 433 at that sampling rate.

Referring still to FIG. 41, apparatus 420 includes a pressure control module 475 for dynamically controlling the air pressure in each individual air bladder cell 422, in response to command signals issued by computer 437, based upon values of force measured by sensor array 432 and an algorithm programmed in the computer. As shown in FIG. 41, pressure control module 475 is operably interconnected to air compressor 440 and air pressure transducer 444 at output port 476 of the compressor to pressurize air in the outlet port to a value controllable by computer 437.

Outlet port 476 of compressor 440 is coupled to inlet port 442 of a 12-outlet port manifold 441. In response to electrical control signals issued by computer 437 and routed through pressure control module 475, each of 12 individual air bladder cell inlet selector valves 443 connected to separate outlet ports 443A of manifold 441 is individually controllable.

In a first, open position of a selector valve 443, the air inlet port 431 of a selected air bladder cell 422 is pressurized to a pressure measured by transducer 444 to a predetermined value, by turning on compressor 440, to thereby inflate the cell to a desired pressure. Alternatively, with compressor 440 in an off-mode, a vent valve 477 coupled to the input port 442 of manifold 441 may be opened to deflate an air bladder cell 422 to a lower pressure value by exhausting air to the atmosphere.

After a selected one of the 12 selector valves 443 has been opened in response to a command signal from computer 437 for a time period sufficient to inflate a selected air bladder cell 422 to a predetermined pressure, an electrical signal output by pressure transducer 444, which is proportional to the pressure in that cell and input to computer 437, results in the computer outputting a closure command signal to the valve and a shut-off command signal to compressor 440.

When vent valve 477 and a selected selector valve 443 have been opened in response to command signals from computer 437 to deflate a selected air bladder cell 422 to a lower predetermined pressure, an electrical signal from pressure transducer 444 input to computer 437 results in an electrical closure command signal being output from the computer. That command signal closes vent valve 477 and the open selector valve 443, thereby maintaining the selected lower pressure in the selected air bladder cell. In an exactly analogous fashion, the air pressure in each other air bladder cell 422 is sequentially adjustable by sending a command signal to a selector valve 443 to open that valve, and operating compressor 440 and/or vent valve 477 to inflate or deflate the air bladder cell to a predetermined pressure.

Figure 42:
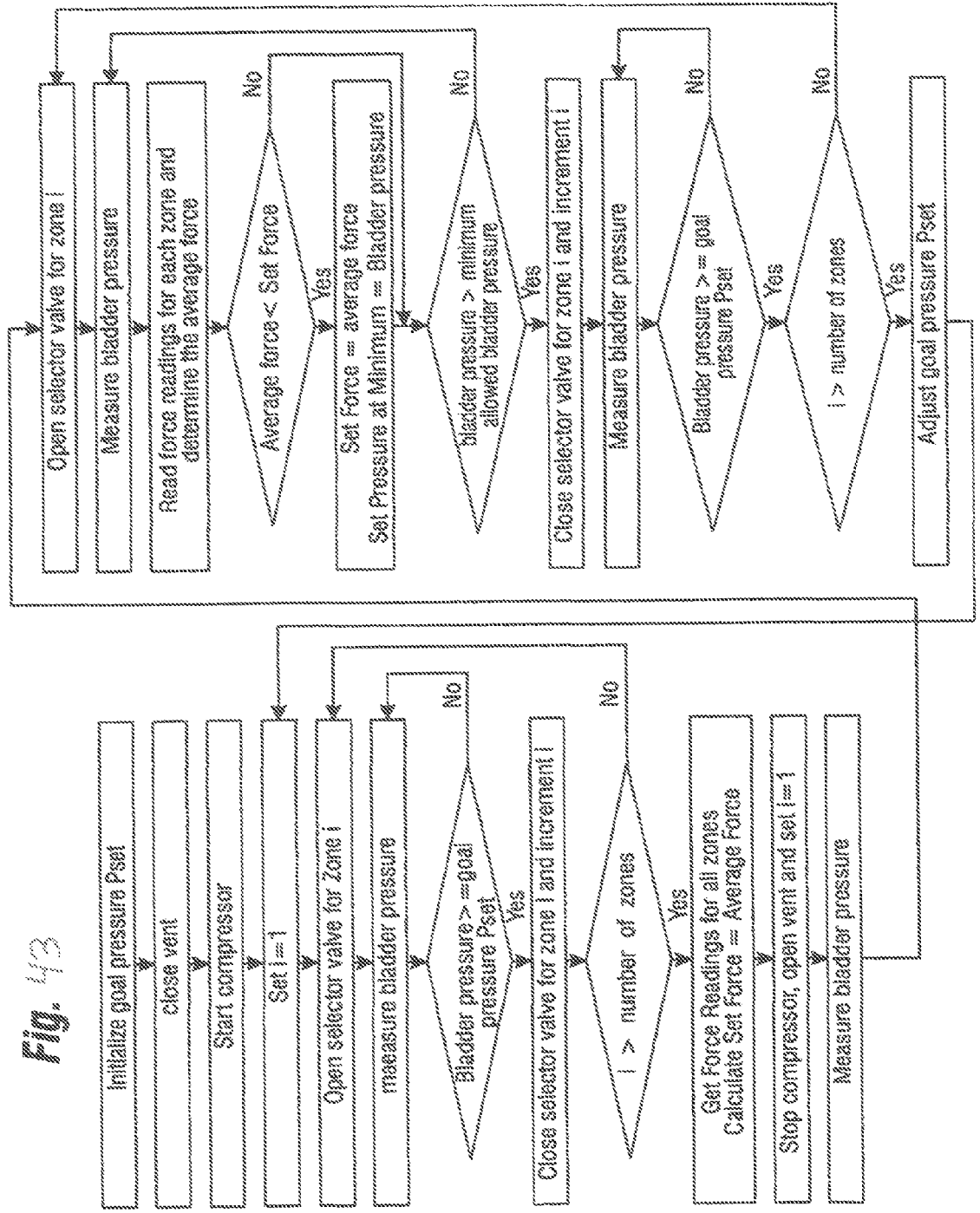
FIG. 42 is a simplified perspective view of the electro-pneumatic controller of FIG. 41.

FIG. 42 is a simplified perspective view of an embodiment of a housing for electro-pneumatic apparatus 420A shown in FIG. 41 and described above. As shown in FIGS. 41 and 42, electro-pneumatic controller 420A includes an operator interface module 478. Operator interface module 478 includes manual controls, including a multi-function, on/off, mode control switch and button 479, up and down data entry slewing buttons 480, 481, and a digital display 482. Display 482 is controllable by switch 479 to selectively display air pressure within and force on selectable air bladder cells 422, and the sum and average of all forces exerted on sensors 433.

As shown in FIG. 42, electro-pneumatic controller 420A is contained in a box-like housing 483 which has protruding from a rear panel 484 thereof an L-bracket 485 for suspending the housing from a side board or end board of a bed. Housing 483 of electro-pneumatic controller 420A also includes a tubular member 486 for interfacing air hoses 487 with air bladder cells 422, row and column conductors 488, 489, to sensors 433 of sensor array 432, and an electrical power cord 490 to a source of electrical power for powering the components of apparatus 420A.

Force Minimization Algorithm

The force minimization apparatus described above is made up of a multiplicity of air 424 bladder cells 422. Each cell 422 has on its upper surface a separate force sensor 433. An air pressure transducer 444 is provided to measure the air pressure in each cell. Each force sensor is located in a potential contact region between a person lying on cushion 421 and the air bladder cell. Each piezoresistive force sensor 433 functions as a force sensitive transducer which has an electrical resistance that is inversely proportional to the maximum force exerted by a person's body on the air bladder cell 422, the maximum force corresponding to the lowest resistance path across any part of each sensor.

As shown in FIG. 37, each air bladder cell 422 supports a different longitudinal zone of the user such as the head, hips or heels. The compressor 440 and selector valves 443 controlling the air pressure in each zone are controlled by sensors 433 and pressure measurements made by pressure transducer 444, using a novel algorithm implemented in computer 437. There can be a minimum of one zone using one air bladder cell 433, and up to N zones using n air bladder cells, wherein each zone has a force sensor 433 to measure the maximum force on that air bladder cell, the pressure transducer 444 being used to measure the air pressure in that air bladder cell. The control algorithm is one of continuous iteration wherein the force sensors 433 determine the peak force on the patient's body, and the pressure transducer 444 measures the pressure at which the force occurs. At the end of a cycle sampling forces on all sensors, the bladder air pressure is restored to the pressure where the force was minimized for all zones. This process continues and the apparatus constantly hunts to find the optimal bladder pressures for each individual cell resulting in minimizing peak forces on a person supported by overlay cushion 421.

Algorithm Description:

Given:

N Zones each containing one air bladder cell and numbered one to N

The air bladder cell of each zone is selectably connectable to an air pressure transducer to measure P#

Each air bladder cell is fitted with an individual force sensor capable of measuring the maximum force F# exerted on the surface of each cell.

A common compressor supplies air at pressures of up to 5 psi to selected individual air bladder cells of the zones. There is a normally closed vent valve for deflating a selected air bladder cell by exhausting air to the atmosphere through the vent valve.

There is a selector valve that selects which air bladder is being inflated with air or deflated by exhausting air to the atmosphere through the vent valve.

Algorithm Steps:
1. Pset::::Pset, start, close vent valve
2. Select zone i=1 by opening selector valve 1
3. Turn the compressor on.
4. Measure the air pressure in the air bladder cell in zone I
5. Pressurize the zone-one air bladder cell to a predetermined upper set pressure and close the selector valve value Pset.
6. Repeat for i+1 until i+1=N
7. Select Zone i=I
8. Obtain the force sensor readings for all zones.
9. Open Vent valve.
10. Deflate the zone-one air bladder cell to a predetermined minimum pressure and monitor all the force sensor readings on all air bladder cells. Maintain bladder pressures in all other air bladder cells at their upper set pressures. Measure forces on all air bladder cells as the single, zone-one air bladder is being deflated and compute the sum and optionally the average of all force sensor readings.
12. Store in computer memory the pressure reading of the zone-one air bladder cell at which the minimum sum and optionally the average of all force sensor readings occurs.
13. Restore the pressure in the zone one air bladder cell to the value where the minimum sum and average force sensor readings for all the force sensors was obtained.
14. Close the zone-one selector valve. Maintain the pressure in zone one.
15. Set: Count=i+1.
16. Repeat steps 2 thru 15 until Count=i+1=N.
17. Set: Pset=Pset, start−(Count*20%_(i.e., reduce the initial pressure in the zone one bladder).
18. Repeat Steps 2 thru 16 (i.e., with a reduced initial pressure).

Caveat

19. Constantly monitor all force sensors and if significant change (Delta F>0.2*F#) is detected (patient moved) start over at Step 1.

FIG. 43 is a flow chart showing the operation of apparatus 420 utilizing the algorithm described above. Table 1 lists appropriate lower and upper initial set pressures for bladders 422, as a function of the weight of a patient or other person supported by overlay cushion 421 of the apparatus.

TABLE 1

| Patient Weight | Minimum Pressures | Start Pressure |
| --- | --- | --- |
| 75-119 Pounds | 5.5" ± 0.7:$H_2O$ | 6.5" ± 0.7:$H_2O$ |
| | 10.31 ± 2 mmHg | 12.18 ± 2 mmHg |
| 120-164 Pounds | 6" ± 0.7:$H_2O$ | 8" ± 0.7:$H_2O$ |
| | 11.25 ± 2 mmHg | 15 ± 2 mmHg |
| 165-199 Pounds | 8" ± 0.7:$H_2O$ | 10" ± 0.7:$H_2O$ |
| | 15 ± 2 mmHg | 18.75 ± 2 mmHg |
| 200-250 Pounds | 10" ± 0.7:$H_2O$ | 12" ± 0.7:$H_2O$ |
| | 18.75 ± 2 mmHg | 22.49 ± 2 mmHg |
| Maximum Pressure | | 26" ± 0.7:$H_2O$ |
| | | 48.74 ± 4 mmHg |

In a variation of the method and apparatus according described above, after the pressures in each air bladder cell 422 have been optimized for minimum force concentration, inlet tubes 431 may be permanently sealed, and the adaptive cushion 421 permanently disconnected from pressure control module 475. This variation would also enable the custom fabrication of cushions 421 using air bladder cells 422, for customizing chair cushions to minimize force concentrations on a particular individual. Similarly, the variation of the method and apparatus could be used to customize saddle cushions or car seats.

What is claimed is:

1. A flexible force sensing array comprising:
an elastically stretchable sheet;
a plurality of first conductive paths supported on said elastically stretchable sheet;
a layer of sensing material positioned in contact with said first conductive paths, said layer of sensing material having an electrical characteristic that varies in response to physical forces exerted thereon;
a layer of semiconductive material positioned in contact with said layer of sensing material on a side of said layer of sensing material opposite said plurality of first conductive paths; and
a plurality of second conductive paths positioned in contact with said layer of semiconductive material on a side of said layer of semiconductive material opposite said layer of sensing material.

2. The array of claim 1 wherein said layer of sensing material includes a layer of piezoresistive material.

3. The array of claim 2 wherein said layer of piezoresistive material is supported by an elastically stretchable substrate.

4. The array of claim 3 wherein said elastically stretchable substrate is made at least partially of nylon.

5. The array of claim 4 wherein said plurality of second conductive paths are supported on a second elastically stretchable sheet, and said elastically stretchable sheet and said second elastically stretchable sheet are both made from woven fabric.

6. The array of claim 2 wherein said semiconductive layer is coated onto said layer of sensing material and includes a metallic oxide.

7. The array of claim 2 further including a cover sheet positioned in contact with said elastically stretchable sheet, said cover sheet being made of thin, flexible, and elastically stretchable material.

8. The array of claim 1 wherein said plurality of second conductive paths are supported on a second elastically stretchable sheet.

9. The array of claim 8 wherein said elastically stretchable sheet and said second elastically stretchable sheet are both made from woven fabric.

10. The array of claim 9 wherein said woven fabric includes nylon.

11. The array of claim 1 wherein said semiconductive layer is coated onto said layer of sensing material and includes a metallic oxide.

12. A flexible force sensing array comprising:
a first elastically stretchable sheet;
a plurality of first conductive paths supported on said first elastically stretchable sheet, said first conductive paths being parallel to each other;
an intermediate elastically stretchable sheet positioned in contact with said first elastically stretchable sheet, said intermediate elastically stretchable sheet including sensing material thereon that has an electrical characteristic that varies in response to applied physical forces;
a layer of semiconductive material positioned in contact with said intermediate elastically stretchable sheet to thereby form with said sensing material a PN junction;
a second elastically stretchable sheet; and
a plurality of second conductive paths supported on said second elastically stretchable sheet and in electrical contact with said semiconductive material, said second conductive paths being parallel to each other and transverse to said first conductive paths.

13. The array of claim 12 wherein said sensing material is a piezoresistive material.

14. The array of claim 13 wherein said first and second elastically stretchable sheets are both made at least partially of nylon.

15. The array of claim 14 wherein said semiconductive layer includes a metallic oxide.

16. The array of claim 14 wherein semiconductive layer includes copper oxide.

17. The array of claim 13 further including a cover sheet positioned in contact with said first elastically stretchable sheet, said cover sheet being made of thin, flexible, and elastically stretchable material.

18. The array of claim 13 further including:
a plurality of air bladder cells coupled to one side of said array;
a controller in communication with said array; and
a source of pressurized air in communication with said controller wherein said controller adjusts the inflation levels within said air bladder cells based upon outputs from said flexible force sensing array.

19. The array of claim 18 wherein said controller is adapted to adjust the inflation levels within said air bladder cells such that interface forces exerted on a patient positioned on said air bladder cells are less concentrated.

* * * * *